(12) United States Patent
Okuyama et al.

(10) Patent No.: US 7,994,315 B2
(45) Date of Patent: Aug. 9, 2011

(54) INTERMEDIATE COMPOUND FOR SYNTHESIZING PHARMACEUTICAL AGENT AND PRODUCTION METHOD THEREOF

(75) Inventors: Masahiro Okuyama, Osaka (JP); Fumiaki Uehara, Osaka (JP); Hiroshi Iwamura, Osaka (JP); Kazutoshi Watanabe, Osaka (JP)

(73) Assignees: Mitsubishi Tanabe Pharma Corporation, Osaka (JP); Sanofi-Aventis, Paris (FR)

( * ) Notice: Subject to any disclaimer, the term of this patent is extended or adjusted under 35 U.S.C. 154(b) by 481 days.

(21) Appl. No.: 11/996,205

(22) PCT Filed: Jul. 21, 2006

(86) PCT No.: PCT/JP2006/314932
§ 371 (c)(1),
(2), (4) Date: Mar. 20, 2008

(87) PCT Pub. No.: WO2007/011065
PCT Pub. Date: Jan. 25, 2007

(65) Prior Publication Data
US 2009/0156804 A1    Jun. 18, 2009

(30) Foreign Application Priority Data

Jul. 22, 2005 (JP) ................................ 2005-213311
Sep. 14, 2005 (JP) ................................ 2005-267485
Jan. 24, 2006 (JP) ................................ 2006-015436

(51) Int. Cl.
*C07D 265/30* (2006.01)
(52) U.S. Cl. .................................................... 544/106
(58) Field of Classification Search .................. 544/106
See application file for complete search history.

(56) References Cited

U.S. PATENT DOCUMENTS
4,104,386 A    8/1978    Barreau et al.

FOREIGN PATENT DOCUMENTS
CA    1 211 126    9/1986
(Continued)

OTHER PUBLICATIONS

Database CAS Online and CASREACT on STN, Chem. Abstr., accession No. 1995:72184, Yordanova et al., Dokladi na Bulgarskata Akademiya na Naukite (1993), 46(3), 63-5, abstract.*

(Continued)

*Primary Examiner* — Rebecca Anderson
(74) *Attorney, Agent, or Firm* — Greenblum & Bernstein, P.L.C.

(57) ABSTRACT

Production method of an optically active morpholine compound represented by the formula 10, or a compound represented by the formula 55, which includes the following steps:

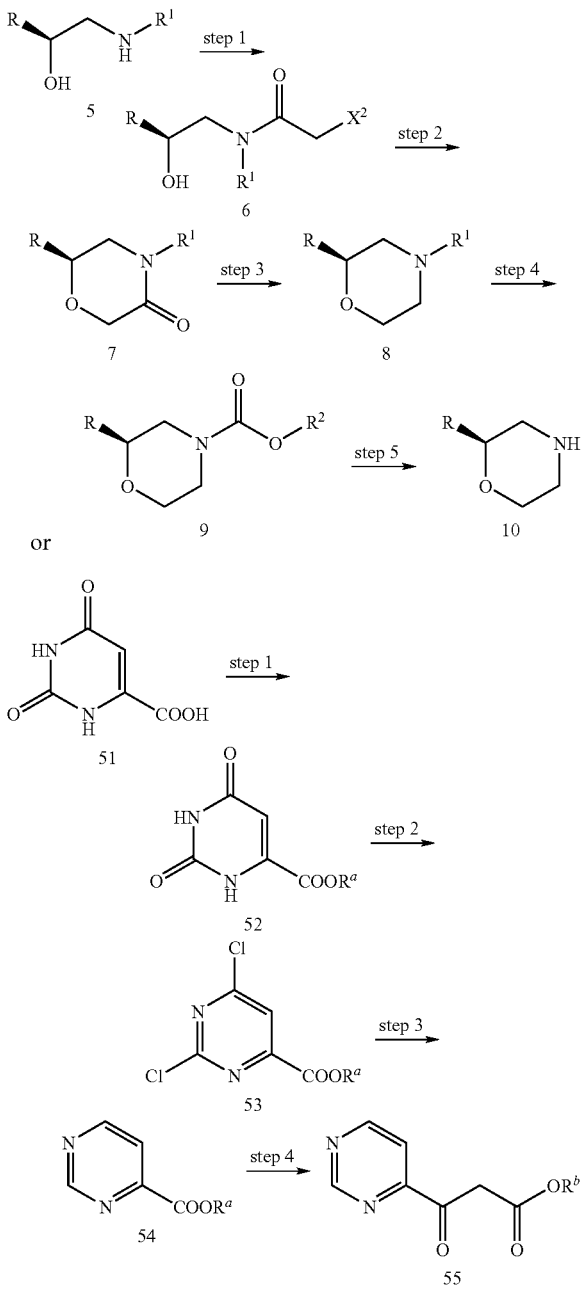

wherein each symbol is as defined in the specification. An optically active 2-aryl-substituted morpholine compound and 3-oxo-3-(pyrimidin-4-yl)propionate, which are important as starting materials for synthesizing 2-(2-arylmorpholin-4-yl)-1-methyl-1H-[4,4']bipyrimidinyl-6-one having a tau protein kinase 1 inhibitory activity and useful as a therapeutic drug for Alzheimer's disease and the like, can be produced in a high yield by an industrially advantageous method.

2 Claims, No Drawings

U.S. PATENT DOCUMENTS

| | | | |
|---|---|---|---|
| 4,105,790 | A | 8/1978 | Hughes |
| 4,603,019 | A | 7/1986 | Lafon |
| 6,130,243 | A | 10/2000 | Takahashi et al. |
| 6,515,023 | B2 | 2/2003 | Barrow et al. |
| 2005/0187388 | A1 | 8/2005 | Cebula et al. |

FOREIGN PATENT DOCUMENTS

| | | |
|---|---|---|
| EP | 0 007 206 | 2/1983 |
| FR | 1 525 298 | 4/1968 |
| FR | 2 285 886 | 4/1976 |
| JP | 52-105181 | 9/1977 |
| JP | 60-152450 | 8/1985 |
| JP | 63-192744 | 8/1988 |
| JP | 03-200751 | 9/1991 |
| SU | 722481 | 3/1980 |
| SU | 837324 | 6/1981 |
| SU | 965351 | 10/1982 |
| WO | 83/29891 | 9/1983 |
| WO | 93/10074 | 5/1993 |
| WO | 95/02407 | 1/1995 |
| WO | 96/35685 | 11/1996 |
| WO | 02/48090 | 6/2002 |
| WO | 02/094770 | 11/2002 |
| WO | 03/027080 | 4/2003 |
| WO | 2004/043443 | 5/2004 |
| WO | 2004/052372 | 6/2004 |
| WO | WO 2004/052372 A1 * | 6/2004 |
| WO | 2004/085408 | 10/2004 |
| WO | 2005/061468 | 7/2005 |
| WO | 2006/036015 | 4/2006 |

OTHER PUBLICATIONS

J. Y. L. Chung et al., "Enantioselective Nitrile Anion Cyclization to Substituted Pyrrolidines. A Highly Efficient Synthesis of (3S,4R)-N-tert-Butyl-4-Arylpyrrolidine-3-Carboxylic Acid," J. Org. Chem., vol. 70, pp. 3592-3601 (2005).

M. Sawamura et al., "The Asymmetric Aldol Reaction of Tosylmethyl Isocyanide and Aldehydes Catalyzed by Chiral Silver(I) Complexes," J. Org. Chem., vol. 55, No. 24, pp. 5935-5936 (1990).

V. I. Kuliskii et al. "Radioprotective effect of hydroxyphenylethanolamines phenolic hydroxyl esters," published in Radiatsionnaya Biologiya, Radioekologiya, 38(1), pp. 55-61 (1998).

S. Sohda et al., "New Bronchodilators. Synthesis and Bronchodilating Activity of Some 3-(Alkoxymethyl)-α-(N-substituted aminomethyl)-4-hydroxybenzyl Alcohols," J. Med. Chem., vol. 22, No. 3, pp. 279-286 (1979).

Chemical Abstract of M. I. Dorokhova et al., "Conversion of the configuration of optically active 1-(m-nitrophenyl)-2-(methylamino)ethanols," published in Khimiko-Farmatsevticheskii Zhurnal, vol. 8, No. 4, pp. 14-16 (1974).

B. Hu et al., "2,4-Thiazolidinediones as Potent and Selective Human $\beta_3$ Agonists," Bioorganic & Medicinal Chemistry Letters, vol. 11, pp. 757-760 (2001).

R. L. Dow et al., "Potent and selective, sulfamide-based human $\beta_3$-adrenergic receptor agonists," Bioorganic & Medicinal Chemistry Letters, vol. 14, pp. 3235-3240 (2004).

M. A. Ashwell et al., "4-Aminopiperidine Ureas as Potent Selective Agonists of the Human $\beta_3$-adrenergic receptor," Bioorganic & Medicinal Chemistry Letters, vol. 11, pp. 3123-3127 (2001).

PD Avramova et al., "Synthesis, toxicological and pharmacological assessment of esters of carbonic and carbamic acids with 2-aryl-4-hydroxyethylmorpholines," Eur. J. Med. Chem., vol. 31, pp. 909-914 (1996).

K. Yordanova et al., "Eine neue Methode zur Darstellung von 2,4-disubstituierten Morpholinen," Chem. Ber., vol. 115, pp. 2635-2642 (1982).

K. Yordanova et al., "Synthese von 3,4-Dialkyl-2-phenylmorpholinen," Arch. Pharm. (Weinheim), vol. 323, pp. 41-42 (1990).

R. Perrone et al., "Oxygen Isosteric Derivatives of 3-(3-Hydroxyphenyl)-N-n-propylpiperidine," J. Med. Chem., vol. 35, pp. 3045-3049 (1992).

D. T. Greenwood et al., "2-Aryloxymethyl-2,3,5,6-tetrahydro-1,4-oxazines, a New Class of Antidepressants," J. Med. Chem., vol. 18, No. 6, pp. 573-577 (1975).

T. Kojima et al., "Synthesis of (±)-2-[Inden-7-yloxy]methyl]morpholine Hydrochloride (YM-08054, Indeloxazine Hydrochloride) and Its Derivatives with Potential Cerebral-Activating and Antidepressive Properties," Chem. Pharm Bull., vol. 33, No. 9, pp. 3766-3774 (1985).

R. Houssin et al., "Synthesis and Configurational Study of 2-Arylmorpholines," Heterocycles, vol. 34, No. 7, pp. 1343-1352 (1992).

R. Nieduzak et al., "Multigram Lipase-Catalyzed Enatioselective Acylation in the Synthesis of the Four Stereoisomers of a New Biologically Active α-Aryl-4-Piperidinemethanol Derivative," Tetrahedron Asymmetry, vol. 2, No. 2, pp. 113-122 (1991).

P. Saravanan et al., "Synthesis of chiral non-racemic 1,2-diamines from O-acetyl mandelic acid: application in enantioselective deprotonation of epxoides and diethylzinc addition to aldehydes," Tetrahedron, vol. 58, pp. 4693-4706 (2002).

H. Nakatani, "Studies on Pharmaceutical Preparation of Orotic Acid. VII. Water Soluble Properties of Orotic Acid Salts.," Yakugaku Zasshi, vol. 84, No. 11, pp. 1057-1061 (1964).

W. Klötzer et al., "Synthese von 5-deuterierter Orosäure und 5-deuterierten Orotsäurederivaten," Scientia Pharmaceutica, vol. 51, pp. 374-378 (1983).

H. Gershon, "Pyrimidines. II. Chlorinated Pyrimidines Derived from Orotic Acid," J. Org. Chem., vol. 27, pp. 3507-3510 (1962).

L. O. Ross et al., "Potential Anticancer Agents. XLIV. Some Derivatives of Uracil-5-and-6-carboxylic Acid," J. Org. Chem., vol. 25, pp. 1950-1953 (1960).

W. Fürst et al., "Prodrug approach of orotic acid using an absorption model," International Journal of Pharmaceutics, vol. 61, pp. 43-49 (1990).

H. Vanderhaeghe, "La Préparation de l'acide orotique et de quelques dérivés," Bull. Soc. Chim. Belg., vol. 62, pp. 611-618 (1953).

J. J. Fox et al., "Spectrophotometric Studies of Nucleic Acid Derivatives and Related Compounds as a Function of pH," Biochemica et Biophysica Acta., vol. 23, pp. 295-305 (1957).

M. Bachstez, "Über die Konstitution der Orotsäure.," Chem. Ber., vol. 63, pp. 1000-1007 (1930).

M. Bachstez, "Über die Alkylderivate der Orotsäure.," Chem. Ber., vol. 64, pp. 2683-2688 (1931).

Khimiya Seterotsiklicheskikh Soedinenii, No. 6, pp. 818-821 (1986).

G. D. Daves et al., "Primidines. II. Orotic Acid Analog," J. Org. Chem., vol. 26, pp. 2755-2763 (1961).

J.-P. Gallemaers et al., "Synthesis and Conversion of 5-Amino-4-Pyrimidinecarboxylic Acids into 4-Hydroxypyrumidines via Their Diazonium Salts," Tetrahedron Lett., No. 9, pp. 693-694 (1976).

G. A. Archer et al., "Quinazolines and 1,4-Benzodiazepines. 82. 5-Pyrimidyl- and 5-Pyrazinylbenzodiazepines," J. Med. Chem., vol. 20, No. 10, pp. 1312-1317 (1977).

J. L. Wong et al., "The Synthesis of Pyrrolo[1,2-c]pyrimidine (6-Azapyrrocoline)," J. Org. Chem., vol. 30, pp. 2398-2402 (1965).

J. F. W. Mcomie et al., "Pyrimidines. Part VI. 5-Bromopyrimidine.," J. Chem. Soc., pp. 3129-3131 (1953).

Khimiya Seterotsiklicheskikh Soedinenii, No. 4, pp. 530-535 (1981).

English translation of S. A. Stekhova et al., "Tautomerism of Azine Derivatives. 4. * Keto-Enol Tautomerism of β-Keto Esters of the Azine Series," Khimiya Seterotsiklicheskikh Soedinenii, No. 6, pp. 822-826 (1980).

A. M. Kawamoto et al., "Enantioselective synthesis of β-hydroxy amines and aziridines using asymmetric transfer hydrogenation of α-amino ketones," J. Chem. Soc. Perkin Trans. 1, vol. 16, pp. 1916-1928 (2001).

Registry [Online] including 51017-53-9 and 50741-73-6 and 52887-01-1, Nov. 16, 1984.

Registry [Online] including 301193-20-4, Nov. 3, 2000.

English translation of Office Action in counterpart Chinese Application No. 200680026779.8 dated Apr. 23, 2010.

Bettoni et al., Tetrahedron, vol. 36, 1980, pp. 409-415.

Bouron et al., Tetrahedron Letters, vol. 40, 1999, pp. 7227-7230.

Database Beilstein, Beilstein Institute for Organic Chemistry, Frankfurt-Main, DE, 1980 Database Accession No. 3360740.
Ono et al. Bulletin of the Chemical Society of Japan, vol. 51, No. 8, 1978, pp. 2401-2404.
Tumkyavichyus et al., Chemistry of Heterocyclic Compounds, vol. 22, No. 6, 1986, pp. 647-650.
Smith et al., Org. Chem., vol. 20, 1955, pp. 829-838.
Stekhova et al., Chemistry of Heterocyclic Compounds, vol. 16, No. 6, 1980, pp. 640-644.

Extended European Search Report for European Application No. 10002309.2 published Jul. 14, 2010.
Extended European Search Report for European Application No. 10002308.4 published Jul. 14, 2010.
English Language Abstract JP 03-200751 published Sep. 2, 1991.
English Language Abstract JP 63-192744 published Aug. 10, 1988.
English Language Abstract JP 60-152450 published Aug. 10, 1985.

* cited by examiner

INTERMEDIATE COMPOUND FOR SYNTHESIZING PHARMACEUTICAL AGENT AND PRODUCTION METHOD THEREOF

TECHNICAL FIELD

The present invention relates to a production method of an optically active 2-aryl-substituted morpholine compound useful as an intermediate for synthesizing a pharmaceutical agent, and a novel compound obtained by the production method. The present invention also relates to a production method of 3-oxo-3-(pyrimidin-4-yl)propionate useful as an intermediate for synthesizing a pharmaceutical agent.

BACKGROUND ART

WO 2003/027080 describes that compounds such as 2-(2-arylmorpholin-4-yl)-1-methyl-1H-[4,4']bipyrimidinyl-6-one represented by the following formula 43, and the like have tau protein kinase 1 inhibitory activity and are useful as a therapeutic drug for Alzheimer's disease and the like. It also describes that the compound of the formula 43 is synthesized from 2-chloro-1-methyl-1H-[4,4']bipyrimidinyl-6-one of the formula 41 and an aryl-substituted morpholine compound of the formula 42 as starting materials.

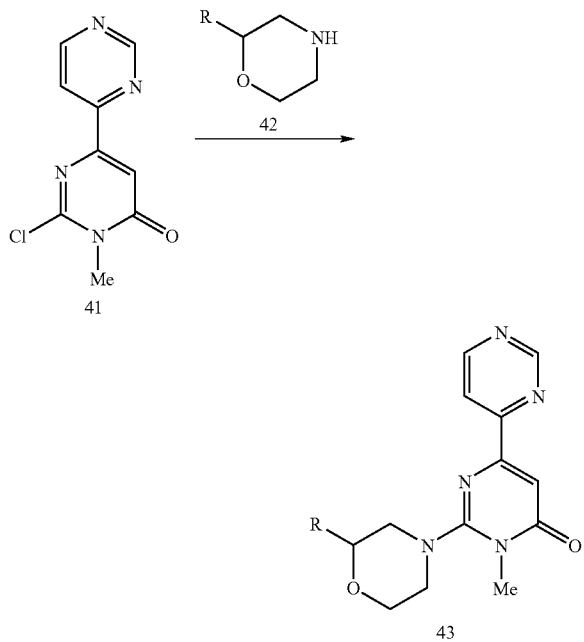

wherein R is an aryl optionally having substituent(s) or a heteroaryl optionally having substituent(s).

Therefore, 2-chloro-1-methyl-1H-[4,4']bipyrimidinyl-6-one of the formula 41 and the aryl-substituted morpholine compound of the formula 42 are used as intermediates for synthesizing a pharmaceutical agent.

According to WO 2004/085408, moreover, the compound of the formula 41 can be synthesized from ethyl 3-oxo-3-(pyrimidin-4-yl)propionate of the formula 44 via 2-mercapto-1-methyl-1H-[4,4']bipyrimidinyl-6-one of the formula 45.

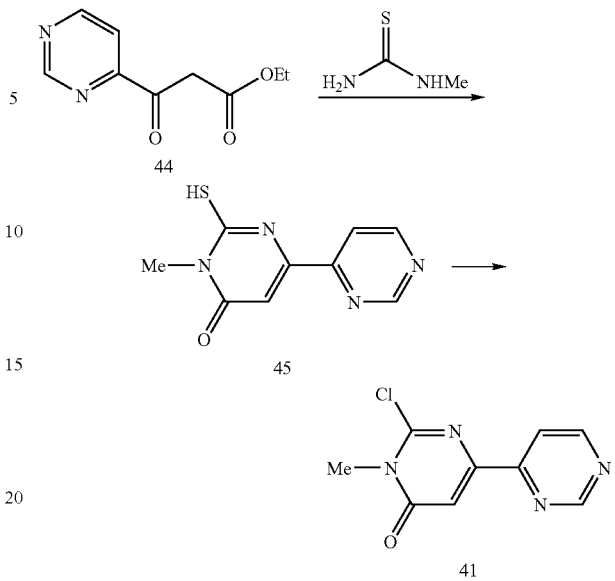

Therefore, the compound of the formula 44 is an important starting compound for synthesizing compounds such as 2-(2-arylmorpholin-4-yl)-1-methyl-1H-[4,4']bipyrimidinyl-6-one etc.

Eur. J. Med. Chem., 31, 909-914 (1996) describes that 2-aryl-4-(2-hydroxyethyl)morpholine can be synthesized by heating phenacyl chloride, which is not substituted at the 4-position or has a chlorine atom or a methyl group at the 4-position, and N,N-diethanolamine in formic acid.

Chem. Ber., 115, 2635-2642 (1982) describes that 2-aryl-4-alkylmorpholine can be synthesized by heating 2-acetoxy-acetophenone, which is not substituted at the 4-position or has a chlorine atom, a bromine atom or a methoxy group at the 4-position, and N-alkylethanolamine wherein the alkyl moiety is methyl, ethyl, propyl, isopropyl, butyl or benzyl, in formic acid.

Arch. Pharm. (Weinheim), 323, 41-42 (1990) describes that 2-phenyl-3,4-dimethylmorpholine can be synthesized by heating 2-bromopropiophenone and N-methylethanolamine in formic acid.

J. Med. Chem., 35, 3045-3049 (1992) describes that 2-aryl-4-propylmorpholine can be synthesized by reducing the carbonyl group of phenacyl bromide having a substituent at the 2- or 3-position, reacting the obtained compound with a base to give 2-aryloxirane, reacting the obtained compound with propylamine to give 1-aryl-2-(propylamino)ethanol, reacting the obtained compound with bromoacetyl chloride in the presence of potassium hydroxide to give 2-aryl-4-propylmorpholin-5-one, and reducing the obtained compound; and that 2-aryl-4-propylmorpholine can be synthesized by heating phenacyl bromide having a substituent at the 2- or 3-position or bromoacetylthiophene and N-propylethanolamine in formic acid.

J. Med. Chem., 18, 573 (1975) describes that 2-aryloxymethyl-4-alkylmorpholine can be synthesized by reacting 1-alkylamino-3-aryloxypropan-2-ol wherein the alkyl moiety is a hydrogen atom, methyl, isopropyl, allyl, cyclopentyl or benzyl with chloroacetyl chloride, reacting the obtained compound with sodium methylate, and reducing the obtained compound.

Chem. Pharm. Bull., 33, 3766 (1985) describes that 2-aryloxymethylmorpholine can be synthesized by reacting 2-(aryloxymethyl)oxirane with 2-aminoethyl hydrogensulfate in the presence of sodium hydroxide.

Heterocycles, 34, 1343 (1992) describes that 2-aryl-4-substituted or unsubstituted morpholine can be synthesized by reacting 2-bromoalkyl aryl ketone with N-substituted or unsubstituted benzylamine, reducing the carbonyl group of the obtained 2-aminoketone, and reacting the obtained 1-aryl-2-aminoethanol with oxirane; or by reacting 2-bromoalkyl aryl ketone with N-substituted or unsubstituted 2-aminoethanol, reducing the carbonyl group of the obtained 2-(2-hydroxyethyl)aminoketone, and reacting the obtained 1-aryl-2-(2-hydroxyethyl)aminoethanol with hydrobromic acid.

In addition, French patent No. 2285886 describes that a 2-arylmorpholine compound can be synthesized by, for example, reacting a compound of the formula:

wherein X is a halogen, with a compound of the formula:

wherein Ph is a phenyl optionally having substituent(s). The optical isomer thereof can be obtained by subjecting the obtained racemic 2-arylmorpholine compound to optical resolution by a conventional method.

These methods are described as synthetic methods of racemic 2-aryl-4-substituted morpholine, and an efficient synthetic method of an optically active form thereof is not known. Particularly, as to 2-arylmorpholine, since the method for obtaining one enantiomer by optical resolution theoretically cannot achieve a yield exceeding 50%, because the other enantiomer cannot be efficiently converted to the racemate or the reverse enantiomer due to its chemical structure, this method is synthetically highly disadvantageous. Moreover, when N-unsubstituted morpholine is to be obtained from the N-substituted morpholines obtained by the methods described in Eur. J. Med. Chem., 31, 909-914 (1996); Chem. Ber., 115, 2635-2642 (1982); Arch. Pharm. (Weinheim), 323, 41-42 (1990); or J. Med. Chem., 35, 3045-3049 (1992), these references do not provide a synthetic example for N-benzyl group and the like permitting easy deprotection, or the yield is low, and in the case of a substituent showing a high yield, severe deprotection conditions are necessary. As such, they are not synthetically advantageous. J. Med. Chem., 18, 573 (1975); and Chem. Pharm. Bull., 33, 3766 (1985) that describe synthetic methods of N-unsubstituted morpholine do not describe a synthetic example of 2-arylmorpholine, and the synthesis method described in Heterocycles, 34, 1343 (1992) is problematic in that an isomer mixture is produced during the synthesis, identification of intermediate is complicated due to a treatment under strong acidic conditions in the final step, applicability to functional group is considerably limited, and the like, and French patent No. 2285886 poses concerns about the synthesis and handling of reaction intermediate.

Tetrahedron Asymmetry, Vol. 2, No. 2, pp 113-122, 1991 describes that S-(+)-4-fluorostyrene oxide (aka: (2S)-2-(4-fluorophenyl)oxirane) or R-(−)-4-fluorostyrene oxide can be synthesized by reducing 4-fluorophenacyl chloride, subjecting the obtained 2-chloro-1-(4-fluorophenyl)ethanol to optical resolution using lipase P, and reacting the obtained optically active 2-chloro-1-(4-fluorophenyl)ethanol with sodium hydroxide.

Tetrahedron, 58 (2002) 4693-4706 describes that optically active β-amino alcohol such as (1S)-1-phenyl-2-(benzylamino)ethanol and the like can be synthesized from optically active O-acetylmandelic acid.

However, it does not describe that optically active β-amino alcohol can be synthesized from arylacetyl chloride compound such as 4-fluorophenacyl chloride and the like via optically active 2-aryloxirane; and that optically active 2-aryl-substituted morpholine compound can be synthesized from optically active β-amino alcohol.

Some orotic acid esters are known, and some of them are commercially available. In addition, as methods for synthesizing orotate from orotic acid or its derivative, the following methods are known.

Yakugaku Zasshi, 84, 1057-1061 (1964) describes that ethyl orotate can be synthesized by heating orotic acid in a mixture of sulfuric acid and ethanol.

Scientia Pharmaceutica, 51, 374 (1984) describes that ethyl orotate can be synthesized by reacting orotonitrile with hydrogen chloride in ethanol to give imino ester, which is then hydrolyzed.

J. Org. Chem, 27, 3507 (1962) describes that methyl orotate can be synthesized by reacting orotic acid with thionyl chloride in the presence of a catalytic amount of pyridine to give orotyl chloride, which is then heated in methanol.

J. Org. Chem, 25, 1950 (1960) describes that butyl orotate can be synthesized by heating orotic acid in butanol in the presence of a catalytic amount of sulfuric acid.

International Journal of Pharmaceutics, 61, 43 (1990) describes that the corresponding orotate can be synthesized by heating orotic acid in alcohol saturated with hydrogen chloride or alcohol containing conc. sulfuric acid.

Bull. Soc. Chim. Belg., 1953, 611 describes that the corresponding orotate can be synthesized by heating orotic acid in methanol or ethanol saturated with hydrogen chloride.

Biochimica et Biophysica Acta., 23, 295 (1957) describes that the corresponding orotate can be synthesized by heating orotic acid in methanol or ethanol saturated with hydrogen chloride. This reference also describes that the corresponding orotate can be synthesized by reacting silver orotate with methyl iodide or ethyl iodide by the methods described in Ann. Soc. Chim. Milano, II, 18, 71 (1905); Chem. Ber., 63, 1000 (1930); or Chem. Ber., 64, 2683 (1931).

WO83/02891 describes that butyl orotate can be obtained at 56% by heating orotic acid together with butanol and sulfuric acid in toluene with dehydration for 12 hrs.

France Patent No. 1525298 describes that butyl orotate can be obtained by heating orotic acid together with butanol and p-toluenesulfonic acid in toluene with dehydration for 5 hrs, and further repeating (5 times) addition of p-toluenesulfonic acid, butanol and toluene and heating the mixture thereof, and that the corresponding amyl ester or isoamyl ester can be obtained by a similar method.

WO95/02407 describes that the corresponding orotate can be synthesized by heating methyl orotate in 2-ethylbutanol or 1-methylpropanol in the presence of sulfuric acid.

These methods are associated with the following problems. For example, Yakugaku Zasshi, 84, 1057-1061 (1964) requires complicated operation such as neutralization, extraction etc. Scientia Pharmaceutica, 51, 374 (1984) requires a long route and does not afford a direct synthesis. J. Org. Chem, 27, 3507 (1962) requires a long reaction time and multiple steps, and produces toxic gas such as hydrogen chloride, sulfur dioxide, methyl chloride and the like. J. Org. Chem, 25, 1950 (1960) requires a long reaction time and contains remaining starting materials. International Journal of Pharmaceutics, 61, 43 (1990); Bull. Soc. Chim. Belg., 1953, 611; and Biochimica et Biophysica Acta., 23, 295 (1957) require use of toxic hydrogen chloride and a long reaction time. Ann. Soc. Chim. Milano, II, 18, 71 (1905); Chem. Ber., 63, 1000 (1930); and Chem. Ber., 64, 2683

(1931) use a silver salt problematic in photostability and cost. WO83/02891 requires a long reaction time for a poor yield. France Patent No. 1525298 requires a long reaction time and complicated operation. WO95/02407 requires a long reaction time.

As a reaction for leading orotate to 2,6-dichloropyrimidine-4-carboxylate, Khimiya Seterotsiklicheskikh Soedinenii, 1986, 818 describes that n-butyl 2,6-dichloropyrimidine-4-carboxylate can be synthesized by chlorinating butyl orotate with phosphorus oxychloride. J. Org. Chem, 27, 3507 (1962) describes that methyl 2,6-dichloropyrimidine-4-carboxylate can be synthesized by chlorinating methyl orotate with phosphorus oxychloride. J. Org. Chem, 26, 2755 (1961) describes that methyl 2,6-dichloropyrimidine-4-carboxylate can be synthesized by chlorinating methyl orotate with phosphorus oxychloride.

As the dechlorination reaction of 2,6-dichloropyrimidine-4-carboxylate, Tetrahedron Lett., 1976, 693 has reported a dechlorination reaction of ethyl 2,6-dichloro-5-nitropyrimidine-4-carboxylate with magnesium oxide and triethylamine as a base in 2 steps while reducing nitro group.

As synthetic methods for pyrimidine-4-carboxylate other than the above-mentioned, J. Med. Chem, 20, 1312 (1977) has reported that methylpyrimidine-4-carboxylate can be synthesized by oxidizing 4-methylpyrimidine with selenium dioxide to give pyrimidine-4-carboxylic acid, and reacting the obtained compound with diazomethane. However, this method is problematic in that it uses highly toxic selenium compound.

While J. Org. Chem., 30, 2398 (1965) describes that methylpyrimidine-4-carboxylate can be synthesized by treating 5-bromo-2-methylthiopyrimidine-4-carboxylic acid with Raney-nickel, as described in J. Chem. Soc., 1953, 3129, to give pyrimidine-4-carboxylic acid, and heating the obtained compound in methanol in the presence of concentrated hydrochloric acid. This method is problematic in the availability of the starting materials.

As regards 3-oxo-3-(pyrimidin-4-yl)propionate, it is described in Khimiya Seterotsiklicheskikh Soedinenii, 1981, 530; and Khimiya Seterotsiklicheskikh Soedinenii, 1980, 822, and JP-A-52-105181 describes synthetic example of ethyl 3-oxo-3-(pyrimidin-4-yl)propionate, which comprises reacting methylpyrimidine-4-carboxylate with ethyl acetate in the presence of a base. However, no example is known where this compound was synthesized from orotic acid by the steps of the present invention.

DISCLOSURE OF THE INVENTION

As to the method for obtaining an optically active 2-aryl-substituted morpholine compound by subjecting racemic 2-aryl-substituted morpholine compound obtained by the production method described in France Patent No. 2285886 to optical resolution, since the other enantiomer cannot be to efficiently converted the racemate or the reverse enantiomer due to its chemical structure, the other enantiomer generally unnecessary cannot be reused for resolution and has to be disposed. Therefore, the yield of the optical resolution of the 2-aryl-substituted morpholine compound theoretically cannot achieve a yield exceeding 50%, and this method is synthetically and industrially highly disadvantageous. Accordingly, the present invention aims at providing a novel and efficient production method of an optically active 2-aryl-substituted morpholine compound useful as an intermediate for synthesizing a pharmaceutical agent, and a novel compound obtained thereby.

The present invention also aims at providing an industrially advantageous production method of 3-oxo-3-(pyrimidin-4-yl)propionate useful as an intermediate for synthesizing a pharmaceutical agent.

The present inventors have conducted intensive studies in an attempt to solve the aforementioned problems and found an efficient production method of an optically active 2-aryl-substituted morpholine compound via an optically active 2-ethanolamine compound, which resulted in the completion of the present invention.

Accordingly, the present invention provides a production method of an optically active 2-ethanolamine compound, an optically active 2-ethanolamine compound obtained thereby, a production method of an optically active 2-aryl-substituted morpholine compound from the optically active 2-ethanolamine compound, and an optically active 2-aryl-substituted morpholine compound obtained thereby. The detail is as described below.

The present invention provides a production method of an optically active compound represented by the formula 5, which comprises the following steps:

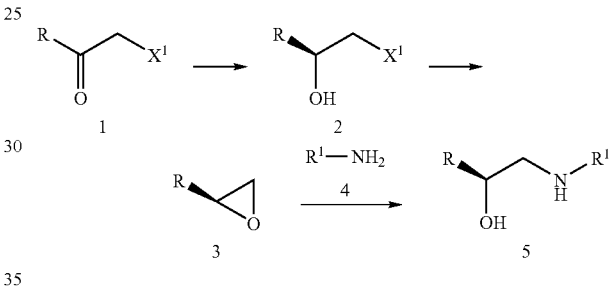

wherein R is an aryl optionally having substituent(s) or a heteroaryl optionally having substituent(s), $X^1$ is a halogen, and $R^1$ is a $C_1$-$C_6$ alkyl, an aralkyl optionally having substituent(s) or a $C_2$-$C_6$ alkenyl, step 1) reacting a compound of the formula 1 with a borane or a complex thereof in a solvent in the presence of (S)-2-methyl-CBS-oxazaborolidine to give a compound of the formula 2, step 2) reacting the compound of the formula 2 with a base in a solvent to give a compound of the formula 3, and step 3) reacting the compound of the formula 3 with an amine of the formula 4 to give the compound of the formula 5.

The present invention also provides a production method of an optically active morpholine compound represented by the formula 10, which comprises the following steps:

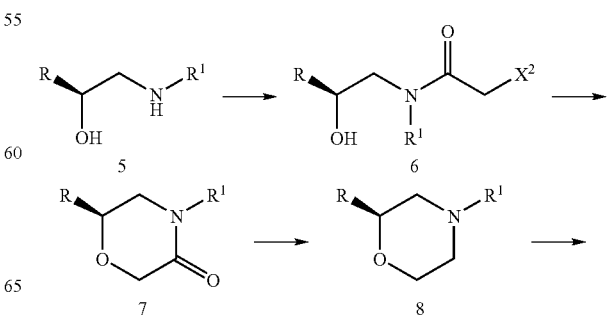

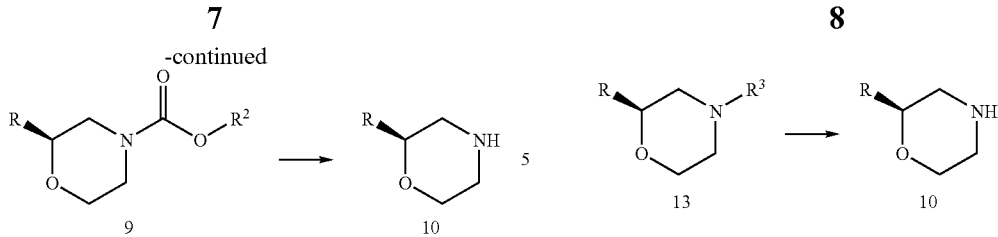

wherein R is an aryl optionally having substituent(s) or a heteroaryl optionally having substituent(s), $R^1$ is a $C_1$-$C_6$ alkyl, an aralkyl optionally having substituent(s) or a $C_2$-$C_6$ alkenyl, $R^2$ is a $C_1$-$C_6$ alkyl, a $C_1$-$C_6$ haloalkyl, an aryl optionally having substituent(s) or a benzyl optionally having substituent(s), and $X^2$ is a halogen, step 1) reacting a compound of the formula 5 with an activated chloroacetic acid or bromoacetic acid in a solvent to give a compound of the formula 6, step 2) reacting the compound of the formula 6 with a base to give a compound of the formula 7, step 3) reacting the compound of the formula 7 with a reducing agent in a solvent to give a compound of the formula 8, step 4) reacting the compound of the formula 8 with a chloroformate to give a compound of the formula 9, and step 5) subjecting the compound of the formula 9 to hydrolysis to give the compound of the formula 10.

The present invention further provides an optically active compound represented by the formula 11:

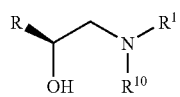

wherein R is an aryl optionally having substituent(s) or a heteroaryl optionally having substituent(s), $R^1$ is a $C_1$-$C_6$ alkyl, an aralkyl optionally having substituent(s) or a $C_2$-$C_6$ alkenyl, and $R^{10}$ is a hydrogen atom or a group represented by the formula: —CO—$CH_2$—$X^2$ (wherein $X^2$ is a halogen), or a salt thereof.

The present invention moreover provides an optically active morpholine compound represented by the formula 12:

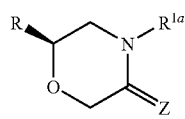

wherein R is an aryl optionally having substituent(s) or a heteroaryl optionally having substituent(s), $R^{1a}$ is a hydrogen atom, a $C_1$-$C_6$ alkyl, an aralkyl optionally having substituent(s), a $C_2$-$C_6$ alkenyl or a group represented by the formula: —$COOR^2$ (wherein $R^2$ is a $C_1$-$C_6$ alkyl, a $C_1$-$C_6$ haloalkyl, an aryl optionally having substituent(s) or a benzyl optionally having substituent(s)), and Z is O or $H_2$, provided that when $R^{1a}$ is a hydrogen atom and Z is $H_2$, then R should not be a 4-fluorophenyl, or a salt thereof.

The present invention also provides a production method of an optically active morpholine compound represented by the formula 10, which comprises reacting a compound of the formula 13 with hydrogen in the presence of a transition metal catalyst:

wherein R is an aryl optionally having substituent(s) or a heteroaryl optionally having substituent(s), and $R^3$ is a benzyl optionally having substituent(s), a 1-phenylethyl optionally having substituent(s) or a benzyloxycarbonyl optionally having substituent(s).

The present invention further provides a production method of an optically active compound represented by the formula 25, which comprises the following steps:

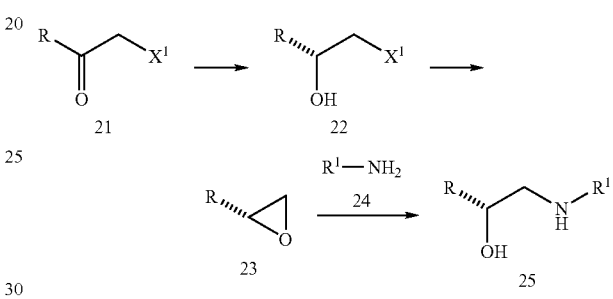

wherein R is an aryl optionally having substituent(s) or a heteroaryl optionally having substituent(s), $X^1$ is a halogen, and $R^1$ is a $C_1$-$C_6$ alkyl, an aralkyl optionally having substituent(s) or a $C_2$-$C_6$ alkenyl, step 1) reacting a compound of the formula 21 with a borane or a complex thereof in a solvent in the presence of (R)-2-methyl-CBS-oxazaborolidine to give a compound of the formula 22, step 2) reacting the compound of the formula 22 with a base in a solvent to give a compound of the formula 23, and step 3) reacting the compound of the formula 23 with an amine of the formula 24 to give the compound of the formula 25.

The present invention moreover provides a production method of an optically active morpholine compound represented by the formula 30, which comprises the following steps:

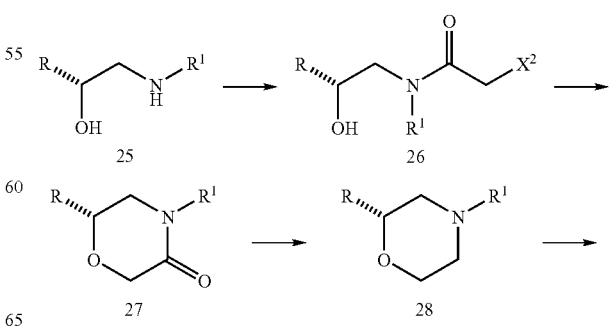

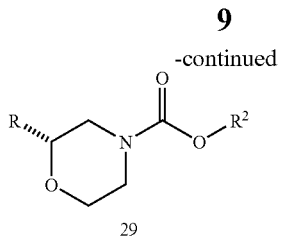

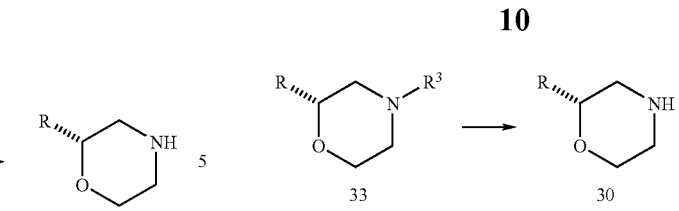

wherein R is an aryl optionally having substituent(s) or a heteroaryl optionally having substituent(s), $R^1$ is a $C_1$-$C_6$ alkyl, an aralkyl optionally having substituent(s) or a $C_2$-$C_6$ alkenyl, $R^2$ is a $C_1$-$C_6$ alkyl, a $C_1$-$C_6$ haloalkyl, an aryl optionally having substituent(s) or a benzyl optionally having substituent(s), and $X^2$ is a halogen, step 1) reacting a compound of the formula 25 with an activated chloroacetic acid or bromoacetic acid in a solvent to give a compound of the formula 26, step 2) reacting the compound of the formula 26 with a base to give a compound of the formula 27, step 3) reacting the compound of the formula 27 with a reducing agent in a solvent to give a compound of the formula 28, step 4) reacting the compound of the formula 28 with a chloroformate to give a compound of the formula 29, and step 5) subjecting the compound of the formula 29 to hydrolysis to give the compound of the formula 30.

The present invention also provides an optically active compound represented by the formula 31:

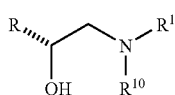

wherein R is an aryl optionally having substituent(s) or a heteroaryl optionally having substituent(s), $R^1$ is a $C_1$-$C_6$ alkyl, an aralkyl optionally having substituent(s) or a $C_2$-$C_6$ alkenyl, and $R^{10}$ is a hydrogen atom or a group represented by the formula: —CO—CH$_2$—X$^2$ (wherein X$^2$ is a halogen), or a salt thereof.

The present invention further provides an optically active morpholine compound represented by the formula 32:

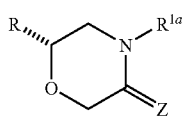

wherein R is an aryl optionally having substituent(s) or a heteroaryl optionally having substituent(s), $R^{1a}$ is a hydrogen atom, a $C_1$-$C_6$ alkyl, an aralkyl optionally having substituent(s), a $C_2$-$C_6$ alkenyl or a group represented by the formula: —COOR$^2$ (wherein $R^2$ is a $C_1$-$C_6$ alkyl, a $C_1$-$C_6$ haloalkyl, an aryl optionally having substituent(s) or a benzyl optionally having substituent(s)), and Z is O or H$_2$, provided that when $R^{1a}$ is a hydrogen atom and Z is H$_2$, then R should not be a 4-fluorophenyl, or a salt thereof.

The present invention moreover provides a production method of an optically active morpholine compound represented by the formula 30, which comprises reacting a compound of the formula 33 with hydrogen in the presence of a transition metal catalyst:

wherein R is an aryl optionally having substituent(s) or a heteroaryl optionally having substituent(s), and $R^3$ is a benzyl optionally having substituent(s), a 1-phenylethyl optionally having substituent(s) or a benzyloxycarbonyl optionally having substituent(s).

Further, the present invention provides a production method of an optically active compound represented by the formula 35, which comprises reacting a compound of the formula 34 with isopropanol or formic acid in the presence of a ruthenium catalyst (hereinafter to be also referred to as Ru catalyst) and an optically active amino alcohol or amine ligand:

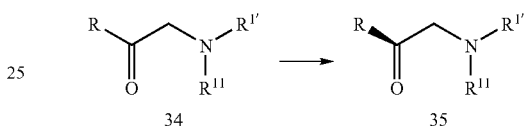

wherein R is an aryl optionally having substituent(s) or a heteroaryl optionally having substituent(s), $R^{1'}$ is a hydrogen atom, a $C_1$-$C_6$ alkyl, an aralkyl optionally having substituent(s) or a $C_2$-$C_6$ alkenyl, and $R^{11}$ is a hydrogen atom or a tert-butoxycarbonyl group.

The present invention further provides a compound represented by the formula 34:

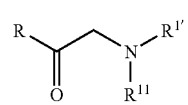

wherein R is an aryl optionally having substituent(s) or a heteroaryl optionally having substituent(s), $R^{1'}$ is a hydrogen atom, a $C_1$-$C_6$ alkyl, an aralkyl optionally having substituent(s) or a $C_2$-$C_6$ alkenyl, and $R^{11}$ is a hydrogen atom or a tert-butoxycarbonyl group, or a salt thereof.

The present invention moreover provides a production method of an optically active compound represented by the formula 36, which comprises reacting a compound of the formula 34 with isopropanol or formic acid in the presence of a Ru catalyst and an optically active amino alcohol or amine ligand:

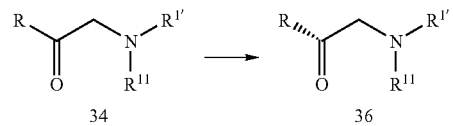

wherein R is an aryl optionally having substituent(s) or a heteroaryl optionally having substituent(s), $R^1$ is a hydrogen atom, a $C_1$-$C_6$ alkyl, an aralkyl optionally having substituent(s) or a $C_2$-$C_6$ alkenyl, and $R^{11}$ is a hydrogen atom or a tert-butoxycarbonyl group.

The present invention also provides a production method of an optically active compound represented by the formula (I), which comprises any one of the above-mentioned methods:

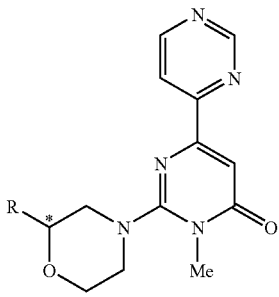
(I)

wherein R is an aryl optionally having substituent(s) or a heteroaryl optionally having substituent(s), and a carbon atom marked with * is an asymmetric carbon atom.

The present invention further provides a production method of an optically active compound represented by the formula (I), which comprises use of any one of the above-mentioned compounds:

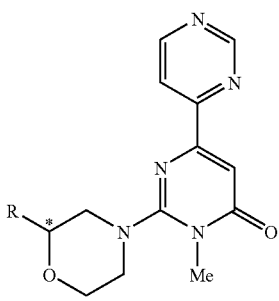
(I)

wherein R is an aryl optionally having substituent(s) or a heteroaryl optionally having substituent(s), and a carbon atom marked with * is an asymmetric carbon atom.

Moreover, the present inventors have conducted intensive studies in an attempt to solve the aforementioned problems and found a highly efficient production method of 3-oxo-3-(pyrimidin-4-yl)propionate, which resulted in the completion of the present invention.

Accordingly, the present invention provides a production method of a compound represented by the formula 55, which comprises the following steps:

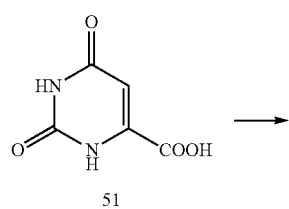

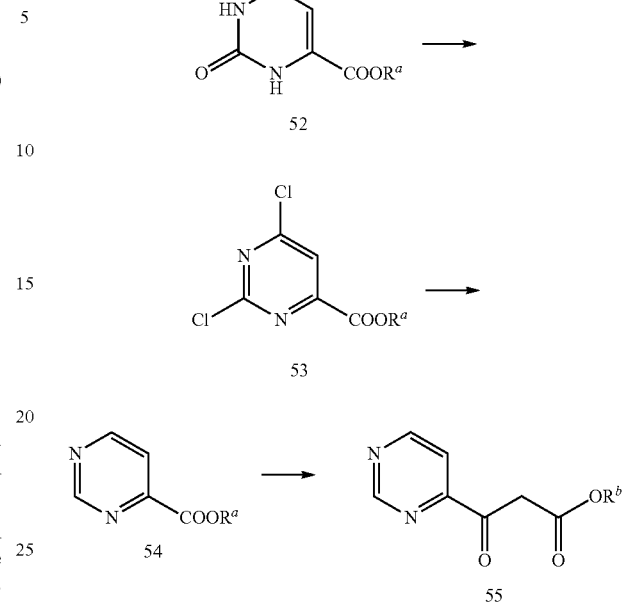

wherein $R^a$ and $R^b$ are the same or different and each is a $C_{1-6}$ alkyl, step 1) reacting orotic acid of the formula 51 with an alkylating agent in a solvent in the presence of a base to give a compound of the formula 52, step 2) heating the compound of the formula 52 under reflux with a chlorinating agent to give a compound of the formula 53, step 3) dechlorinating the compound of the formula 53 in the presence of a base to give a compound of the formula 54, and step 4) reacting the compound of the formula 54 with an acetate in the presence of a base to give the compound of the formula 55.

The present invention also provides a production method of a compound represented by the formula 52, which comprises reacting orotic acid of the formula 51 with an alkylating agent in a solvent in the presence of a base:

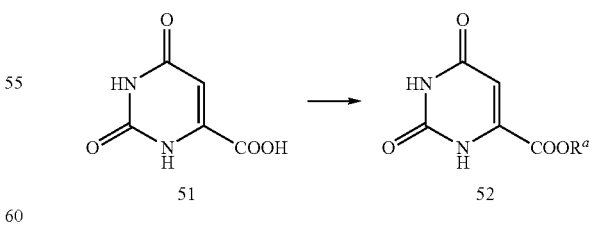

wherein $R^a$ is a $C_{1-6}$ alkyl.

The present invention further provides a production method of a compound represented by the formula 53, which comprises heating a compound of the formula 52 under reflux with a chlorinating agent:

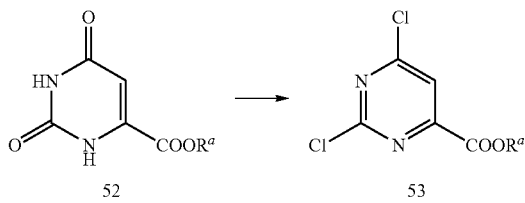

wherein $R^a$ is a $C_{1-6}$ alkyl.

The present invention moreover provides a production method of a compound represented by the formula 54, which comprises dechlorinating a compound of the formula 53 in the presence of a base:

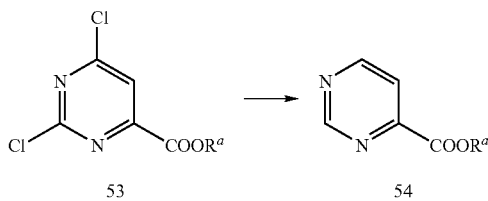

wherein $R^a$ is a $C_{1-6}$ alkyl.

According to the production method of the present invention, an optically active 2-aryl-substituted morpholine compound and 3-oxo-3-(pyrimidin-4-yl)propionate, which are important as starting materials for synthesizing compounds such as 2-(2-arylmorpholin-4-yl)-1-methyl-1H-[4,4']bipyrimidinyl-6-one and the like having a tau protein kinase 1 inhibitory activity and useful as a therapeutic drug for Alzheimer's disease and the like, can be produced in a high yield by an industrially advantageous method.

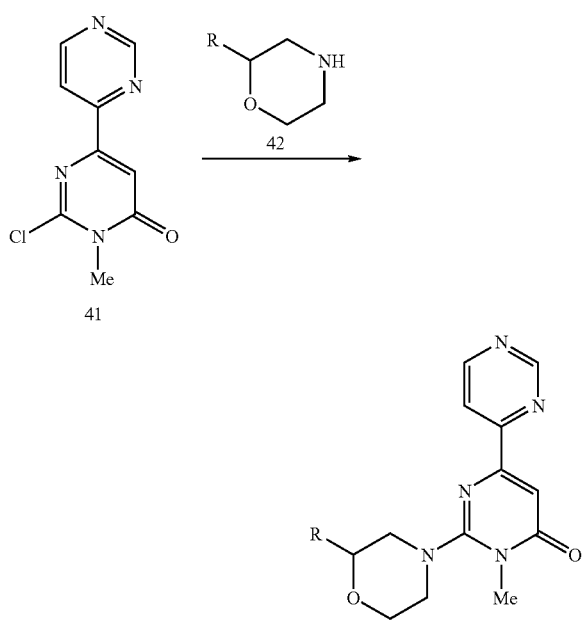

BEST MODE FOR EMBODYING THE INVENTION

The invention is explained in detail in the following.

In this specification, the aryl is an aryl having 6 to 10 carbon atoms, and, for example, phenyl, naphthyl and the like can be mentioned.

As the heteroaryl, for example, furyl, thienyl, pyridyl, pyrimidinyl, pyridazinyl, pyrazinyl and the like can be mentioned.

The halogen is chlorine, bromine, iodine or fluorine.

The $C_1$-$C_6$ alkyl is a straight chain or branched chain alkyl having 1 to 6 carbon atoms, and, for example, methyl, ethyl, propyl, isopropyl, butyl, secondary butyl, tertiary butyl, pentyl, hexyl and the like can be mentioned.

The $C_1$-$C_6$ haloalkyl is a straight chain or branched chain alkyl having 1 to 6 carbon atoms substituted by halogen, and, for example, chloromethyl, 1-chloroethyl, 2-chloroethyl, 1-chloropropyl, bromomethyl, 1-bromoethyl, 1-bromopropyl, 1-chlorobutyl and the like can be mentioned.

The aralkyl is a $C_1$-$C_4$ alkyl substituted by aryl, and, for example, benzyl, 2-phenylethyl, 1-phenylethyl, 3-phenylpropyl and the like can be mentioned.

The $C_2$-$C_6$ alkenyl is a straight chain or branched chain alkenyl group having 2 to 6 carbon atoms and, for example, vinyl, allyl (2-propenyl), 2-butenyl and the like can be mentioned.

In addition, the above-mentioned aryl, heteroaryl and aralkyl optionally have, on the ring, 1 to 5 substituents selected from halogen (chlorine, bromine, iodine, fluorine), $C_1$-$C_6$ alkyl (e.g., alkyl having 1 to 6 carbon atoms such as methyl, ethyl, propyl, isopropyl, butyl, secondary butyl, tertiary butyl and the like), $C_1$-$C_6$ alkoxy (e.g., alkoxy having 1 to 6 carbon atoms such as methoxy, ethoxy, propoxy, isopropoxy, butoxy, secondary butoxy, tertiary butoxy and the like), hydroxyl group, nitro, amino, cyano, aminoalkoxy (alkoxy substituted by primary, secondary or cyclic amine), aralkyloxy (e.g., $C_1$-$C_6$ alkoxy substituted by aryl, such as benzyloxy, 2-phenylethyloxy, 1-phenylethyloxy and the like), $C_1$-$C_6$ alkylsulfonyloxy (e.g., alkylsulfonyloxy having 1 to 6 carbon atoms such as methanesulfonyloxy, ethanesulfonyloxy and the like), arylsulfonyloxy (e.g., arylsulfonyloxy having 6 to 10 carbon atoms such as benzenesulfonyloxy, naphthalenesulfonyloxy and the like) and $C_1$-$C_6$ alkyl-substituted arylsulfonyloxy (e.g., arylsulfonyloxy substituted by $C_1$-$C_6$ alkyl, such as toluenesulfonyloxy and the like).

The $C_1$-$C_6$ alkyl and $C_1$-$C_6$ alkoxy, which are substituents for the aryl, heteroaryl and aralkyl, optionally have 1 to 3 substituents selected from halogen (chlorine, bromine, iodine, fluorine), hydroxyl group, nitro, amino and cyano.

In this specification, the salt includes a salt with inorganic acid (hydrochloric acid, hydrobromic acid, sulfuric acid, phosphoric acid, nitric acid and the like) or organic acid (acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, camphorsulfonic acid, ascorbic acid and the like).

In the present invention, an optically active 2-aryl-substituted morpholine compound can be produced via an optically active 2-ethanolamine compound. First, the production of the 2-ethanolamine compound is explained.

An optically active 2-ethanolamine compound can be produced according to the following Scheme 1 (S-form) or Scheme 2 (R-form).

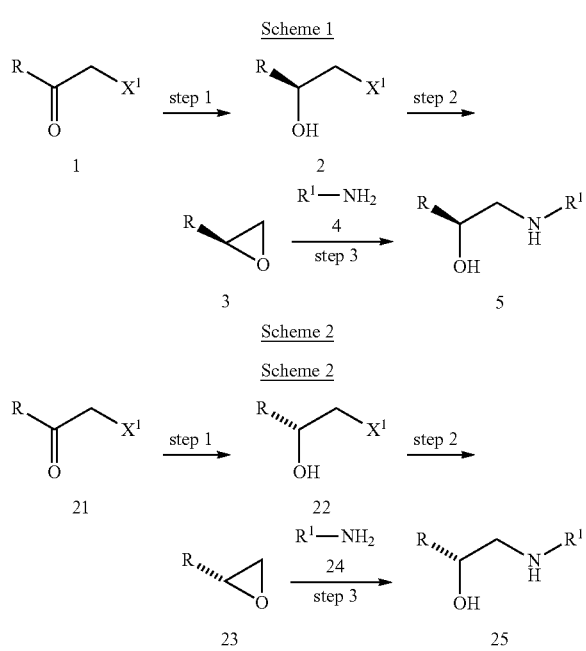

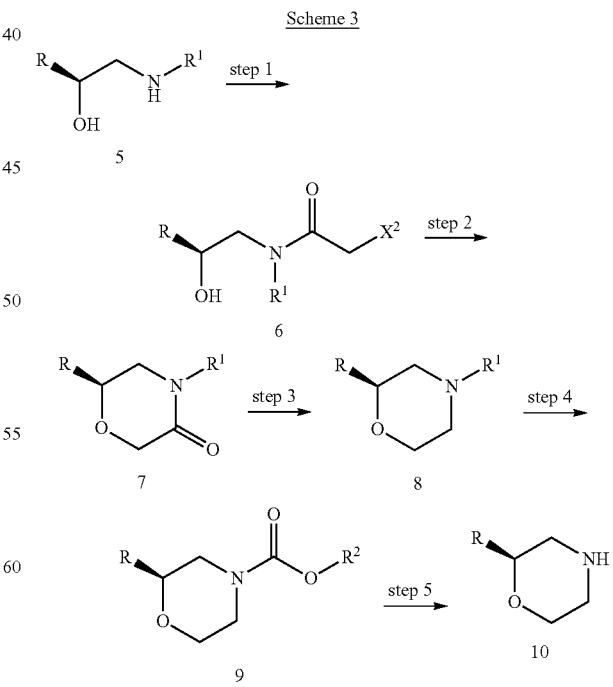

wherein the symbols in each scheme are as defined above.

Scheme 1 is explained below.

In the step 1, a compound of the formula 2 is obtained by reacting a compound of the formula 1 with a borane or a complex thereof in a solvent in the presence of (S)-2-methyl-CBS-oxazaborolidine.

As the borane and complex thereof, for example, borane-ammonia complex, borane-tert-butylamine complex, borane-N,N-diethylaniline complex, borane-N,N-diisopropylethylamine complex, borane-dimethylamine complex, borane-dimethylsulfide complex, borane-diphenylphosphine complex, borane-isoamylsulfide complex, borane-4-methylmorpholine complex, borane-morpholine complex, borane-pyridine complex, borane-tetrahydrofuran complex, borane-triethylamine complex, borane-trimethylamine complex, borane-triphenylphospine complex, borane-tributylphosphine complex, borane-4-ethylmorpholine complex, borane-1,4-oxathiane complex, borane-di-tert-butylphosphine complex, borane-dicyclohexylphosphine complex, borane-di-tert-butylchlorophosphine complex, borane-phenylphosphine complex, borane-methylphosphine complex, borane-tert-butylphenylphosphine complex, catecholborane and the like can be mentioned.

The amount of the borane and complex thereof to be used is generally 0.1 mol to 100 mol, preferably 1 mol to 2 mol, relative to 1 mol of the compound of the formula 1.

The amount of the (S)-2-methyl-CBS-oxazaborolidine to be used is generally 0.01 mol to 10 mol, preferably 0.05 mol to 1 mol, relative to 1 mol of the compound of the formula 1.

As the solvent, for example, tetrahydrofuran, toluene, dichloromethane, diethyl ether, a mixture thereof and the like can be mentioned.

This step proceeds at −80° C. to 100° C., preferably −30° C. to 0° C. for 0.1 hr to 10 hrs.

In the step 2, a compound of the formula 3 is obtained by reacting the compound of the formula 2 with a base in a solvent.

As the base, for example, lithium hydroxide, sodium hydroxide, potassium hydroxide, sodium carbonate, potassium carbonate, sodium methoxide, sodium ethoxide, sodium tert-butoxide, potassium tert-butoxide, sodium hydride, triethylamine, 1,8-diazabicyclo[5,4,0]undec-7-ene, n-butyllithium and the like can be mentioned.

The amount of the base to be used is generally 1 mol to 10 mol, preferably 1 mol to 3 mol, relative to 1 mol of the compound of the formula 2.

As the solvent, for example, methanol, ethanol, isopropanol, tert-butanol, hexane, chloroform, dichloromethane, dimethylsulfoxide, N,N-dimethylformamide, acetonitrile, water, tetrahydrofuran, diethyl ether, 1,4-dioxane, acetone, N-methylpyrrolidone, pentane, a mixed solvent thereof and the like can be mentioned.

This step proceeds at 0° C. to 100° C. for 0.1 hr to 10 hrs.

In the step 3, a compound of the formula 5 is obtained by reacting the compound of the formula 3 with an amine of the formula 4.

The amount of the amine of the formula 4 to be used is generally 1 mol to 10 mol, preferably 1 mol to 5 mol, relative to 1 mol of the compound of the formula 3.

This step proceeds at 50° C. to 150° C. for 0.1 hr to 50 hrs.

By these steps, a 2-ethanolamine compound (S-form), which is the compound of the formula 5, can be produced.

Scheme 2 can be performed by the steps similar to those in Scheme 1 except that (R)-2-methyl-CBS-oxazaborolidine is used in step 1 instead of (S)-2-methyl-CBS-oxazaborolidine, whereby a 2-ethanolamine compound (R-form), which is the compound of the formula 25, can be produced.

Using the thus produced optically active 2-ethanolamine compound (the compound of the formula 5 or the compound of the formula 25), an optically active 2-aryl-substituted morpholine compound can be produced according to the following Scheme 3 (S-form) or Scheme 4 (R-form).

-continued
Scheme 4

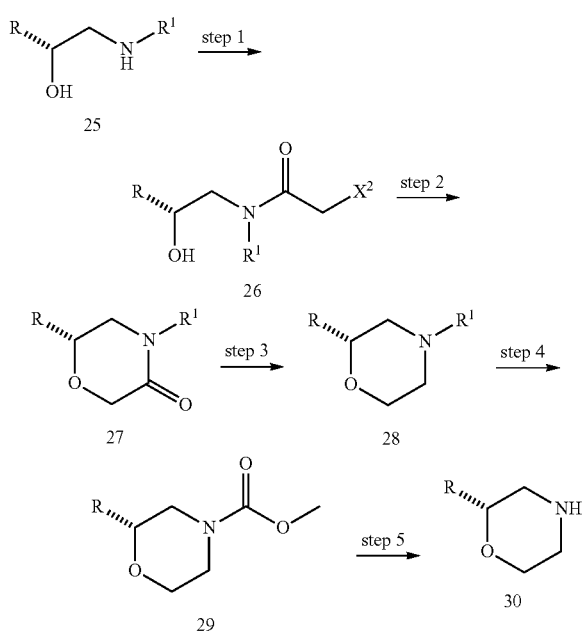

wherein the symbols in each scheme are as defined above.

Scheme 3 is explained below.

In the step 1, a compound of the formula 6 is obtained by reacting the compound of the formula 5 with an activated chloroacetic acid or bromoacetic acid in a solvent.

As the activated chloroacetic acid or bromoacetic acid, for example,
acid anhydrides such as chloroacetic anhydride, bromoacetic anhydride and the like;
acid halides such as chloroacetyl chloride, chloroacetyl bromide, bromoacetyl chloride, bromoacetyl bromide and the like;
mixed acid anhydrides with sulfonic acids such as methanesulfonic acid, toluenesulfonic acid and the like;
mixed acid anhydrides with chloroformates such as isobutyl chloroformate and the like;
activated esters such as 4-nitrophenyl chloroacetate, 4-nitrophenyl bromoacetate, benzotriazol-1-yl chloroacetate, benzotriazol-1-yl bromoacetate, 3,5-dioxo-4-azatricyclo[5.2.1.0$^{2,6}$]dec-8-en-4-yl chloroacetate, 3,5-dioxo-4-azatricyclo[5.2.1.0$^{2,6}$]dec-8-en-4-yl bromoacetate, 1,3-dioxo-1,3-dihydroisoindol-2-yl chloroacetate, 1,3-dioxo-1,3-dihydroisoindol-2-yl bromoacetate, 2,5-dioxopyrrolidin-1-yl chloroacetate, 2,5-dioxopyrrolidin-1-yl bromoacetate, [1,2,3]triazolo[4,5-b]pyridin-3-yl chloroacetate, [1,2,3]triazolo[4,5-b]pyridin-3-yl bromoacetate and the like;
chloroacetic acids or bromoacetic acids activated with activating agents for carboxylic acid, such as 1H-benzotriazol-1-yloxytripyrrolidinophosphonium hexafluorophosphate, 1H-benzotriazol-1-yloxytris(dimethylamino)phosphonium hexafluorophosphate, O-(benzotriazol-1-yl)-N,N,N',N'-tetramethyluronium hexafluorophosphate, O-(benzotriazol-1-yl)-N,N,N',N'-tetramethyluronium tetrafluoroborate, bis(2-oxo-3-oxazolidinyl)phosphinic chloride, 2-bromo-1-ethylpyridinium tetrafluoroborate, N-carbobenzoxyoxysuccinimide, 2-bromobenzyl succinimidyl carbonate, di-2-pyridyl carbonate, 2,2'-carbonylbis(3,5-dioxo-4-methyl-1,2,4-oxadiazolidine), 1,1'-carbonylbis-1H-imidazole, N-(2-chlorobenzyloxycarbonyloxy)succinimide, (4R,5R)-2-chloro-1,3-dimethyl-4,5-diphenyl-1-imidazolinium chloride, (4S,5S)-2-chloro-1,3-dimethyl-4,5-diphenyl-1-imidazolinium chloride, 2-chloro-1,3-dimethylimidazolinium chloride, 2-chloro-1,3-dimethylimidazolinium hexafluorophosphate, 2-chloro-3-ethylbenzoxazolium tetrafluoroborate, 2-chloro-1-methylpyridinium iodide, 2-chloro-1-methylpyridinium p-toluenesulfonate, 1-(chloro-1-pyrrolidinylmethylene)pyrrolidinium hexafluorophosphate, 1-(chloro-1-pyrrolidinylmethylene)pyrrolidinium tetrafluoroborate, cyanomethylenetri-n-butylphosphorane, 1-cyclohexyl-3-(2-morpholinoethyl)carbodiimide metho-p-toluenesulfonate, N,N'-dicyclohexylcarbodiimide, diphenyl (2,3-dihydro-2-thioxo-3-benzoxazolyl)phosphonate, N,N'-diisopropylcarbodiimide, di(N-succinimidyl) carbonate, 1-ethoxycarbonyl-2-ethoxy-1,2-dihydroquinoline, 1-ethyl-3-(3-dimethylaminopropyl)carbodiimide hydrochloride, 2-fluoro-1-methylpyridinium p-toluenesulfonate, 1-(4-nitrobenzenesulfonyl)-1H-1,2,4-triazole, 2-(5-norbornene-2,3-dicarboximido)-1,1,3,3-tetramethyluronium tetrafluoroborate, μ-oxo-bis[tris(dimethylamino)phosphonium]bis(tetrafluoroborate), N-(1,2,2,2-tetrachloroethoxycarbonyloxy)succinimide, 1-(p-toluenesulfonyl)imidazole, pentachlorophenyl trichloroacetate, 4-nitrophenyl trifluoroacetate and the like, can be mentioned.

The amount of the activated chloroacetic acid or bromoacetic acid to be used is generally 1 mol to 10 mol, preferably 1 mol to 2 mol, relative to 1 mol of the compound of the formula 5.

As the solvent, for example, dichloromethane, 1,2-dichloroethane, 1,1,1-trichloroethane, chloroform, carbon tetrachloride, 1,2-dichlorobenzene, ethyl acetate, butyl acetate, isopropyl acetate, acetonitrile, propionitrile, tetrahydrofuran, 1,4-dioxane, diethyl ether, 1,2-dimethoxyethane, isopropyl ether, benzene, toluene, xylene, water, ethanol, methanol, isopropanol, a mixed solvent thereof and the like can be me mentioned.

This step proceeds at −10° C. to 60° C. for 0.1 hr to 10 hrs.

In the step 2, a compound of the formula 7 is obtained by reacting the compound of the formula 6 with a base.

As the base, for example, lithium hydroxide, sodium hydroxide, potassium hydroxide, sodium carbonate, potassium carbonate, sodium methoxide, sodium ethoxide, sodium tert-butoxide, potassium tert-butoxide, sodium hydride and the like can be mentioned.

The amount of the base to be used is generally 1 mol to 10 mol, preferably 1 mol to 3 mol, relative to 1 mol of the compound of the formula 6.

This step can be carried out in a solvent, and as the solvent, for example, isopropyl alcohol, toluene, a mixed solvent thereof and the like can be me mentioned.

This step proceeds at 0° C. to 100° C. for 0.1 hr to 10 hrs.

After the completion of the reaction of step 1, step 2 may be sequentially performed without work-up.

In the step 3, a compound of the formula 8 is obtained by reacting the compound of the formula 7 with a reducing agent in a solvent.

As the reducing agent, for example, lithium aluminum hydride, sodium bis(2-methoxyethoxy)aluminum hydride, lithium borohydride, sodium borohydride, potassium borohydride, borane and complex thereof (e.g., borane-ammonia complex, borane-tert-butylamine complex, borane-N,N-diethylaniline complex, borane-N,N-diisopropylethylamine complex, borane-dimethylamine complex, borane-dimethylsulfide complex, borane-diphenylphosphine complex, borane-isoamylsulfide complex, borane-4-methylmorpholine complex, borane-morpholine complex, borane-pyridine complex, borane-tetrahydrofuran complex, borane-triethylamine complex, borane-trimethylamine complex, borane-triphenylphospine complex, borane-tributylphosphine complex, borane-4-ethylmorpholine complex, borane-1,4-oxathiane complex, borane-di-tert-butylphosphine complex, borane-dicyclohexylphosphine complex, borane-di-tert-butylchlorophosphine complex, borane-phenylphosphine complex, borane-methylphosphine complex, borane-tert-butylphenylphosphine complex) and the like can be mentioned. Such reducing agent may be used together with an inorganic reagent such as iodine, sulfuric acid, lithium halide, boron trifluoride etherate, chlorotrimethylsilane and the like.

The amount of the reducing agent to be used is generally 1 mol to 10 mol, preferably 1 mol to 3 mol, relative to 1 mol of the compound of the formula 7.

As the solvent, for example, ether solvents such as tetrahydrofuran, methyltetrahydrofuran, dimethoxyethane, diglyme and the like; hydrocarbon solvents such as toluene, xylene and the like; a mixed solvent thereof and the like can be mentioned.

This step proceeds at 0° C. to 120° C. for 0.5 hr to 10 hrs.

In the step 4, a compound of the formula 9 is obtained by reacting the compound of the formula 8 with a chloroformate.

As the chloroformate, for example, $C_1$-$C_6$ alkyl chloroformates such as methyl chloroformate, ethyl chloroformate and the like; $C_1$-$C_6$ haloalkyl chloroformates such as 1-chloroethyl chloroformate and the like; aryl chloroformates (wherein the aryl moiety optionally has substituent(s)); benzyl chloroformates (wherein the benzyl moiety optionally has substituent(s)) and the like can be mentioned.

The amount of the chloroformate to be used is generally 1 mol to 10 mol, preferably 1 mol to 5 mol, relative to 1 mol of the compound of the formula 8.

This step can be carried out in a solvent, and as the solvent, for example, dichloroethane, dichloromethane, benzene, toluene, xylene, chloroform, chlorobenzene, ethyl acetate, acetone, a mixed solvent thereof and the like can be mentioned. In addition, this step can be carried out in the presence of an additive such as sodium iodide, potassium iodide, lithium iodide and the like.

This step proceeds at 0° C. to 180° C. for 0.5 hr to 100 hrs.

In the step 5, a compound of the formula 10 is obtained by subjecting the compound of the formula 9 to hydrolysis.

The hydrolysis is carried out using an acid or alkali. As the acid, for example, hydrochloric acid and the like can be mentioned. As the alkali, for example, sodium hydroxide, potassium hydroxide and the like can be mentioned.

The amount of the acid or alkali to be used is generally 1 mol to 50 mol, preferably 1 mol to 10 mol, relative to 1 mol of the compound of the formula 9.

This step can be carried out in a solvent, and as the solvent, for example, methanol, ethanol, a mixed solvent thereof and the like can be mentioned.

This step proceeds at 20° C. to 150° C. for 0.5 hr to 50 hrs.

When $R^2$ is a 1-chloroethyl, the hydrolysis can be carried out by heating the compound of the formula 9 in an alcohol such as methanol, ethanol and the like, at 50° C. to 100° C. for 0.1 hr to 10 hrs.

By these steps, a 2-aryl-substituted morpholine compound (S-form), which is the compound of the formula 10, can be produced.

Scheme 4 can be performed by the steps similar to those in Scheme 3 except that a compound of the formula 25 (R-form) is used in step 1 instead of the compound of the formula 5 (S-form), whereby a 2-aryl-substituted morpholine compound (R-form), which is the compound of the formula 30, can be produced.

In addition, an optically active 2-aryl-substituted morpholine compound can be also produced according to the following Scheme 5 (S-form) or Scheme 6 (R-form).

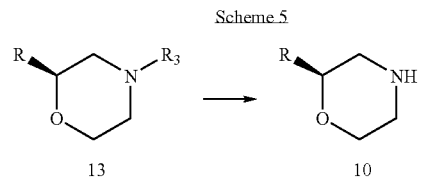

Scheme 5

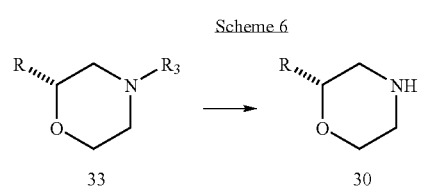

Scheme 6 wherein the symbols in each scheme are as defined above.

Scheme 5 is explained below.

In this step, the morpholine compound of the formula 10 is obtained by reacting a compound of the formula 13 with hydrogen in the presence of a transition metal catalyst.

As the transition metal catalyst, for example, catalysts containing palladium, nickel, platinum, rhodium or ruthenium can be mentioned. As representative examples, palladium carbon, palladium oxide, palladium black, palladium hydroxide, palladium-silica-alumina, palladium alumina, Raney-nickel, platinum carbon, platinum black, platinum oxide, platinum alumina, rhodium carbon, rhodium alumina, rhodium oxide, ruthenium oxide, ruthenium carbon, ruthenium black ruthenium alumina and the like can be mentioned.

The amount of the transition metal catalyst to be used is generally 0.001 mol to 10 mol, preferably 0.01 mol to 0.3 mol, relative to 1 mol of the compound of the formula 13.

As the solvent, for example, alcohol solvents (e.g., methanol, ethanol, isopropanol, propanol, butanol, tert-butanol), ether solvents (e.g., THF, dioxane, 1,2-dimethoxyethane, tert-butyl methyl ether), ester solvents (e.g., ethyl acetate, propyl acetate, methyl acetate, butyl acetate, isopropyl acetate), water, a mixed solvent thereof and the like can be mentioned.

This step proceeds at 0° C. to 100° C. for 0.5 hr to 100 hrs.

By this step, a 2-aryl-substituted morpholine compound (S-form), which is the compound of the formula 10, can be produced.

Scheme 6 can be performed by the steps similar to that in Scheme 5 except that a compound of the formula 33 (R-form) is used instead of the compound of the formula 13 (S-form), whereby a 2-aryl-substituted morpholine compound (R-form), which is a compound of the formula 30, can be produced.

Moreover, the compounds of the formula 10 and 30 can be produced as hydrochlorides thereof according to the established procedure via a reaction with hydrochloric acid.

The compound of the formula 5, which is an optically active 2-ethanolamine compound (S-form) produced in Scheme 1, as well as the compound of the formula 6, which is produced from the compound of the formula 5 in Scheme 3, are novel compounds (these compounds are collectively shown as the following compounds of the formula 11):

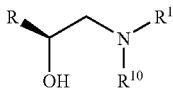

wherein each symbol is as defined above.

Of the above-mentioned compounds, a compound wherein R is a phenyl having 1 to 3 substituents selected from halogen, $C_1$-$C_6$ alkyl, substituted $C_1$-$C_6$ alkyl, $C_1$-$C_6$ alkoxy, substituted $C_1$-$C_6$ alkoxy, nitro aralkyloxy, $C_1$-$C_6$ alkylsulfonyloxy, arylsulfonyloxy and $C_1$-$C_6$ alkyl-substituted arylsulfonyloxy is preferable, and a compound wherein R is a phenyl having 1 to 3 substituents selected from fluorine, chlorine, bromine, nitro, benzyloxy, methanesulfonyloxy, benzenesulfonyloxy and toluenesulfonyloxy is more preferable. Specifically, the following compounds can be mentioned:

(1S)-1-(4-fluorophenyl)-2-(benzylamino)ethanol,
(1S)-1-(4-fluorophenyl)-2-(4-methoxybenzylamino)ethanol,
(1S)-1-(4-fluorophenyl)-2-(2,4-dimethoxybenzylamino)ethanol,
(1S)-1-(4-fluorophenyl)-2-((1R)-1-phenylethylamino)ethanol,
(1S)-1-(4-fluorophenyl)-2-((1S)-1-phenylethylamino)ethanol,
(1S)-1-(4-fluorophenyl)-2-(2-phenylethylamino)ethanol,
(1S)-1-(4-fluorophenyl)-2-(methylamino)ethanol,
(1S)-1-(4-fluorophenyl)-2-(ethylamino)ethanol,
(1S)-1-(4-fluorophenyl)-2-(tert-butylamino)ethanol,
(1S)-1-(4-fluorophenyl)-2-(allylamino)ethanol,
(1S)-1-(3-fluorophenyl)-2-(benzylamino)ethanol,
(1S)-1-(3-fluorophenyl)-2-(4-methoxybenzylamino)ethanol,
(1S)-1-(3-fluorophenyl)-2-(2,4-dimethoxybenzylamino)ethanol,
(1S)-1-(3-fluorophenyl)-2-((1R)-1-phenylethylamino)ethanol,
(1S)-1-(3-fluorophenyl)-2-((1S)-1-phenylethylamino)ethanol,
(1S)-1-(3-fluorophenyl)-2-(2-phenylethylamino)ethanol,
(1S)-1-(3-fluorophenyl)-2-(methylamino)ethanol,
(1S)-1-(3-fluorophenyl)-2-(ethylamino)ethanol,
(1S)-1-(3-fluorophenyl)-2-(tert-butylamino)ethanol,
(1S)-1-(3-fluorophenyl)-2-(allylamino)ethanol,
(1S)-1-(4-chlorophenyl)-2-(benzylamino)ethanol,
(1S)-1-(4-chlorophenyl)-2-(4-methoxybenzylamino)ethanol,
(1S)-1-(4-chlorophenyl)-2-(2,4-dimethoxybenzylamino)ethanol,
(1S)-1-(4-chlorophenyl)-2-((1R)-1-phenylethylamino)ethanol,
(1S)-1-(4-chlorophenyl)-2-((1S)-1-phenylethylamino)ethanol,
(1S)-1-(4-chlorophenyl)-2-(2-phenylethylamino)ethanol,
(1S)-1-(4-chlorophenyl)-2-(methylamino)ethanol,
(1S)-1-(4-chlorophenyl)-2-(ethylamino)ethanol,
(1S)-1-(4-chlorophenyl)-2-(tert-butylamino)ethanol,
(1S)-1-(4-chlorophenyl)-2-(allylamino)ethanol,
(1S)-1-(4-bromophenyl)-2-(benzylamino)ethanol,
(1S)-1-(4-bromophenyl)-2-(4-methoxybenzylamino)ethanol,
(1S)-1-(4-bromophenyl)-2-(2,4-dimethoxybenzylamino)ethanol,
(1S)-1-(4-bromophenyl)-2-((1R)-1-phenylethylamino)ethanol,
(1S)-1-(4-bromophenyl)-2-((1S)-1-phenylethylamino)ethanol,
(1S)-1-(4-bromophenyl)-2-(2-phenylethylamino)ethanol,
(1S)-1-(4-bromophenyl)-2-(methylamino)ethanol,
(1S)-1-(4-bromophenyl)-2-(ethylamino)ethanol,
(1S)-1-(4-bromophenyl)-2-(tert-butylamino)ethanol,
(1S)-1-(4-bromophenyl)-2-(allylamino)ethanol,
(1S)-1-(4-nitrophenyl)-2-(benzylamino)ethanol,
(1S)-1-(4-nitrophenyl)-2-(4-methoxybenzylamino)ethanol,
(1S)-1-(4-nitrophenyl)-2-(2,4-dimethoxybenzylamino)ethanol,
(1S)-1-(4-nitrophenyl)-2-((1R)-1-phenylethylamino)ethanol,
(1S)-1-(4-nitrophenyl)-2-((1S)-1-phenylethylamino)ethanol,
(1S)-1-(4-nitrophenyl)-2-(2-phenylethylamino)ethanol,
(1S)-1-(4-nitrophenyl)-2-(methylamino)ethanol,
(1S)-1-(4-nitrophenyl)-2-(ethylamino)ethanol,
(1S)-1-(4-nitrophenyl)-2-(tert-butylamino)ethanol,
(1S)-1-(4-nitrophenyl)-2-(allylamino)ethanol,
(1S)-1-(4-fluorophenyl)-2-(N-benzyl-N-chloroacetylamino)ethanol,
(1S)-1-(4-fluorophenyl)-2-(N-benzyl-N-bromoacetylamino)ethanol,
(1S)-1-(4-fluorophenyl)-2-(N-(1R)-1-phenylethyl-N-chloroacetylamino)ethanol,
(1S)-1-(4-fluorophenyl)-2-(N-(1S)-1-phenylethyl-N-chloroacetylamino)ethanol,
(1S)-1-(4-fluorophenyl)-2-(N-(1R)-1-phenylethyl-N-bromoacetylamino)ethanol,
(1S)-1-(4-fluorophenyl)-2-(N-(1S)-1-phenylethyl-N-bromoacetylamino)ethanol,
(1S)-1-(4-bromophenyl)-2-(N-benzyl-N-chloroacetylamino)ethanol,
(1S)-1-(4-bromophenyl)-2-(N-benzyl-N-bromoacetylamino)ethanol,
(1S)-1-(4-bromophenyl)-2-(N-(1R)-1-phenylethyl-N-chloroacetylamino)ethanol,
(1S)-1-(4-bromophenyl)-2-(N-(1S)-1-phenylethyl-N-chloroacetylamino)ethanol,
(1S)-1-(4-bromophenyl)-2-(N-(1R)-1-phenylethyl-N-bromoacetylamino)ethanol,
(1S)-1-(4-bromophenyl)-2-(N-(1S)-1-phenylethyl-N-bromoacetylamino)ethanol,
(1S)-1-(4-nitrophenyl)-2-(N-benzyl-N-chloroacetylamino)ethanol,
(1S)-1-(4-nitrophenyl)-2-(N-benzyl-N-bromoacetylamino)ethanol,
(1S)-1-(4-nitrophenyl)-2-(N-(1R)-1-phenylethyl-N-chloroacetylamino)ethanol,
(1S)-1-(4-nitrophenyl)-2-(N-(1S)-1-phenylethyl-N-chloroacetylamino)ethanol,
(1S)-1-(4-nitrophenyl)-2-(N-(1R)-1-phenylethyl-N-bromoacetylamino)ethanol,
(1S)-1-(4-nitrophenyl)-2-(N-(1S)-1-phenylethyl-N-bromoacetylamino)ethanol,
(1S)-1-(4-benzyloxyphenyl)-2-(benzylamino)ethanol,
(1S)-1-(4-benzyloxyphenyl)-2-(4-methoxybenzylamino)ethanol,
(1S)-1-(4-benzyloxyphenyl)-2-(2,4-dimethoxybenzylamino)ethanol,
(1S)-1-(4-benzyloxyphenyl)-2-((1R)-1-phenylethylamino)ethanol,
(1S)-1-(4-benzyloxyphenyl)-2-((1S)-1-phenylethylamino)ethanol,
(1S)-1-(4-benzyloxyphenyl)-2-(2-phenylethylamino)ethanol, (1S)-1-(4-benzyloxyphenyl)-2-(methylamino)ethanol,
(1S)-1-(4-benzyloxyphenyl)-2-(ethylamino)ethanol,
(1S)-1-(4-benzyloxyphenyl)-2-(tert-butylamino)ethanol,
(1S)-1-(4-benzyloxyphenyl)-2-(allylamino)ethanol,
(1S)-1-(4-benzyloxyphenyl)-2-(N-benzyl-N-chloroacetylamino)ethanol,
(1S)-1-(4-benzyloxyphenyl)-2-(N-benzyl-N-bromoacetylamino)ethanol,
(1S)-1-(4-benzyloxyphenyl)-2-(N-(1R)-1-phenylethyl-N-chloroacetylamino)ethanol,
(1S)-1-(4-benzyloxyphenyl)-2-(N-(1S)-1-phenylethyl-N-chloroacetylamino)ethanol,
(1S)-1-(4-benzyloxyphenyl)-2-(N-(1R)-1-phenylethyl-N-bromoacetylamino)ethanol,
(1S)-1-(4-benzyloxyphenyl)-2-(N-(1S)-1-phenylethyl-N-bromoacetylamino)ethanol,
(1S)-1-(4-methanesulfonyloxyphenyl)-2-(benzylamino)ethanol,
(1S)-1-(4-methanesulfonyloxyphenyl)-2-(4-methoxybenzylamino)ethanol,
(1S)-1-(4-methanesulfonyloxyphenyl)-2-(2,4-dimethoxybenzylamino)ethanol,
(1S)-1-(4-methanesulfonyloxyphenyl)-2-((1R)-1-phenylethylamino)ethanol,
(1S)-1-(4-methanesulfonyloxyphenyl)-2-((1S)-1-phenylethylamino)ethanol,
(1S)-1-(4-methanesulfonyloxyphenyl)-2-(2-phenylethylamino)ethanol,
(1S)-1-(4-methanesulfonyloxyphenyl)-2-(methylamino)ethanol,
(1S)-1-(4-methanesulfonyloxyphenyl)-2-(ethylamino)ethanol,
(1S)-1-(4-methanesulfonyloxyphenyl)-2-(tert-butylamino)ethanol,
(1S)-1-(4-methanesulfonyloxyphenyl)-2-(allylamino)ethanol,
(1S)-1-(4-methanesulfonyloxyphenyl)-2-(N-benzyl-N-chloroacetylamino)ethanol,
(1S)-1-(4-methanesulfonyloxyphenyl)-2-(N-benzyl-N-bromoacetylamino)ethanol,
(1S)-1-(4-methanesulfonyloxyphenyl)-2-(N-(1R)-1-phenylethyl-N-chloroacetylamino)ethanol,
(1S)-1-(4-methanesulfonyloxyphenyl)-2-(N-(1S)-1-phenylethyl-N-chloroacetylamino)ethanol,
(1S)-1-(4-methanesulfonyloxyphenyl)-2-(N-(1R)-1-phenylethyl-N-bromoacetylamino)ethanol,
(1S)-1-(4-methanesulfonyloxyphenyl)-2-(N-(1S)-1-phenylethyl-N-bromoacetylamino)ethanol,
(1S)-1-(4-benzenesulfonyloxyphenyl)-2-(benzylamino)ethanol,
(1S)-1-(4-benzenesulfonyloxyphenyl)-2-(4-methoxybenzylamino)ethanol,
(1S)-1-(4-benzenesulfonyloxyphenyl)-2-(2,4-dimethoxybenzylamino)ethanol,
(1S)-1-(4-benzenesulfonyloxyphenyl)-2-((1R)-1-phenylethylamino)ethanol,
(1S)-1-(4-benzenesulfonyloxyphenyl)-2-((1S)-1-phenylethylamino)ethanol,
(1S)-1-(4-benzenesulfonyloxyphenyl)-2-(2-phenylethylamino)ethanol,
(1S)-1-(4-benzenesulfonyloxyphenyl)-2-(methylamino)ethanol,
(1S)-1-(4-benzenesulfonyloxyphenyl)-2-(ethylamino)ethanol,
(1S)-1-(4-benzenesulfonyloxyphenyl)-2-(tert-butylamino)ethanol,
(1S)-1-(4-benzenesulfonyloxyphenyl)-2-(allylamino)ethanol,
(1S)-1-(4-benzenesulfonyloxyphenyl)-2-(N-benzyl-N-chloroacetylamino)ethanol,
(1S)-1-(4-benzenesulfonyloxyphenyl)-2-(N-benzyl-N-bromoacetylamino)ethanol,
(1S)-1-(4-benzenesulfonyloxyphenyl)-2-(N-(1R)-1-phenylethyl-N-chloroacetylamino)ethanol,
(1S)-1-(4-benzenesulfonyloxyphenyl)-2-(N-(1S)-1-phenylethyl-N-chloroacetylamino)ethanol,
(1S)-1-(4-benzenesulfonyloxyphenyl)-2-(N-(1R)-1-phenylethyl-N-bromoacetylamino)ethanol,
(1S)-1-(4-benzenesulfonyloxyphenyl)-2-(N-(1S)-1-phenylethyl-N-bromoacetylamino)ethanol,
(1S)-1-(4-(4-toluenesulfonyloxy)phenyl)-2-(benzylamino)ethanol,
(1S)-1-(4-(4-toluenesulfonyloxy)phenyl)-2-(4-methoxybenzylamino)ethanol,
(1S)-1-(4-(4-toluenesulfonyloxy)phenyl)-2-(2,4-dimethoxybenzylamino)ethanol,
(1S)-1-(4-(4-toluenesulfonyloxy)phenyl)-2-((1R)-1-phenylethylamino)ethanol,
(1S)-1-(4-(4-toluenesulfonyloxy)phenyl)-2-((1S)-1-phenylethylamino)ethanol,
(1S)-1-(4-(4-toluenesulfonyloxy)phenyl)-2-(2-phenylethylamino)ethanol,
(1S)-1-(4-(4-toluenesulfonyloxy)phenyl)-2-(methylamino)ethanol,
(1S)-1-(4-(4-toluenesulfonyloxy)phenyl)-2-(ethylamino)ethanol,
(1S)-1-(4-(4-toluenesulfonyloxy)phenyl)-2-(tert-butylamino)ethanol,
(1S)-1-(4-(4-toluenesulfonyloxy)phenyl)-2-(allylamino)ethanol,
(1S)-1-(4-(4-toluenesulfonyloxy)phenyl)-2-(N-benzyl-N-chloroacetylamino)ethanol,
(1S)-1-(4-(4-toluenesulfonyloxy)phenyl)-2-(N-benzyl-N-bromoacetylamino)ethanol,
(1S)-1-(4-(4-toluenesulfonyloxy)phenyl)-2-(N-(1R)-1-phenylethyl-N-chloroacetylamino)ethanol,
(1S)-1-(4-(4-toluenesulfonyloxy)phenyl)-2-(N-(1S)-1-phenylethyl-N-chloroacetylamino)ethanol,
(1S)-1-(4-(4-toluenesulfonyloxy)phenyl)-2-(N-(1R)-1-phenylethyl-N-bromoacetylamino)ethanol, and
(1S)-1-(4-(4-toluenesulfonyloxy)phenyl)-2-(N-(1S)-1-phenylethyl-N-bromoacetylamino)ethanol.

In addition, the compound of the formula 25, which is an optically active 2-ethanolamine compound (R-form) produced in Scheme 2, as well as the compound of the formula 26, which is produced from the compound of the formula 25 in Scheme 4, are novel compounds (these compounds are collectively shown as the following compounds of the formula 31):

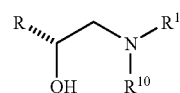

31 wherein each symbol is as defined above.

Of the above-mentioned compounds, a compound wherein R is a phenyl having 1 to 3 substituents selected from halogen, $C_1$-$C_6$ alkyl, substituted $C_1$-$C_6$ alkyl, $C_1$-$C_6$ alkoxy, substituted $C_1$-$C_6$ alkoxy, nitro aralkyloxy, $C_1$-$C_6$ alkylsulfonyloxy, arylsulfonyloxy and $C_1$-$C_6$ alkyl-substituted arylsulfonyloxy is preferable, and a compound wherein R is a phenyl having 1 to 3 substituents selected from fluorine, chlorine, bromine, nitro, benzyloxy, methanesulfonyloxy, benzenesulfonyloxy and toluenesulfonyloxy is more preferable. Specifically, the following compounds can be mentioned:

(1R)-1-(4-fluorophenyl)-2-(benzylamino)ethanol,
(1R)-1-(4-fluorophenyl)-2-(4-methoxybenzylamino)ethanol,
(1R)-1-(4-fluorophenyl)-2-(2,4-dimethoxybenzylamino)ethanol,
(1R)-1-(4-fluorophenyl)-2-((1R)-1-phenylethylamino)ethanol,
(1R)-1-(4-fluorophenyl)-2-((1S)-1-phenylethylamino)ethanol,
(1R)-1-(4-fluorophenyl)-2-(2-phenylethylamino)ethanol,
(1R)-1-(4-fluorophenyl)-2-(methylamino)ethanol,
(1R)-1-(4-fluorophenyl)-2-(ethylamino)ethanol,
(1R)-1-(4-fluorophenyl)-2-(tert-butylamino)ethanol,
(1R)-1-(4-fluorophenyl)-2-(allylamino)ethanol,
(1R)-1-(3-fluorophenyl)-2-(benzylamino)ethanol,
(1R)-1-(3-fluorophenyl)-2-(4-methoxybenzylamino)ethanol,
(1R)-1-(3-fluorophenyl)-2-(2,4-dimethoxybenzylamino)ethanol,
(1R)-1-(3-fluorophenyl)-2-((1R)-1-phenylethylamino)ethanol,
(1R)-1-(3-fluorophenyl)-2-((1S)-1-phenylethylamino)ethanol,
(1R)-1-(3-fluorophenyl)-2-(2-phenylethylamino)ethanol,
(1R)-1-(3-fluorophenyl)-2-(methylamino)ethanol,
(1R)-1-(3-fluorophenyl)-2-(ethylamino)ethanol,
(1R)-1-(3-fluorophenyl)-2-(tert-butylamino)ethanol,
(1R)-1-(3-fluorophenyl)-2-(allylamino)ethanol,
(1R)-1-(4-chlorophenyl)-2-(benzylamino)ethanol,
(1R)-1-(4-chlorophenyl)-2-(4-methoxybenzylamino)ethanol,
(1R)-1-(4-chlorophenyl)-2-(2,4-dimethoxybenzylamino)ethanol,
(1R)-1-(4-chlorophenyl)-2-((1R)-1-phenylethylamino)ethanol,
(1R)-1-(4-chlorophenyl)-2-((1S)-1-phenylethylamino)ethanol,
(1R)-1-(4-chlorophenyl)-2-(2-phenylethylamino)ethanol,
(1R)-1-(4-chlorophenyl)-2-(methylamino)ethanol,
(1R)-1-(4-chlorophenyl)-2-(ethylamino)ethanol,
(1R)-1-(4-chlorophenyl)-2-(tert-butylamino)ethanol,
(1R)-1-(4-chlorophenyl)-2-(allylamino)ethanol,
(1R)-1-(4-bromophenyl)-2-(benzylamino)ethanol,
(1R)-1-(4-bromophenyl)-2-(4-methoxybenzylamino)ethanol,
(1R)-1-(4-bromophenyl)-2-(2,4-dimethoxybenzylamino)ethanol,
(1R)-1-(4-bromophenyl)-2-((1R)-1-phenylethylamino)ethanol,
(1R)-1-(4-bromophenyl)-2-((1S)-1-phenylethylamino)ethanol,
(1R)-1-(4-bromophenyl)-2-(2-phenylethylamino)ethanol,
(1R)-1-(4-bromophenyl)-2-(methylamino)ethanol,
(1R)-1-(4-bromophenyl)-2-(ethylamino)ethanol,
(1R)-1-(4-bromophenyl)-2-(tert-butylamino)ethanol,
(1R)-1-(4-bromophenyl)-2-(allylamino)ethanol,
(1R)-1-(4-nitrophenyl)-2-(benzylamino)ethanol,
(1R)-1-(4-nitrophenyl)-2-(4-methoxybenzylamino)ethanol,
(1R)-1-(4-nitrophenyl)-2-(2,4-dimethoxybenzylamino)ethanol,
(1R)-1-(4-nitrophenyl)-2-((1R)-1-phenylethylamino)ethanol,
(1R)-1-(4-nitrophenyl)-2-((1S)-1-phenylethylamino)ethanol,
(1R)-1-(4-nitrophenyl)-2-(2-phenylethylamino)ethanol,
(1R)-1-(4-nitrophenyl)-2-(methylamino)ethanol,
(1R)-1-(4-nitrophenyl)-2-(ethylamino)ethanol,
(1R)-1-(4-nitrophenyl)-2-(tert-butylamino)ethanol,
(1R)-1-(4-nitrophenyl)-2-(allylamino)ethanol,
(1R)-1-(4-fluorophenyl)-2-(N-benzyl-N-chloroacetylamino)ethanol,
(1R)-1-(4-fluorophenyl)-2-(N-benzyl-N-bromoacetylamino)ethanol,
(1R)-1-(4-fluorophenyl)-2-(N-(1R)-1-phenylethyl-N-chloroacetylamino)ethanol,
(1R)-1-(4-fluorophenyl)-2-(N-(1S)-1-phenylethyl-N-chloroacetylamino)ethanol,
(1R)-1-(4-fluorophenyl)-2-(N-(1R)-1-phenylethyl-N-bromoacetylamino)ethanol,
(1R)-1-(4-fluorophenyl)-2-(N-(1S)-1-phenylethyl-N-bromoacetylamino)ethanol,
(1R)-1-(4-bromophenyl)-2-(N-benzyl-N-chloroacetylamino)ethanol,
(1R)-1-(4-bromophenyl)-2-(N-benzyl-N-bromoacetylamino)ethanol,
(1R)-1-(4-bromophenyl)-2-(N-(1R)-1-phenylethyl-N-chloroacetylamino)ethanol,
(1R)-1-(4-bromophenyl)-2-(N-(1S)-1-phenylethyl-N-chloroacetylamino)ethanol,
(1R)-1-(4-bromophenyl)-2-(N-(1R)-1-phenylethyl-N-bromoacetylamino)ethanol,
(1R)-1-(4-bromophenyl)-2-(N-(1S)-1-phenylethyl-N-bromoacetylamino)ethanol,
(1R)-1-(4-nitrophenyl)-2-(N-benzyl-N-chloroacetylamino)ethanol,
(1R)-1-(4-nitrophenyl)-2-(N-benzyl-N-bromoacetylamino)ethanol,
(1R)-1-(4-nitrophenyl)-2-(N-(1R)-1-phenylethyl-N-chloroacetylamino)ethanol,
(1R)-1-(4-nitrophenyl)-2-(N-(1S)-1-phenylethyl-N-chloroacetylamino)ethanol,
(1R)-1-(4-nitrophenyl)-2-(N-(1R)-1-phenylethyl-N-bromoacetylamino)ethanol,
(1R)-1-(4-nitrophenyl)-2-(N-(1S)-1-phenylethyl-N-bromoacetylamino)ethanol,
(1R)-1-(4-benzyloxyphenyl)-2-(benzylamino)ethanol,
(1R)-1-(4-benzyloxyphenyl)-2-(4-methoxybenzylamino)ethanol,
(1R)-1-(4-benzyloxyphenyl)-2-(2,4-dimethoxybenzylamino)ethanol,
(1R)-1-(4-benzyloxyphenyl)-2-((1R)-1-phenylethylamino)ethanol,
(1R)-1-(4-benzyloxyphenyl)-2-((1S)-1-phenylethylamino)ethanol,
(1R)-1-(4-benzyloxyphenyl)-2-(2-phenylethylamino)ethanol,
(1R)-1-(4-benzyloxyphenyl)-2-(methylamino)ethanol,
(1R)-1-(4-benzyloxyphenyl)-2-(ethylamino)ethanol,
(1R)-1-(4-benzyloxyphenyl)-2-(tert-butylamino)ethanol,
(1R)-1-(4-benzyloxyphenyl)-2-(allylamino)ethanol,
(1R)-1-(4-benzyloxyphenyl)-2-(N-benzyl-N-chloroacetylamino)ethanol,
(1R)-1-(4-benzyloxyphenyl)-2-(N-benzyl-N-bromoacetylamino)ethanol,
(1R)-1-(4-benzyloxyphenyl)-2-(N-(1R)-1-phenylethyl-N-chloroacetylamino)ethanol,
(1R)-1-(4-benzyloxyphenyl)-2-(N-(1S)-1-phenylethyl-N-chloroacetylamino)ethanol, (1R)-1-(4-benzyloxyphenyl)-2-(N-(1R)-1-phenylethyl-N-bromoacetylamino)ethanol,
(1R)-1-(4-benzyloxyphenyl)-2-(N-(1S)-1-phenylethyl-N-bromoacetylamino)ethanol,
(1R)-1-(4-methanesulfonyloxyphenyl)-2-(benzylamino)ethanol,
(1R)-1-(4-methanesulfonyloxyphenyl)-2-(4-methoxybenzylamino)ethanol,
(1R)-1-(4-methanesulfonyloxyphenyl)-2-(2,4-dimethoxybenzylamino)ethanol,
(1R)-1-(4-methanesulfonyloxyphenyl)-2-((1R)-1-phenylethylamino)ethanol,
(1R)-1-(4-methanesulfonyloxyphenyl)-2-((1S)-1-phenylethylamino)ethanol,
(1R)-1-(4-methanesulfonyloxyphenyl)-2-(2-phenylethylamino)ethanol,
(1R)-1-(4-methanesulfonyloxyphenyl)-2-(methylamino)ethanol,
(1R)-1-(4-methanesulfonyloxyphenyl)-2-(ethylamino)ethanol,
(1R)-1-(4-methanesulfonyloxyphenyl)-2-(tert-butylamino)ethanol,
(1R)-1-(4-methanesulfonyloxyphenyl)-2-(allylamino)ethanol,
(1R)-1-(4-methanesulfonyloxyphenyl)-2-(N-benzyl-N-chloroacetylamino)ethanol,
(1R)-1-(4-methanesulfonyloxyphenyl)-2-(N-benzyl-N-bromoacetylamino)ethanol,
(1R)-1-(4-methanesulfonyloxyphenyl)-2-(N-(1R)-1-phenylethyl-N-chloroacetylamino)ethanol,
(1R)-1-(4-methanesulfonyloxyphenyl)-2-(N-(1S)-1-phenylethyl-N-chloroacetylamino)ethanol,
(1R)-1-(4-methanesulfonyloxyphenyl)-2-(N-(1R)-1-phenylethyl-N-bromoacetylamino)ethanol,
(1R)-1-(4-methanesulfonyloxyphenyl)-2-(N-(1S)-1-phenylethyl-N-bromoacetylamino)ethanol,
(1R)-1-(4-benzenesulfonyloxyphenyl)-2-(benzylamino)ethanol,
(1R)-1-(4-benzenesulfonyloxyphenyl)-2-(4-methoxybenzylamino)ethanol,
(1R)-1-(4-benzenesulfonyloxyphenyl)-2-(2,4-dimethoxybenzylamino)ethanol,
(1R)-1-(4-benzenesulfonyloxyphenyl)-2-((1R)-1-phenylethylamino)ethanol,
(1R)-1-(4-benzenesulfonyloxyphenyl)-2-((1S)-1-phenylethylamino)ethanol,
(1R)-1-(4-benzenesulfonyloxyphenyl)-2-(2-phenylethylamino)ethanol,
(1R)-1-(4-benzenesulfonyloxyphenyl)-2-(methylamino)ethanol,
(1R)-1-(4-benzenesulfonyloxyphenyl)-2-(ethylamino)ethanol,
(1R)-1-(4-benzenesulfonyloxyphenyl)-2-(tert-butylamino)ethanol,
(1R)-1-(4-benzenesulfonyloxyphenyl)-2-(allylamino)ethanol,
(1R)-1-(4-benzenesulfonyloxyphenyl)-2-(N-benzyl-N-chloroacetylamino)ethanol,
(1R)-1-(4-benzenesulfonyloxyphenyl)-2-(N-benzyl-N-bromoacetylamino)ethanol,
(1R)-1-(4-benzenesulfonyloxyphenyl)-2-(N-(1R)-1-phenylethyl-N-chloroacetylamino)ethanol,
(1R)-1-(4-benzenesulfonyloxyphenyl)-2-(N-(1S)-1-phenylethyl-N-chloroacetylamino)ethanol,
(1R)-1-(4-benzenesulfonyloxyphenyl)-2-(N-(1R)-1-phenylethyl-N-bromoacetylamino)ethanol,
(1R)-1-(4-benzenesulfonyloxyphenyl)-2-(N-(1S)-1-phenylethyl-N-bromoacetylamino)ethanol,
(1R)-1-(4-(4-toluenesulfonyloxy)phenyl)-2-(benzylamino)ethanol,
(1R)-1-(4-(4-toluenesulfonyloxy)phenyl)-2-(4-methoxybenzylamino)ethanol,
(1R)-1-(4-(4-toluenesulfonyloxy)phenyl)-2-(2,4-dimethoxybenzylamino)ethanol,
(1R)-1-(4-(4-toluenesulfonyloxy)phenyl)-2-((1R)-1-phenylethylamino)ethanol,
(1R)-1-(4-(4-toluenesulfonyloxy)phenyl)-2-((1S)-1-phenylethylamino)ethanol,
(1R)-1-(4-(4-toluenesulfonyloxy)phenyl)-2-(2-phenylethylamino)ethanol,
(1R)-1-(4-(4-toluenesulfonyloxy)phenyl)-2-(methylamino)ethanol,
(1R)-1-(4-(4-toluenesulfonyloxy)phenyl)-2-(ethylamino)ethanol,
(1R)-1-(4-(4-toluenesulfonyloxy)phenyl)-2-(tert-butylamino)ethanol,
(1R)-1-(4-(4-toluenesulfonyloxy)phenyl)-2-(allylamino)ethanol,
(1R)-1-(4-(4-toluenesulfonyloxy)phenyl)-2-(N-benzyl-N-chloroacetylamino)ethanol,
(1R)-1-(4-(4-toluenesulfonyloxy)phenyl)-2-(N-benzyl-N-bromoacetylamino)ethanol,
(1R)-1-(4-(4-toluenesulfonyloxy)phenyl)-2-(N-(1R)-1-phenylethyl-N-chloroacetylamino)ethanol,
(1R)-1-(4-(4-toluenesulfonyloxy)phenyl)-2-(N-(1S)-1-phenylethyl-N-chloroacetylamino)ethanol,
(1R)-1-(4-(4-toluenesulfonyloxy)phenyl)-2-(N-(1R)-1-phenylethyl-N-bromoacetylamino)ethanol, and
(1R)-1-(4-(4-toluenesulfonyloxy)phenyl)-2-(N-(1S)-1-phenylethyl-N-bromoacetylamino)ethanol.

Furthermore, the compound of the formula 7, the compound of the formula 8 and the compound of the formula 9 in Scheme 3 are novel compounds (these compounds are collectively shown as the following compounds of the formula 12):

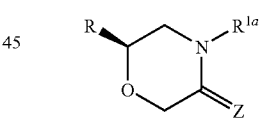

12 wherein each symbol is as defined above.

Of the above-mentioned compounds, a compound wherein R is a phenyl having 1 to 3 substituents selected from halogen, $C_1$-$C_6$ alkyl, substituted $C_1$-$C_6$ alkyl, $C_1$-$C_6$ alkoxy, substituted $C_1$-$C_6$ alkoxy, nitro aralkyloxy, $C_1$-$C_6$ alkylsulfonyloxy, arylsulfonyloxy and $C_1$-$C_6$ alkyl-substituted arylsulfonyloxy is preferable, and a compound wherein R is a phenyl having 1 to 3 substituents selected from fluorine, chlorine, bromine, nitro, benzyloxy, methanesulfonyloxy, benzenesulfonyloxy and toluenesulfonyloxy is more preferable. Specifically, the following compounds can be mentioned:
(6S)-6-(4-fluorophenyl)-4-(benzyl)morpholin-3-one,
(6S)-6-(4-fluorophenyl)-4-(4-methoxybenzyl)morpholin-3-one,
(6S)-6-(4-fluorophenyl)-4-(2,4-dimethoxybenzyl)morpholin-3-one,
(6S)-6-(4-fluorophenyl)-4-((1R)-1-phenylethyl)morpholin-3-one, (6S)-6-(4-fluorophenyl)-4-((1S)-1-phenylethyl)morpholin-3-one,
(6S)-6-(4-fluorophenyl)-4-(2-phenylethyl)morpholin-3-one,
(6S)-6-(4-fluorophenyl)-4-(methyl)morpholin-3-one,
(6S)-6-(4-fluorophenyl)-4-(ethyl)morpholin-3-one,
(6S)-6-(4-fluorophenyl)-4-(tert-butyl)morpholin-3-one,
(6S)-6-(4-fluorophenyl)-4-(allyl)morpholin-3-one,
(6S)-6-(4-fluorophenyl)morpholin-3-one,
(6S)-6-(3-fluorophenyl)-4-(benzyl)morpholin-3-one,
(6S)-6-(3-fluorophenyl)-4-(4-methoxybenzyl)morpholin-3-one,
(6S)-6-(3-fluorophenyl)-4-(2,4-dimethoxybenzyl)morpholin-3-one,
(6S)-6-(3-fluorophenyl)-4-((1R)-1-phenylethyl)morpholin-3-one,
(6S)-6-(3-fluorophenyl)-4-((1S)-1-phenylethyl)morpholin-3-one,
(6S)-6-(3-fluorophenyl)-4-(2-phenylethyl)morpholin-3-one,
(6S)-6-(3-fluorophenyl)-4-(methyl)morpholin-3-one,
(6S)-6-(3-fluorophenyl)-4-(ethyl)morpholin-3-one,
(6S)-6-(3-fluorophenyl)-4-(tert-butyl)morpholin-3-one,
(6S)-6-(3-fluorophenyl)-4-(allyl)morpholin-3-one,
(6S)-6-(3-fluorophenyl)morpholin-3-one,
(6S)-6-(4-chlorophenyl)-4-(benzyl)morpholin-3-one,
(6S)-6-(4-chlorophenyl)-4-(4-methoxybenzyl)morpholin-3-one,
(6S)-6-(4-chlorophenyl)-4-(2,4-dimethoxybenzyl)morpholin-3-one,
(6S)-6-(4-chlorophenyl)-4-((1R)-1-phenylethyl)morpholin-3-one,
(6S)-6-(4-chlorophenyl)-4-((1S)-1-phenylethyl)morpholin-3-one,
(6S)-6-(4-chlorophenyl)-4-(2-phenylethyl)morpholin-3-one,
(6S)-6-(4-chlorophenyl)-4-(methyl)morpholin-3-one,
(6S)-6-(4-chlorophenyl)-4-(ethyl)morpholin-3-one,
(6S)-6-(4-chlorophenyl)-4-(tert-butyl)morpholin-3-one,
(6S)-6-(4-chlorophenyl)-4-(allyl)morpholin-3-one,
(6S)-6-(4-bromophenyl)-4-(benzyl)morpholin-3-one,
(6S)-6-(4-bromophenyl)-4-(4-methoxybenzyl)morpholin-3-one,
(6S)-6-(4-bromophenyl)-4-(2,4-dimethoxybenzyl)morpholin-3-one,
(6S)-6-(4-bromophenyl)-4-((1R)-1-phenylethyl)morpholin-3-one,
(6S)-6-(4-bromophenyl)-4-((1S)-1-phenylethyl)morpholin-3-one,
(6S)-6-(4-bromophenyl)-4-(2-phenylethyl)morpholin-3-one,
(6S)-6-(4-bromophenyl)-4-(methyl)morpholin-3-one,
(6S)-6-(4-bromophenyl)-4-(ethyl)morpholin-3-one,
(6S)-6-(4-bromophenyl)-4-(tert-butyl)morpholin-3-one,
(6S)-6-(4-bromophenyl)-4-(allyl)morpholin-3-one,
(6S)-6-(4-nitrophenyl)-4-(benzyl)morpholin-3-one,
(6S)-6-(4-nitrophenyl)-4-(4-methoxybenzyl)morpholin-3-one,
(6S)-6-(4-nitrophenyl)-4-(2,4-dimethoxybenzyl)morpholin-3-one,
(6S)-6-(4-nitrophenyl)-4-((1R)-1-phenylethyl)morpholin-3-one,
(6S)-6-(4-nitrophenyl)-4-((1S)-1-phenylethyl)morpholin-3-one,
(6S)-6-(4-nitrophenyl)-4-(2-phenylethyl)morpholin-3-one,
(6S)-6-(4-nitrophenyl)-4-(methyl)morpholin-3-one,
(6S)-6-(4-nitrophenyl)-4-(ethyl)morpholin-3-one,
(6S)-6-(4-nitrophenyl)-4-(tert-butyl)morpholin-3-one,
(6S)-6-(4-nitrophenyl)-4-(allyl)morpholin-3-one,
(2S)-2-(4-fluorophenyl)-4-(benzyl)morpholine,
(2S)-2-(4-fluorophenyl)-4-(4-methoxybenzyl)morpholine,
(2S)-2-(4-fluorophenyl)-4-(2,4-dimethoxybenzyl)morpholine,
(2S)-2-(4-fluorophenyl)-4-((1R)-1-phenylethyl)morpholine,
(2S)-2-(4-fluorophenyl)-4-((1S)-1-phenylethyl)morpholine,
(2S)-2-(4-fluorophenyl)-4-(2-phenylethyl)morpholine,
(2S)-2-(4-fluorophenyl)-4-(methyl)morpholine,
(2S)-2-(4-fluorophenyl)-4-(ethyl)morpholine,
(2S)-2-(4-fluorophenyl)-4-(tert-butyl)morpholine,
(2S)-2-(4-fluorophenyl)-4-(allyl)morpholine,
(2S)-2-(3-fluorophenyl)-4-(benzyl)morpholine,
(2S)-2-(3-fluorophenyl)-4-(4-methoxybenzyl)morpholine,
(2S)-2-(3-fluorophenyl)-4-(2,4-dimethoxybenzyl)morpholine,
(2S)-2-(3-fluorophenyl)-4-((1R)-1-phenylethyl)morpholine,
(2S)-2-(3-fluorophenyl)-4-((1S)-1-phenylethyl)morpholine,
(2S)-2-(3-fluorophenyl)-4-(2-phenylethyl)morpholine,
(2S)-2-(3-fluorophenyl)-4-(methyl)morpholine,
(2S)-2-(3-fluorophenyl)-4-(ethyl)morpholine,
(2S)-2-(3-fluorophenyl)-4-(tert-butyl)morpholine,
(2S)-2-(3-fluorophenyl)-4-(allyl)morpholine,
(2S)-2-(3-fluorophenyl)morpholine,
(2S)-2-(4-chlorophenyl)-4-(benzyl)morpholine,
(2S)-2-(4-chlorophenyl)-4-(4-methoxybenzyl)morpholine,
(2S)-2-(4-chlorophenyl)-4-(2,4-dimethoxybenzyl)morpholine,
(2S)-2-(4-chlorophenyl)-4-((1R)-1-phenylethyl)morpholine,
(2S)-2-(4-chlorophenyl)-4-((1S)-1-phenylethyl)morpholine,
(2S)-2-(4-chlorophenyl)-4-(2-phenylethyl)morpholine,
(2S)-2-(4-chlorophenyl)-4-(methyl)morpholine,
(2S)-2-(4-chlorophenyl)-4-(ethyl)morpholine,
(2S)-2-(4-chlorophenyl)-4-(tert-butyl)morpholine,
(2S)-2-(4-chlorophenyl)-4-(allyl)morpholine,
(2S)-2-(4-bromophenyl)-4-(benzyl)morpholine,
(2S)-2-(4-bromophenyl)-4-(4-methoxybenzyl)morpholine,
(2S)-2-(4-bromophenyl)-4-(2,4-dimethoxybenzyl)morpholine,
(2S)-2-(4-bromophenyl)-4-((1R)-1-phenylethyl)morpholine,
(2S)-2-(4-bromophenyl)-4-((1S)-1-phenylethyl)morpholine,
(2S)-2-(4-bromophenyl)-4-(2-phenylethyl)morpholine,
(2S)-2-(4-bromophenyl)-4-(methyl)morpholine,
(2S)-2-(4-bromophenyl)-4-(ethyl)morpholine,
(2S)-2-(4-bromophenyl)-4-(tert-butyl)morpholine,
(2S)-2-(4-bromophenyl)-4-(allyl)morpholine,
(2S)-2-(4-bromophenyl)morpholine,
(2S)-2-(4-nitrophenyl)-4-(benzyl)morpholine,
(2S)-2-(4-nitrophenyl)-4-(4-methoxybenzyl)morpholine,
(2S)-2-(4-nitrophenyl)-4-(2,4-dimethoxybenzyl)morpholine,
(2S)-2-(4-nitrophenyl)-4-((1R)-1-phenylethyl)morpholine,
(2S)-2-(4-nitrophenyl)-4-((1S)-1-phenylethyl)morpholine,
(2S)-2-(4-nitrophenyl)-4-(2-phenylethyl)morpholine,
(2S)-2-(4-nitrophenyl)-4-(methyl)morpholine,
(2S)-2-(4-nitrophenyl)-4-(ethyl)morpholine,
(2S)-2-(4-nitrophenyl)-4-(tert-butyl)morpholine,
(2S)-2-(4-nitrophenyl)-4-(allyl)morpholine,
(2S)-2-(4-nitrophenyl)morpholine,
methyl (2S)-2-(4-fluorophenyl)morpholine-4-carboxylate,
ethyl (2S)-2-(4-fluorophenyl)morpholine-4-carboxylate,
phenyl (2S)-2-(4-fluorophenyl)morpholine-4-carboxylate,
4-nitrophenyl (2S)-2-(4-fluorophenyl)morpholine-4-carboxylate,
methyl (2S)-2-(3-fluorophenyl)morpholine-4-carboxylate,
ethyl (2S)-2-(3-fluorophenyl)morpholine-4-carboxylate, phenyl (2S)-2-(3-fluorophenyl)morpholine-4-carboxylate,
4-nitrophenyl (2S)-2-(3-fluorophenyl)morpholine-4-carboxylate,
methyl (2S)-2-(4-chlorophenyl)morpholine-4-carboxylate,
ethyl (2S)-2-(4-chlorophenyl)morpholine-4-carboxylate,
phenyl (2S)-2-(4-chlorophenyl)morpholine-4-carboxylate,
4-nitrophenyl (2S)-2-(4-chlorophenyl)morpholine-4-carboxylate,
methyl (2S)-2-(4-bromophenyl)morpholine-4-carboxylate,
ethyl (2S)-2-(4-bromophenyl)morpholine-4-carboxylate,
phenyl (2S)-2-(4-bromophenyl)morpholine-4-carboxylate,
4-nitrophenyl (2S)-2-(4-bromophenyl)morpholine-4-carboxylate,
methyl (2S)-2-(4-nitrophenyl)morpholine-4-carboxylate,
ethyl (2S)-2-(4-nitrophenyl)morpholine-4-carboxylate,
phenyl (2S)-2-(4-nitrophenyl)morpholine-4-carboxylate,
4-nitrophenyl (2S)-2-(4-nitrophenyl)morpholine-4-carboxylate,
1-chloroethyl (2S)-2-(4-fluorophenyl)morpholine-4-carboxylate,
1-chloroethyl (2S)-2-(3-fluorophenyl)morpholine-4-carboxylate,
1-chloroethyl (2S)-2-(4-chlorophenyl)morpholine-4-carboxylate,
1-chloroethyl (2S)-2-(4-bromophenyl)morpholine-4-carboxylate,
1-chloroethyl (2S)-2-(4-nitrophenyl)morpholine-4-carboxylate,
(6S)-6-(4-benzyloxyphenyl)-4-(benzyl)morpholin-3-one,
(6S)-6-(4-benzyloxyphenyl)-4-(4-methoxybenzyl)morpholin-3-one,
(6S)-6-(4-benzyloxyphenyl)-4-(2,4-dimethoxybenzyl)morpholin-3-one,
(6S)-6-(4-benzyloxyphenyl)-4-((1R)-1-phenylethyl)morpholin-3-one,
(6S)-6-(4-benzyloxyphenyl)-4-((1S)-1-phenylethyl)morpholin-3-one,
(6S)-6-(4-benzyloxyphenyl)-4-(2-phenylethyl)morpholin-3-one,
(6S)-6-(4-benzyloxyphenyl)-4-(methyl)morpholin-3-one,
(6S)-6-(4-benzyloxyphenyl)-4-(ethyl)morpholin-3-one,
(6S)-6-(4-benzyloxyphenyl)-4-(tert-butyl)morpholin-3-one,
(6S)-6-(4-benzyloxyphenyl)-4-(allyl)morpholin-3-one,
(6S)-6-(4-benzyloxyphenyl)morpholin-3-one,
(2S)-2-(4-benzyloxyphenyl)-4-(benzyl)morpholine,
(2S)-2-(4-benzyloxyphenyl)-4-(4-methoxybenzyl)morpholine,
(2S)-2-(4-benzyloxyphenyl)-4-(2,4-dimethoxybenzyl)morpholine,
(2S)-2-(4-benzyloxyphenyl)-4-((1R)-1-phenylethyl)morpholine,
(2S)-2-(4-benzyloxyphenyl)-4-((1S)-1-phenylethyl)morpholine,
(2S)-2-(4-benzyloxyphenyl)-4-(2-phenylethyl)morpholine,
(2S)-2-(4-benzyloxyphenyl)-4-(methyl)morpholine,
(2S)-2-(4-benzyloxyphenyl)-4-(ethyl)morpholine,
(2S)-2-(4-benzyloxyphenyl)-4-(tert-butyl)morpholine,
(2S)-2-(4-benzyloxyphenyl)-4-(allyl)morpholine,
methyl (2S)-2-(4-benzyloxyphenyl)morpholine-4-carboxylate,
ethyl (2S)-2-(4-benzyloxyphenyl)morpholine-4-carboxylate,
1-chloroethyl (2S)-2-(4-benzyloxyphenyl)morpholine-4-carboxylate,
phenyl (2S)-2-(4-benzyloxyphenyl)morpholine-4-carboxylate,
4-nitrophenyl (2S)-2-(4-benzyloxyphenyl)morpholine-4-carboxylate,
(6S)-6-(4-methanesulfonyloxyphenyl)-4-(benzyl)morpholin-3-one,
(6S)-6-(4-methanesulfonyloxyphenyl)-4-(4-methoxybenzyl)morpholin-3-one,
(6S)-6-(4-methanesulfonyloxyphenyl)-4-(2,4-dimethoxybenzyl)morpholin-3-one,
(6S)-6-(4-methanesulfonyloxyphenyl)-4-((1R)-1-phenylethyl)morpholin-3-one,
(6S)-6-(4-methanesulfonyloxyphenyl)-4-((1S)-1-phenylethyl)morpholin-3-one,
(6S)-6-(4-methanesulfonyloxyphenyl)-4-(2-phenylethyl)morpholin-3-one,
(6S)-6-(4-methanesulfonyloxyphenyl)-4-(methyl)morpholin-3-one,
(6S)-6-(4-methanesulfonyloxyphenyl)-4-(ethyl)morpholin-3-one,
(6S)-6-(4-methanesulfonyloxyphenyl)-4-(tert-butyl)morpholin-3-one,
(6S)-6-(4-methanesulfonyloxyphenyl)-4-(allyl)morpholin-3-one;
(6S)-6-(4-methanesulfonyloxyphenyl)morpholin-3-one,
(2S)-2-(4-methanesulfonyloxyphenyl)-4-(benzyl)morpholine,
(2S)-2-(4-methanesulfonyloxyphenyl)-4-(4-methoxybenzyl)morpholine,
(2S)-2-(4-methanesulfonyloxyphenyl)-4-(2,4-dimethoxybenzyl)morpholine,
(2S)-2-(4-methanesulfonyloxyphenyl)-4-((1R)-1-phenylethyl)morpholine,
(2S)-2-(4-methanesulfonyloxyphenyl)-4-((1S)-1-phenylethyl)morpholine,
(2S)-2-(4-methanesulfonyloxyphenyl)-4-(2-phenylethyl)morpholine,
(2S)-2-(4-methanesulfonyloxyphenyl)-4-(methyl)morpholine,
(2S)-2-(4-methanesulfonyloxyphenyl)-4-(ethyl)morpholine,
(2S)-2-(4-methanesulfonyloxyphenyl)-4-(tert-butyl)morpholine,
(2S)-2-(4-methanesulfonyloxyphenyl)-4-(allyl)morpholine,
methyl (2S)-2-(4-methanesulfonyloxyphenyl)morpholine-4-carboxylate,
ethyl (2S)-2-(4-methanesulfonyloxyphenyl)morpholine-4-carboxylate,
1-chloroethyl (2S)-2-(4-methanesulfonyloxyphenyl)morpholine-4-carboxylate,
phenyl (2S)-2-(4-methanesulfonyloxyphenyl)morpholine-4-carboxylate,
4-nitrophenyl (2S)-2-(4-methanesulfonyloxyphenyl)morpholine-4-carboxylate,
(6S)-6-(4-benzenesulfonyloxyphenyl)-4-(benzyl)morpholin-3-one,
(6S)-6-(4-benzenesulfonyloxyphenyl)-4-(4-methoxybenzyl)morpholin-3-one,
(6S)-6-(4-benzenesulfonyloxyphenyl)-4-(2,4-dimethoxybenzyl)morpholin-3-one,
(6S)-6-(4-benzenesulfonyloxyphenyl)-4-((1R)-1-phenylethyl)morpholin-3-one,
(6S)-6-(4-benzenesulfonyloxyphenyl)-4-((1S)-1-phenylethyl)morpholin-3-one,
(6S)-6-(4-benzenesulfonyloxyphenyl)-4-(2-phenylethyl)morpholin-3-one,
(6S)-6-(4-benzenesulfonyloxyphenyl)-4-(methyl)morpholin-3-one,
(6S)-6-(4-benzenesulfonyloxyphenyl)-4-(ethyl)morpholin-3-one, (6S)-6-(4-benzenesulfonyloxyphenyl)-4-(tert-butyl)morpholin-3-one,
(6S)-6-(4-benzenesulfonyloxyphenyl)-4-(allyl)morpholin-3-one,
(6S)-6-(4-benzenesulfonyloxyphenyl)morpholin-3-one,
(2S)-2-(4-benzenesulfonyloxyphenyl)-4-(benzyl)morpholine,
(2S)-2-(4-benzenesulfonyloxyphenyl)-4-(4-methoxybenzyl)morpholine,
(2S)-2-(4-benzenesulfonyloxyphenyl)-4-(2,4-dimethoxybenzyl)morpholine,
(2S)-2-(4-benzenesulfonyloxyphenyl)-4-((1R)-1-phenylethyl)morpholine,
(2S)-2-(4-benzenesulfonyloxyphenyl)-4-((1S)-1-phenylethyl)morpholine,
(2S)-2-(4-benzenesulfonyloxyphenyl)-4-(2-phenylethyl)morpholine,
(2S)-2-(4-benzenesulfonyloxyphenyl)-4-(methyl)morpholine,
(2S)-2-(4-benzenesulfonyloxyphenyl)-4-(ethyl)morpholine,
(2S)-2-(4-benzenesulfonyloxyphenyl)-4-(tert-butyl)morpholine,
(2S)-2-(4-benzenesulfonyloxyphenyl)-4-(allyl)morpholine,
methyl (2S)-2-(4-benzenesulfonyloxyphenyl)morpholine-4-carboxylate,
ethyl (2S)-2-(4-benzenesulfonyloxyphenyl)morpholine-4-carboxylate,
1-chloroethyl (2S)-2-(4-benzenesulfonyloxyphenyl)morpholine-4-carboxylate,
phenyl (2S)-2-(4-benzenesulfonyloxyphenyl)morpholine-4-carboxylate,
4-nitrophenyl (2S)-2-(4-benzenesulfonyloxyphenyl)morpholine-4-carboxylate,
(6S)-6-(4-(4-toluenesulfonyloxy)phenyl)-4-(benzyl)morpholin-3-one,
(6S)-6-(4-(4-toluenesulfonyloxy)phenyl)-4-(4-methoxybenzyl)morpholin-3-one,
(6S)-6-(4-(4-toluenesulfonyloxy)phenyl)-4-(2,4-dimethoxybenzyl)morpholin-3-one,
(6S)-6-(4-(4-toluenesulfonyloxy)phenyl)-4-((1R)-1-phenylethyl)morpholin-3-one,
(6S)-6-(4-(4-toluenesulfonyloxy)phenyl)-4-((1S)-1-phenylethyl)morpholin-3-one,
(6S)-6-(4-(4-toluenesulfonyloxy)phenyl)-4-(2-phenylethyl)morpholin-3-one,
(6S)-6-(4-(4-toluenesulfonyloxy)phenyl)-4-(methyl)morpholin-3-one,
(6S)-6-(4-(4-toluenesulfonyloxy)phenyl)-4-(ethyl)morpholin-3-one,
(6S)-6-(4-(4-toluenesulfonyloxy)phenyl)-4-(tert-butyl)morpholin-3-one,
(6S)-6-(4-(4-toluenesulfonyloxy)phenyl)-4-(allyl)morpholin-3-one,
(6S)-6-(4-(4-toluenesulfonyloxy)phenyl)morpholin-3-one,
(2S)-2-(4-(4-toluenesulfonyloxy)phenyl)-4-(benzyl)morpholine,
(2S)-2-(4-(4-toluenesulfonyloxy)phenyl)-4-(4-methoxybenzyl)morpholine,
(2S)-2-(4-(4-toluenesulfonyloxy)phenyl)-4-(2,4-dimethoxybenzyl)morpholine,
(2S)-2-(4-(4-toluenesulfonyloxy)phenyl)-4-((1R)-1-phenylethyl)morpholine,
(2S)-2-(4-(4-toluenesulfonyloxy)phenyl)-4-((1S)-1-phenylethyl)morpholine,
(2S)-2-(4-(4-toluenesulfonyloxy)phenyl)-4-(2-phenylethyl)morpholine,
(2S)-2-(4-(4-toluenesulfonyloxy)phenyl)-4-(methyl)morpholine,
(2S)-2-(4-(4-toluenesulfonyloxy)phenyl)-4-(ethyl)morpholine,
(2S)-2-(4-(4-toluenesulfonyloxy)phenyl)-4-(tert-butyl)morpholine,
(2S)-2-(4-(4-toluenesulfonyloxy)phenyl)-4-(allyl)morpholine,
methyl (2S)-2-(4-(4-toluenesulfonyloxy)phenyl)morpholine-4-carboxylate,
ethyl (2S)-2-(4-(4-toluenesulfonyloxy)phenyl)morpholine-4-carboxylate,
1-chloroethyl (2S)-2-(4-(4-toluenesulfonyloxy)phenyl)morpholine-4-carboxylate,
phenyl (2S)-2-(4-(4-toluenesulfonyloxy)phenyl)morpholine-4-carboxylate, and
4-nitrophenyl (2S)-2-(4-(4-toluenesulfonyloxy)phenyl)morpholine-4-carboxylate.

Furthermore, the compound of the formula 27, the compound of the formula 28 and the compound of the formula 29 in Scheme 4 are also novel compounds (these compounds are collectively shown as the following compounds of the formula 32):

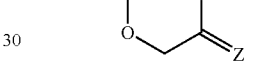

32 wherein each symbol is as defined above.

Of the above-mentioned compounds, a compound wherein R is a phenyl having 1 to 3 substituents selected from halogen, $C_1$-$C_6$ alkyl, substituted $C_1$-$C_6$ alkyl, $C_1$-$C_6$ alkoxy, substituted $C_1$-$C_6$ alkoxy, nitro aralkyloxy, $C_1$-$C_6$ alkylsulfonyloxy, arylsulfonyloxy and $C_1$-$C_6$ alkyl-substituted arylsulfonyloxy is preferable, and a compound wherein R is a phenyl having 1 to 3 substituents selected from fluorine, chlorine, bromine, nitro, benzyloxy, methanesulfonyloxy, benzenesulfonyloxy and toluenesulfonyloxy is more preferable. Specifically, the following compounds can be mentioned:
(6R)-6-(4-fluorophenyl)-4-(benzyl)morpholin-3-one,
(6R)-6-(4-fluorophenyl)-4-(4-methoxybenzyl)morpholin-3-one,
(6R)-6-(4-fluorophenyl)-4-(2,4-dimethoxybenzyl)morpholin-3-one,
(6R)-6-(4-fluorophenyl)-4-((1R)-1-phenylethyl)morpholin-3-one,
(6R)-6-(4-fluorophenyl)-4-((1S)-1-phenylethyl)morpholin-3-one,
(6R)-6-(4-fluorophenyl)-4-(2-phenylethyl)morpholin-3-one,
(6R)-6-(4-fluorophenyl)-4-(methyl)morpholin-3-one,
(6R)-6-(4-fluorophenyl)-4-(ethyl)morpholin-3-one,
(6R)-6-(4-fluorophenyl)-4-(tert-butyl)morpholin-3-one,
(6R)-6-(4-fluorophenyl)-4-(allyl)morpholin-3-one,
(6R)-6-(4-fluorophenyl)morpholin-3-one,
(6R)-6-(3-fluorophenyl)-4-(benzyl)morpholin-3-one,
(6R)-6-(3-fluorophenyl)-4-(4-methoxybenzyl)morpholin-3-one,
(6R)-6-(3-fluorophenyl)-4-(2,4-dimethoxybenzyl)morpholin-3-one,
(6R)-6-(3-fluorophenyl)-4-((1R)-1-phenylethyl)morpholin-3-one,
(6R)-6-(3-fluorophenyl)-4-((1S)-1-phenylethyl)morpholin-3-one, (6R)-6-(3-fluorophenyl)-4-(2-phenylethyl)morpholin-3-one,
(6R)-6-(3-fluorophenyl)-4-(methyl)morpholin-3-one,
(6R)-6-(3-fluorophenyl)-4-(ethyl)morpholin-3-one,
(6R)-6-(3-fluorophenyl)-4-(tert-butyl)morpholin-3-one,
(6R)-6-(3-fluorophenyl)-4-(allyl)morpholin-3-one,
(6R)-6-(3-fluorophenyl)morpholin-3-one,
(6R)-6-(4-chlorophenyl)-4-(benzyl)morpholin-3-one,
(6R)-6-(4-chlorophenyl)-4-(4-methoxybenzyl)morpholin-3-one,
(6R)-6-(4-chlorophenyl)-4-(2,4-dimethoxybenzyl)morpholin-3-one,
(6R)-6-(4-chlorophenyl)-4-((1R)-1-phenylethyl)morpholin-3-one,
(6R)-6-(4-chlorophenyl)-4-((1S)-1-phenylethyl)morpholin-3-one,
(6R)-6-(4-chlorophenyl)-4-(2-phenylethyl)morpholin-3-one,
(6R)-6-(4-chlorophenyl)-4-(methyl)morpholin-3-one,
(6R)-6-(4-chlorophenyl)-4-(ethyl)morpholin-3-one,
(6R)-6-(4-chlorophenyl)-4-(tert-butyl)morpholin-3-one,
(6R)-6-(4-chlorophenyl)-4-(allyl)morpholin-3-one,
(6R)-6-(4-bromophenyl)-4-(benzyl)morpholin-3-one,
(6R)-6-(4-bromophenyl)-4-(4-methoxybenzyl)morpholin-3-one,
(6R)-6-(4-bromophenyl)-4-(2,4-dimethoxybenzyl)morpholin-3-one,
(6R)-6-(4-bromophenyl)-4-((1R)-1-phenylethyl)morpholin-3-one,
(6R)-6-(4-bromophenyl)-4-((1S)-1-phenylethyl)morpholin-3-one,
(6R)-6-(4-bromophenyl)-4-(2-phenylethyl)morpholin-3-one,
(6R)-6-(4-bromophenyl)-4-(methyl)morpholin-3-one,
(6R)-6-(4-bromophenyl)-4-(ethyl)morpholin-3-one,
(6R)-6-(4-bromophenyl)-4-(tert-butyl)morpholin-3-one,
(6R)-6-(4-bromophenyl)-4-(allyl)morpholin-3-one,
(6R)-6-(4-nitrophenyl)-4-(benzyl)morpholin-3-one,
(6R)-6-(4-nitrophenyl)-4-(4-methoxybenzyl)morpholin-3-one,
(6R)-6-(4-nitrophenyl)-4-(2,4-dimethoxybenzyl)morpholin-3-one,
(6R)-6-(4-nitrophenyl)-4-((1R)-1-phenylethyl)morpholin-3-one,
(6R)-6-(4-nitrophenyl)-4-((1S)-1-phenylethyl)morpholin-3-one,
(6R)-6-(4-nitrophenyl)-4-(2-phenylethyl)morpholin-3-one,
(6R)-6-(4-nitrophenyl)-4-(methyl)morpholin-3-one,
(6R)-6-(4-nitrophenyl)-4-(ethyl)morpholin-3-one,
(6R)-6-(4-nitrophenyl)-4-(tert-butyl)morpholin-3-one,
(6R)-6-(4-nitrophenyl)-4-(allyl)morpholin-3-one,
(2R)-2-(4-fluorophenyl)-4-(benzyl)morpholine,
(2R)-2-(4-fluorophenyl)-4-(4-methoxybenzyl)morpholine,
(2R)-2-(4-fluorophenyl)-4-(2,4-dimethoxybenzyl)morpholine,
(2R)-2-(4-fluorophenyl)-4-((1R)-1-phenylethyl)morpholine,
(2R)-2-(4-fluorophenyl)-4-((1S)-1-phenylethyl)morpholine,
(2R)-2-(4-fluorophenyl)-4-(2-phenylethyl)morpholine,
(2R)-2-(4-fluorophenyl)-4-(methyl)morpholine,
(2R)-2-(4-fluorophenyl)-4-(ethyl)morpholine,
(2R)-2-(4-fluorophenyl)-4-(tert-butyl)morpholine,
(2R)-2-(4-fluorophenyl)-4-(allyl)morpholine,
(2R)-2-(3-fluorophenyl)-4-(benzyl)morpholine,
(2R)-2-(3-fluorophenyl)-4-(4-methoxybenzyl)morpholine,
(2R)-2-(3-fluorophenyl)-4-(2,4-dimethoxybenzyl)morpholine,
(2R)-2-(3-fluorophenyl)-4-((1R)-1-phenylethyl)morpholine,
(2R)-2-(3-fluorophenyl)-4-((1S)-1-phenylethyl)morpholine,
(2R)-2-(3-fluorophenyl)-4-(2-phenylethyl)morpholine,
(2R)-2-(3-fluorophenyl)-4-(methyl)morpholine,
(2R)-2-(3-fluorophenyl)-4-(ethyl)morpholine,
(2R)-2-(3-fluorophenyl)-4-(tert-butyl)morpholine,
(2R)-2-(3-fluorophenyl)-4-(allyl)morpholine,
(2R)-2-(3-fluorophenyl)morpholine,
(2R)-2-(4-chlorophenyl)-4-(benzyl)morpholine,
(2R)-2-(4-chlorophenyl)-4-(4-methoxybenzyl)morpholine,
(2R)-2-(4-chlorophenyl)-4-(2,4-dimethoxybenzyl)morpholine,
(2R)-2-(4-chlorophenyl)-4-((1R)-1-phenylethyl)morpholine,
(2R)-2-(4-chlorophenyl)-4-((1S)-1-phenylethyl)morpholine,
(2R)-2-(4-chlorophenyl)-4-(2-phenylethyl)morpholine,
(2R)-2-(4-chlorophenyl)-4-(methyl)morpholine,
(2R)-2-(4-chlorophenyl)-4-(ethyl)morpholine,
(2R)-2-(4-chlorophenyl)-4-(tert-butyl)morpholine,
(2R)-2-(4-chlorophenyl)-4-(allyl)morpholine,
(2R)-2-(4-bromophenyl)-4-(benzyl)morpholine,
(2R)-2-(4-bromophenyl)-4-(4-methoxybenzyl)morpholine,
(2R)-2-(4-bromophenyl)-4-(2,4-dimethoxybenzyl)morpholine,
(2R)-2-(4-bromophenyl)-4-((1R)-1-phenylethyl)morpholine,
(2R)-2-(4-bromophenyl)-4-((1S)-1-phenylethyl)morpholine,
(2R)-2-(4-bromophenyl)-4-(2-phenylethyl)morpholine,
(2R)-2-(4-bromophenyl)-4-(methyl)morpholine,
(2R)-2-(4-bromophenyl)-4-(ethyl)morpholine,
(2R)-2-(4-bromophenyl)-4-(tert-butyl)morpholine,
(2R)-2-(4-bromophenyl)-4-(allyl)morpholine,
(2R)-2-(4-bromophenyl)morpholine,
(2R)-2-(4-nitrophenyl)-4-(benzyl)morpholine,
(2R)-2-(4-nitrophenyl)-4-(4-methoxybenzyl)morpholine,
(2R)-2-(4-nitrophenyl)-4-(2,4-dimethoxybenzyl)morpholine,
(2R)-2-(4-nitrophenyl)-4-((1R)-1-phenylethyl)morpholine,
(2R)-2-(4-nitrophenyl)-4-((1S)-1-phenylethyl)morpholine,
(2R)-2-(4-nitrophenyl)-4-(2-phenylethyl)morpholine,
(2R)-2-(4-nitrophenyl)-4-(methyl)morpholine,
(2R)-2-(4-nitrophenyl)-4-(ethyl)morpholine,
(2R)-2-(4-nitrophenyl)-4-(tert-butyl)morpholine,
(2R)-2-(4-nitrophenyl)-4-(allyl)morpholine,
(2R)-2-(4-nitrophenyl)morpholine,
methyl (2R)-2-(4-fluorophenyl)morpholine-4-carboxylate,
ethyl (2R)-2-(4-fluorophenyl)morpholine-4-carboxylate,
phenyl (2R)-2-(4-fluorophenyl)morpholine-4-carboxylate,
4-nitrophenyl (2R)-2-(4-fluorophenyl)morpholine-4-carboxylate,
methyl (2R)-2-(3-fluorophenyl)morpholine-4-carboxylate,
ethyl (2R)-2-(3-fluorophenyl)morpholine-4-carboxylate,
phenyl (2R)-2-(3-fluorophenyl)morpholine-4-carboxylate,
4-nitrophenyl (2R)-2-(3-fluorophenyl)morpholine-4-carboxylate,
methyl (2R)-2-(4-chlorophenyl)morpholine-4-carboxylate,
ethyl (2R)-2-(4-chlorophenyl)morpholine-4-carboxylate,
phenyl (2R)-2-(4-chlorophenyl)morpholine-4-carboxylate,
4-nitrophenyl (2R)-2-(4-chlorophenyl)morpholine-4-carboxylate,
methyl (2R)-2-(4-bromophenyl)morpholine-4-carboxylate,
ethyl (2R)-2-(4-bromophenyl)morpholine-4-carboxylate,
phenyl (2R)-2-(4-bromophenyl)morpholine-4-carboxylate,
4-nitrophenyl (2R)-2-(4-bromophenyl)morpholine-4-carboxylate,
methyl (2R)-2-(4-nitrophenyl)morpholine-4-carboxylate,
ethyl (2R)-2-(4-nitrophenyl)morpholine-4-carboxylate, phenyl (2R)-2-(4-nitrophenyl)morpholine-4-carboxylate,
4-nitrophenyl (2R)-2-(4-nitrophenyl)morpholine-4-carboxylate,
1-chloroethyl (2R)-2-(4-fluorophenyl)morpholine-4-carboxylate,
1-chloroethyl (2R)-2-(3-fluorophenyl)morpholine-4-carboxylate,
1-chloroethyl (2R)-2-(4-chlorophenyl)morpholine-4-carboxylate,
1-chloroethyl (2R)-2-(4-bromophenyl)morpholine-4-carboxylate,
1-chloroethyl (2R)-2-(4-nitrophenyl)morpholine-4-carboxylate,
(6R)-6-(4-benzyloxyphenyl)-4-(benzyl)morpholin-3-one,
(6R)-6-(4-benzyloxyphenyl)-4-(4-methoxybenzyl)morpholin-3-one,
(6R)-6-(4-benzyloxyphenyl)-4-(2,4-dimethoxybenzyl)morpholin-3-one,
(6R)-6-(4-benzyloxyphenyl)-4-((1R)-1-phenylethyl)morpholin-3-one,
(6R)-6-(4-benzyloxyphenyl)-4-((1S)-1-phenylethyl)morpholin-3-one,
(6R)-6-(4-benzyloxyphenyl)-4-(2-phenylethyl)morpholin-3-one,
(6R)-6-(4-benzyloxyphenyl)-4-(methyl)morpholin-3-one,
(6R)-6-(4-benzyloxyphenyl)-4-(ethyl)morpholin-3-one,
(6R)-6-(4-benzyloxyphenyl)-4-(tert-butyl)morpholin-3-one,
(6R)-6-(4-benzyloxyphenyl)-4-(allyl)morpholin-3-one,
(6R)-6-(4-benzyloxyphenyl)morpholin-3-one,
(2R)-2-(4-benzyloxyphenyl)-4-(benzyl)morpholine,
(2R)-2-(4-benzyloxyphenyl)-4-(4-methoxybenzyl)morpholine,
(2R)-2-(4-benzyloxyphenyl)-4-(2,4-dimethoxybenzyl)morpholine,
(2R)-2-(4-benzyloxyphenyl)-4-((1R)-1-phenylethyl)morpholine,
(2R)-2-(4-benzyloxyphenyl)-4-((1S)-1-phenylethyl)morpholine,
(2R)-2-(4-benzyloxyphenyl)-4-(2-phenylethyl)morpholine,
(2R)-2-(4-benzyloxyphenyl)-4-(methyl)morpholine,
(2R)-2-(4-benzyloxyphenyl)-4-(ethyl)morpholine,
(2R)-2-(4-benzyloxyphenyl)-4-(tert-butyl)morpholine,
(2R)-2-(4-benzyloxyphenyl)-4-(allyl)morpholine,
methyl (2R)-2-(4-benzyloxyphenyl)morpholine-4-carboxylate,
ethyl (2R)-2-(4-benzyloxyphenyl)morpholine-4-carboxylate,
1-chloroethyl (2R)-2-(4-benzyloxyphenyl)morpholine-4-carboxylate,
phenyl (2R)-2-(4-benzyloxyphenyl)morpholine-4-carboxylate,
4-nitrophenyl (2R)-2-(4-benzyloxyphenyl)morpholine-4-carboxylate,
(6R)-6-(4-methanesulfonyloxyphenyl)-4-(benzyl)morpholin-3-one,
(6R)-6-(4-methanesulfonyloxyphenyl)-4-(4-methoxybenzyl)morpholin-3-one,
(6R)-6-(4-methanesulfonyloxyphenyl)-4-(2,4-dimethoxybenzyl)morpholin-3-one,
(6R)-6-(4-methanesulfonyloxyphenyl)-4-((1R)-1-phenylethyl)morpholin-3-one,
(6R)-6-(4-methanesulfonyloxyphenyl)-4-((1S)-1-phenylethyl)morpholin-3-one,
(6R)-6-(4-methanesulfonyloxyphenyl)-4-(2-phenylethyl)morpholin-3-one,
(6R)-6-(4-methanesulfonyloxyphenyl)-4-(methyl)morpholin-3-one,
(6R)-6-(4-methanesulfonyloxyphenyl)-4-(ethyl)morpholin-3-one,
(6R)-6-(4-methanesulfonyloxyphenyl)-4-(tert-butyl)morpholin-3-one,
(6R)-6-(4-methanesulfonyloxyphenyl)-4-(allyl)morpholin-3-one,
(6R)-6-(4-methanesulfonyloxyphenyl)morpholin-3-one,
(2R)-2-(4-methanesulfonyloxyphenyl)-4-(benzyl)morpholine,
(2R)-2-(4-methanesulfonyloxyphenyl)-4-(4-methoxybenzyl)morpholine,
(2R)-2-(4-methanesulfonyloxyphenyl)-4-(2,4-dimethoxybenzyl)morpholine,
(2R)-2-(4-methanesulfonyloxyphenyl)-4-((1R)-1-phenylethyl)morpholine,
(2R)-2-(4-methanesulfonyloxyphenyl)-4-((1S)-1-phenylethyl)morpholine,
(2R)-2-(4-methanesulfonyloxyphenyl)-4-(2-phenylethyl)morpholine,
(2R)-2-(4-methanesulfonyloxyphenyl)-4-(methyl)morpholine,
(2R)-2-(4-methanesulfonyloxyphenyl)-4-(ethyl)morpholine,
(2R)-2-(4-methanesulfonyloxyphenyl)-4-(tert-butyl)morpholine,
(2R)-2-(4-methanesulfonyloxyphenyl)-4-(allyl)morpholine,
methyl (2R)-2-(4-methanesulfonyloxyphenyl)morpholine-4-carboxylate,
ethyl (2R)-2-(4-methanesulfonyloxyphenyl)morpholine-4-carboxylate,
1-chloroethyl (2R)-2-(4-methanesulfonyloxyphenyl)morpholine-4-carboxylate,
phenyl (2R)-2-(4-methanesulfonyloxyphenyl)morpholine-4-carboxylate,
4-nitrophenyl (2R)-2-(4-methanesulfonyloxyphenyl)morpholine-4-carboxylate,
(6R)-6-(4-benzenesulfonyloxyphenyl)-4-(benzyl)morpholin-3-one,
(6R)-6-(4-benzenesulfonyloxyphenyl)-4-(4-methoxybenzyl)morpholin-3-one,
(6R)-6-(4-benzenesulfonyloxyphenyl)-4-(2,4-dimethoxybenzyl)morpholin-3-one,
(6R)-6-(4-benzenesulfonyloxyphenyl)-4-((1R)-1-phenylethyl)morpholin-3-one,
(6R)-6-(4-benzenesulfonyloxyphenyl)-4-((1S)-1-phenylethyl)morpholin-3-one,
(6R)-6-(4-benzenesulfonyloxyphenyl)-4-(2-phenylethyl)morpholin-3-one,
(6R)-6-(4-benzenesulfonyloxyphenyl)-4-(methyl)morpholin-3-one,
(6R)-6-(4-benzenesulfonyloxyphenyl)-4-(ethyl)morpholin-3-one,
(6R)-6-(4-benzenesulfonyloxyphenyl)-4-(tert-butyl)morpholin-3-one,
(6R)-6-(4-benzenesulfonyloxyphenyl)-4-(allyl)morpholin-3-one,
(6R)-6-(4-benzenesulfonyloxyphenyl)morpholin-3-one,
(2R)-2-(4-benzenesulfonyloxyphenyl)-4-(benzyl)morpholine,
(2R)-2-(4-benzenesulfonyloxyphenyl)-4-(4-methoxybenzyl)morpholine,
(2R)-2-(4-benzenesulfonyloxyphenyl)-4-(2,4-dimethoxybenzyl)morpholine,
(2R)-2-(4-benzenesulfonyloxyphenyl)-4-((1R)-1-phenylethyl)morpholine,
(2R)-2-(4-benzenesulfonyloxyphenyl)-4-((1S)-1-phenylethyl)morpholine, (2R)-2-(4-benzenesulfonyloxyphenyl)-4-(2-phenylethyl) morpholine,
(2R)-2-(4-benzenesulfonyloxyphenyl)-4-(methyl)morpholine,
(2R)-2-(4-benzenesulfonyloxyphenyl)-4-(ethyl)morpholine,
(2R)-2-(4-benzenesulfonyloxyphenyl)-4-(tert-butyl)morpholine,
(2R)-2-(4-benzenesulfonyloxyphenyl)-4-(allyl)morpholine,
methyl (2R)-2-(4-benzenesulfonyloxyphenyl)morpholine-4-carboxylate,
ethyl (2R)-2-(4-benzenesulfonyloxyphenyl)morpholine-4-carboxylate,
1-chloroethyl (2R)-2-(4-benzenesulfonyloxyphenyl)morpholine-4-carboxylate,
phenyl (2R)-2-(4-benzenesulfonyloxyphenyl)morpholine-4-carboxylate,
4-nitrophenyl (2R)-2-(4-benzenesulfonyloxyphenyl)morpholine-4-carboxylate,
(6R)-6-(4-(4-toluenesulfonyloxy)phenyl)-4-(benzyl)morpholin-3-one,
(6R)-6-(4-(4-toluenesulfonyloxy)phenyl)-4-(4-methoxybenzyl)morpholin-3-one,
(6R)-6-(4-(4-toluenesulfonyloxy)phenyl)-4-(2,4-dimethoxybenzyl)morpholin-3-one,
(6R)-6-(4-(4-toluenesulfonyloxy)phenyl)-4-((1R)-1-phenylethyl)morpholin-3-one,
(6R)-6-(4-(4-toluenesulfonyloxy)phenyl)-4-((1S)-1-phenylethyl)morpholin-3-one,
(6R)-6-(4-(4-toluenesulfonyloxy)phenyl)-4-(2-phenylethyl) morpholin-3-one,
(6R)-6-(4-(4-toluenesulfonyloxy)phenyl)-4-(methyl)morpholin-3-one,
(6R)-6-(4-(4-toluenesulfonyloxy)phenyl)-4-(ethyl)morpholin-3-one,
(6R)-6-(4-(4-toluenesulfonyloxy)phenyl)-4-(tert-butyl)morpholin-3-one,
(6R)-6-(4-(4-toluenesulfonyloxy)phenyl)-4-(allyl)morpholin-3-one,
(6R)-6-(4-(4-toluenesulfonyloxy)phenyl)morpholin-3-one,
(2R)-2-(4-(4-toluenesulfonyloxy)phenyl)-4-(benzyl)morpholine,
(2R)-2-(4-(4-toluenesulfonyloxy)phenyl)-4-(4-methoxybenzyl)morpholine,
(2R)-2-(4-(4-toluenesulfonyloxy)phenyl)-4-(2,4-dimethoxybenzyl)morpholine,
(2R)-2-(4-(4-toluenesulfonyloxy)phenyl)-4-((1R)-1-phenylethyl)morpholine,
(2R)-2-(4-(4-toluenesulfonyloxy)phenyl)-4-((1S)-1-phenylethyl)morpholine,
(2R)-2-(4-(4-toluenesulfonyloxy)phenyl)-4-(2-phenylethyl) morpholine,
(2R)-2-(4-(4-toluenesulfonyloxy)phenyl)-4-(methyl)morpholine,
(2R)-2-(4-(4-toluenesulfonyloxy)phenyl)-4-(ethyl)morpholine,
(2R)-2-(4-(4-toluenesulfonyloxy)phenyl)-4-(tert-butyl)morpholine,
(2R)-2-(4-(4-toluenesulfonyloxy)phenyl)-4-(allyl)morpholine,
methyl (2R)-2-(4-(4-toluenesulfonyloxy)phenyl)morpholine-4-carboxylate,
ethyl (2R)-2-(4-(4-toluenesulfonyloxy)phenyl)morpholine-4-carboxylate,
1-chloroethyl (2R)-2-(4-(4-toluenesulfonyloxy)phenyl)morpholine-4-carboxylate,
phenyl (2R)-2-(4-(4-toluenesulfonyloxy)phenyl)morpholine-4-carboxylate, and
4-nitrophenyl (2R)-2-(4-(4-toluenesulfonyloxy)phenyl)morpholine-4-carboxylate.

Moreover, the optically active 2-ethanolamine compound can also be produced according to the following Scheme 7 (S-form) or Scheme 8 (R-form).

Scheme 7

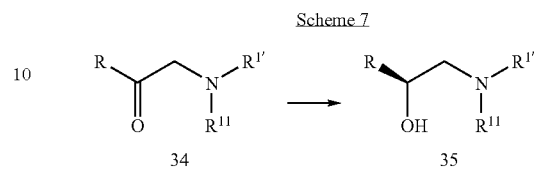

Scheme 8

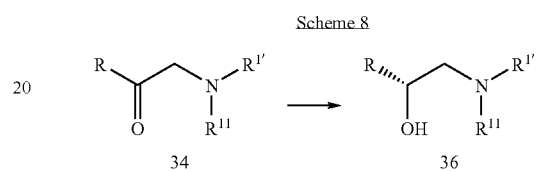

wherein the symbols in each scheme are as defined above.

In the step of Scheme 7, a compound of the formula 35 is obtained by reacting a compound of the formula 34 with isopropanol or formic acid in a solvent in the presence of a Ru catalyst and an optically active amino alcohol or amine ligand.

By this step, an optically active 2-ethanolamine compound (S-form), which is the compound of the formula 35 (when $R^{11}$ is a hydrogen atom, this compound becomes a compound of the formula 5), can be produced.

Scheme 8 can be performed by a step similar to that in Scheme 7, except that an optical isomer of the optically active amino alcohol or amine ligand is used instead of the optically active amino alcohol or amine ligand, whereby an optically active 2-ethanolamine compound (R-form), which is a compound of the formula 36 (when $R^{11}$ is a hydrogen atom, this compound becomes a compound of the formula 25), can be produced.

As the representative examples of the Ru catalyst in Scheme 7 and Scheme 8, dichloro(p-cymene)ruthenium(II) dimer, benzeneruthenium(II) chloride dimer and the like can be mentioned. As the representative examples of the optically active amino alcohol ligand, (1S,2R)-cis-1-aminoindan-2-ol, an optical isomer thereof and the like can be mentioned. As the representative examples of the optically active amine ligand, (R,R)-DPEN, (R,R)-MsDPEN, (R,R)-TsDPEN, an optically active form thereof and the like can be mentioned. As the hydrogen source for this reaction, isopropanol, formic acid and the like can be mentioned. The reaction can be carried out in the presence of potassium hydroxide, triethylamine and the like.

The compound of the formula 34 as a starting material is a novel compound. Particularly, a compound wherein R is a phenyl having 1 to 3 substituents selected from halogen, $C_1$-$C_6$ alkyl, substituted $C_1$-$C_6$ alkyl, $C_1$-$C_6$ alkoxy, substituted $C_1$-$C_6$ alkoxy, nitro aralkyloxy, $C_1$-$C_6$ alkylsulfonyloxy, arylsulfonyloxy and $C_1$-$C_6$ alkyl-substituted arylsulfonyloxy is preferable, and a compound wherein R is a phenyl having 1 to 3 substituents selected from fluorine, chlorine, bromine, nitro, benzyloxy, methanesulfonyloxy, benzenesulfonyloxy and toluenesulfonyloxy is more preferable. Specifically, the following compounds can be mentioned:

2-(benzylamino)-1-(4-fluorophenyl)ethanone,
2-(4-methoxybenzylamino)-1-(4-fluorophenyl)ethanone,
2-(2,4-dimethoxybenzylamino)-1-(4-fluorophenyl)ethanone,
2-((1R)-1-phenylethylamino)-1-(4-fluorophenyl)ethanone,
2-((1S)-1-phenylethylamino)-1-(4-fluorophenyl)ethanone,
2-(2-phenylethylamino)-1-(4-fluorophenyl)ethanone,
2-(methylamino)-1-(4-fluorophenyl)ethanone,
2-(ethylamino)-1-(4-fluorophenyl)ethanone,
2-(tert-butylamino)-1-(4-fluorophenyl)ethanone,
2-(allylamino)-1-(4-fluorophenyl)ethanone,
2-amino-1-(4-fluorophenyl)ethanone,
2-(benzylamino)-1-(3-fluorophenyl)ethanone,
2-(4-methoxybenzylamino)-1-(3-fluorophenyl)ethanone,
2-(2,4-dimethoxybenzylamino)-1-(3-fluorophenyl)ethanone,
2-((1R)-1-phenylethylamino)-1-(3-fluorophenyl)ethanone,
2-((1S)-1-phenylethylamino)-1-(3-fluorophenyl)ethanone,
2-(2-phenylethylamino)-1-(3-fluorophenyl)ethanone,
2-(methylamino)-1-(3-fluorophenyl)ethanone,
2-(ethylamino)-1-(3-fluorophenyl)ethanone,
2-(tert-butylamino)-1-(3-fluorophenyl)ethanone,
2-(allylamino)-1-(3-fluorophenyl)ethanone,
2-amino-1-(3-fluorophenyl)ethanone,
2-(benzylamino)-1-(4-chlorophenyl)ethanone,
2-(4-methoxybenzylamino)-1-(4-chlorophenyl)ethanone,
2-(2,4-dimethoxybenzylamino)-1-(4-chlorophenyl)ethanone,
2-((1R)-1-phenylethylamino)-1-(4-chlorophenyl)ethanone,
2-((1S)-1-phenylethylamino)-1-(4-chlorophenyl)ethanone,
2-(2-phenylethylamino)-1-(4-chlorophenyl)ethanone,
2-(methylamino)-1-(4-chlorophenyl)ethanone,
2-(ethylamino)-1-(4-chlorophenyl)ethanone,
2-(tert-butylamino)-1-(4-chlorophenyl)ethanone,
2-(allylamino)-1-(4-chlorophenyl)ethanone,
2-amino-1-(4-chlorophenyl)ethanone,
2-(benzylamino)-1-(4-bromophenyl)ethanone,
2-(4-methoxybenzylamino)-1-(4-bromophenyl)ethanone,
2-(2,4-dimethoxybenzylamino)-1-(4-bromophenyl)ethanone,
2-((1R)-1-phenylethylamino)-1-(4-bromophenyl)ethanone,
2-((1S)-1-phenylethylamino)-1-(4-bromophenyl)ethanone,
2-(2-phenylethylamino)-1-(4-bromophenyl)ethanone,
2-(methylamino)-1-(4-bromophenyl)ethanone,
2-(ethylamino)-1-(4-bromophenyl)ethanone,
2-(tert-butylamino)-1-(4-bromophenyl)ethanone,
2-(allylamino)-1-(4-bromophenyl)ethanone,
2-amino-1-(4-bromophenyl)ethanone,
2-(benzylamino)-1-(4-nitrophenyl)ethanone,
2-(4-methoxybenzylamino)-1-(4-nitrophenyl)ethanone,
2-(2,4-dimethoxybenzylamino)-1-(4-nitrophenyl)ethanone,
2-((1R)-1-phenylethylamino)-1-(4-nitrophenyl)ethanone,
2-((1S)-1-phenylethylamino)-1-(4-nitrophenyl)ethanone,
2-(2-phenylethylamino)-1-(4-nitrophenyl)ethanone,
2-(methylamino)-1-(4-nitrophenyl)ethanone,
2-(ethylamino)-1-(4-nitrophenyl)ethanone,
2-(tert-butylamino)-1-(4-nitrophenyl)ethanone,
2-(allylamino)-1-(4-nitrophenyl)ethanone,
2-amino-1-(4-nitrophenyl)ethanone,
2-(benzylamino)-1-(4-benzyloxyphenyl)ethanone,
2-(4-methoxybenzylamino)-1-(4-benzyloxyphenyl)ethanone,
2-(2,4-dimethoxybenzylamino)-1-(4-benzyloxyphenyl)ethanone,
2-((1R)-1-phenylethylamino)-1-(4-benzyloxyphenyl)ethanone,
2-((1S)-1-phenylethylamino)-1-(4-benzyloxyphenyl)ethanone,
2-(2-phenylethylamino)-1-(4-benzyloxyphenyl)ethanone,
2-(methylamino)-1-(4-benzyloxyphenyl)ethanone,
2-(ethylamino)-1-(4-benzyloxyphenyl)ethanone,
2-(tert-butylamino)-1-(4-benzyloxyphenyl)ethanone,
2-(allylamino)-1-(4-benzyloxyphenyl)ethanone,
2-amino-1-(4-benzyloxyphenyl)ethanone,
2-(benzylamino)-1-(4-methanesulfonyloxyphenyl)ethanone,
2-(4-methoxybenzylamino)-1-(4-methanesulfonyloxyphenyl)ethanone,
2-(2,4-dimethoxybenzylamino)-1-(4-methanesulfonyloxyphenyl)ethanone,
2-((1R)-1-phenylethylamino)-1-(4-methanesulfonyloxyphenyl)ethanone,
2-((1S)-1-phenylethylamino)-1-(4-methanesulfonyloxyphenyl)ethanone,
2-(2-phenylethylamino)-1-(4-methanesulfonyloxyphenyl)ethanone,
2-(methylamino)-1-(4-methanesulfonyloxyphenyl)ethanone,
2-(ethylamino)-1-(4-methanesulfonyloxyphenyl)ethanone,
2-(tert-butylamino)-1-(4-methanesulfonyloxyphenyl)ethanone,
2-(allylamino)-1-(4-methanesulfonyloxyphenyl)ethanone,
2-amino-1-(4-methanesulfonyloxyphenyl)ethanone,
2-(benzylamino)-1-(4-benzenesulfonyloxyphenyl)ethanone,
2-(4-methoxybenzylamino)-1-(4-benzenesulfonyloxyphenyl)ethanone,
2-(2,4-dimethoxybenzylamino)-1-(4-benzenesulfonyloxyphenyl)ethanone,
2-((1R)-1-phenylethylamino)-1-(4-benzenesulfonyloxyphenyl)ethanone,
2-((1S)-1-phenylethylamino)-1-(4-benzenesulfonyloxyphenyl)ethanone,
2-(2-phenylethylamino)-1-(4-benzenesulfonyloxyphenyl)ethanone,
2-(methylamino)-1-(4-benzenesulfonyloxyphenyl)ethanone,
2-(ethylamino)-1-(4-benzenesulfonyloxyphenyl)ethanone,
2-(tert-butylamino)-1-(4-benzenesulfonyloxyphenyl)ethanone,
2-(allylamino)-1-(4-benzenesulfonyloxyphenyl)ethanone,
2-amino-1-(4-benzenesulfonyloxyphenyl)ethanone,
2-(benzylamino)-1-(4-(4-toluenesulfonyloxy)phenyl)ethanone,
2-(4-methoxybenzylamino)-1-(4-(4-toluenesulfonyloxy)phenyl)ethanone,
2-(2,4-dimethoxybenzylamino)-1-(4-(4-toluenesulfonyloxy)phenyl)ethanone,
2-((1R)-1-phenylethylamino)-1-(4-(4-toluenesulfonyloxy)phenyl)ethanone,
2-((1S)-1-phenylethylamino)-1-(4-(4-toluenesulfonyloxy)phenyl)ethanone,
2-(2-phenylethylamino)-1-(4-(4-toluenesulfonyloxy)phenyl)ethanone,
2-(methylamino)-1-(4-(4-toluenesulfonyloxy)phenyl)ethanone,
2-(ethylamino)-1-(4-(4-toluenesulfonyloxy)phenyl)ethanone,
2-(tert-butylamino)-1-(4-(4-toluenesulfonyloxy)phenyl)ethanone,
2-(allylamino)-1-(4-(4-toluenesulfonyloxy)phenyl)ethanone, and
2-amino-1-(4-(4-toluenesulfonyloxy)phenyl)ethanone.

The compound of the formula 34 can be produced by a method similar to that described in J. Chem. Soc. Perkin Trans. 1, 16, 1916, (2001).

In the present invention, 3-oxo-3-(pyrimidin-4-yl)propionate can be produced according to the following Scheme 9 from orotic acid as a starting material.

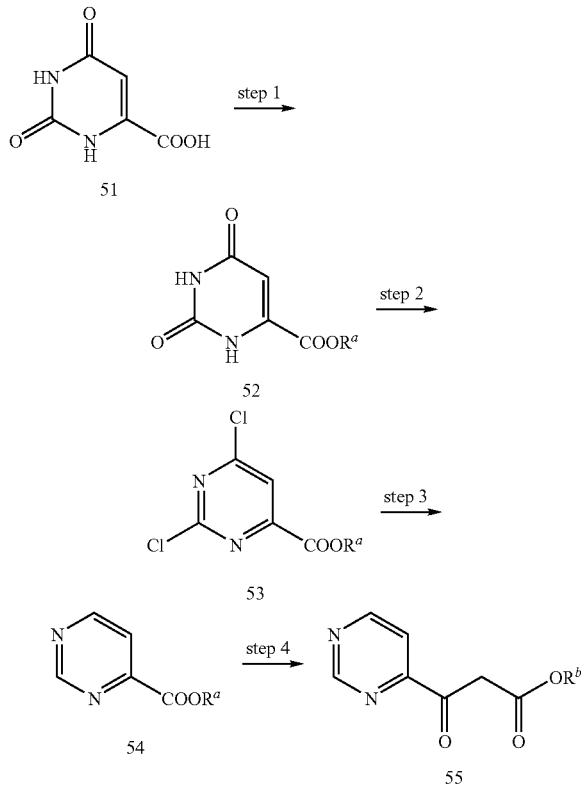

wherein each symbol is as defined above.

In step 1, a compound of the formula 52 is obtained by reacting orotic acid of the formula 51 with an alkylating agent in a solvent in the presence of a base.

As the alkylating agent, ethyl iodide, methyl iodide, ethyl bromide, methyl bromide, dimethyl sulfate, diethyl sulfate, methyl benzenesulfonate, methyl toluene-2-sulfonate, methyl toluene-4-sulfonate, ethyl benzenesulfonate, ethyl toluene-2-sulfonate, ethyl toluene-4-sulfonate and the like can be mentioned.

The amount of the alkylating agent to be used is generally 0.1 mol to 100 mol, preferably 0.8 mol to 2 mol, relative to 1 mol of the compound of the formula 51.

As the base, 1,8-diazabicyclo[5.4.0]undec-7-ene, 1,5-diazabicyclo[4.3.0]non-5-ene and the like can be mentioned.

The amount of the base to be used is generally 0.1 mol to 10 mol, preferably 0.8 mol to 1.2 mol, relative to 1 mol of the compound of the formula 51.

As the solvent, N,N-dimethylformamide, N,N-dimethylacetamide, N-methylpyrrolidone, dimethyl sulfoxide etc., mixed solvents of these and the like can be mentioned.

In this step, the reaction proceeds at 40° C. to 100° C. for 0.1 hr to 10 hr.

In step 2, a compound of the formula 53 is obtained by heating the compound of the formula 52 under reflux with a chlorinating agent.

As the chlorinating agent, phosphorus oxychloride, phosphorus trichloride, phosphorus pentachloride, Vilsmeier intermediates (phosphorus oxychloride+dimethylformamide), phosphorus oxychloride+N-methylpyrrolidone, thionyl chloride, sulfuryl chloride and the like can be mentioned.

The amount of the chlorinating agent to be used is generally 1.5 mol to 10 mol, preferably 2 mol to 3 mol, relative to 1 mol of the compound of the formula 52.

The chlorinating agent may be used in the presence of an ammonium salt and as the ammonium salt, benzyltriethylammonium chloride, tetraethylammonium chloride and the like can be mentioned.

The amount of the ammonium salt to be used is generally 0.1 mol to 10 mol, preferably 0.1 mol to 2 mol, relative to 1 mol of the compound of the formula 52.

This step may be performed in a solvent, and as the solvent, tetrahydrofuran, 1,4-dioxane, 1,2-dimethoxyethane, toluene, xylene, benzene, acetonitrile, propionitrile etc., mixed solvents thereof and the like can be mentioned.

In this step, the reaction proceeds by heating under reflux at 60° C. to 90° C. for 0.5 hr to 10 hr.

In step 3, a compound of the formula 54 is obtained by dechlorinating the compound of the formula 53 in the presence of a base.

The dechlorination is preferably carried out by catalytic reduction and as the reduction catalyst, palladium-carbon, palladium hydroxide and the like can be mentioned.

The amount of the reduction catalyst to be used is generally 0.01 mol to 10 mol, preferably 0.1 mol to 2 mol, relative to 1 mol of the compound of the formula 53.

As the base, triethylamine, N,N-diethylaniline, N,N-dimethylaniline, diisopropylethylamine, tributylamine, N-ethylpiperidine, N-methylmorpholine, 1,8-diazabicyclo[5.4.0]undec-7-ene, 1,5-diazabicyclo[4.3.0]non-5-ene and the like can be mentioned.

The amount of the base to be used is generally 2 mol to 20 mol, preferably 2 mol to 5 mol, relative to 1 mol of the compound of the formula 53.

The above-mentioned catalytic reduction is carried out under a hydrogen atmosphere.

This step may be performed in a solvent, and as the solvent, tetrahydrofuran, 1,4-dioxane, 1,2-dimethoxyethane, benzene, toluene, xylene, isopropyl alcohol, tert-butyl alcohol, tert-amyl alcohol, ethyl acetate, butyl acetate etc., mixed solvents thereof and the like can be mentioned.

In this step, the reaction proceeds at 0° C. to 50° C. for 0.1 hr to 20 hr.

In step 4, a compound of the formula 55 is obtained by reacting the compound of the formula 54 with an acetate in the presence of a base.

The amount of the acetate to be used is generally 0.8 mol to 10 mol, preferably 0.8 mol to 2 mol, relative to 1 mol of the compound of the formula 54.

As the base, sodium hydride, potassium hydride, or sodium alkoxide or potassium alkoxide derived from ROH (R is $C_1$-$C_{12}$ alkyl such as methyl, ethyl, tert-butyl, tert-amyl, 3,7-dimethyl-3-octyl etc.), lithium diisopropylamide, lithium (bistrimethylsilyl)amide, sodium (bistrimethylsilyl)amide, potassium (bistrimethylsilyl)amide and the like can be mentioned.

The amount of the base to be used is generally 1.5 mol to 10 mol, preferably 1.5 mol to 3 mol, relative to 1 mol of the compound of the formula 54.

This step may be performed in a solvent, and as the solvent, ethanol, diethyl ether, toluene, hexane, heptane, tetrahydrofuran, 1,4-dioxane, 1,2-dimethoxyethane, dimethylformamide, N-methylpyrrolidone, N,N-dimethylacetamide, dimethylimidazolinone, benzene, toluene, xylene etc., mixed solvents thereof and the like can be mentioned.

In this step, the reaction proceeds at −80° C. to 100° C. for 0.1 hr to 10 hr.

While orotic acid (the compound of the formula 51) and ester thereof (the compound of the formula 52) include keto-enol tautomers, any isomers and mixtures can be used for the production method of the present invention.

Of the above-mentioned steps 1-4, steps 1-3 are all novel steps.

Ethyl 3-oxo-3-(pyrimidin-4-yl)propionate produced by such steps is led to 2-(2-arylmorpholin-4-yl)-1-methyl-1H-[4,4']bipyrimidinyl-6-one having a tau protein kinase 1 inhibitory activity and useful as a therapeutic drug for Alzheimer's disease and the like, by the following steps.

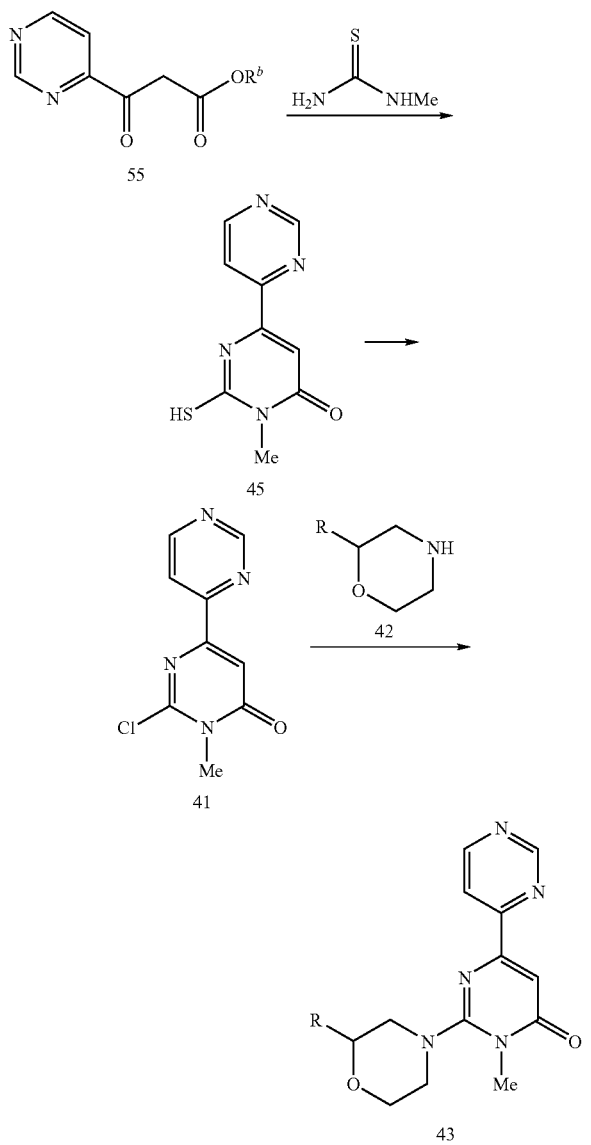

wherein each symbol is as defined above.

EXAMPLES

The present invention is explained more specifically with reference to examples. However, the scope of the present invention is not limited to the following examples. The compound number in the examples corresponds to that in the table above.

Example 1

(1) Synthesis of 2-chloro-(1S)-1-(4-fluorophenyl) ethanol

A borane-tetrahydrofuran complex (1.0 M solution in tetrahydrofuran, 60 ml, 60 mmol) was added dropwise over 15 min to a (S)—CBS solution ((S)-2-methyl-CBS-oxazaborolidine, 12 ml, 1.0 M solution in toluene) at −30° C., and the mixture was stirred for 15 min. A solution of 4-fluorophenacyl chloride (10.4 g, 60 mmol) in dichloromethane (16 ml) was added dropwise over 60 min keeping the temperature −32° C. to −28° C. After stirring for 1 hr, the solution was allowed to warm to room temperature, and methanol (20 ml) was added slowly and then 1 M hydrochloric acid (120 ml) was added dropwise over 10 min. The reaction mixture was filtered after stirring for 40 min, and the filtrate was extracted with ethyl acetate. The combined organic layer was washed successively with 1 M hydrochloric acid and brine, and dried over anhydrous sodium sulfate. The organic layer was concentrated to give 2-chloro-(1S)-1-(4-fluorophenyl)ethanol (10.4 g) as a colorless oil.

(2) Synthesis of (2S)-2-(4-fluorophenyl)oxirane 1.6 M aqueous sodium hydroxide solution (50 ml) was added to a solution of 2-chloro-(1S)-1-(4-fluorophenyl)ethanol (10.4 g) in diethyl ether (40 ml), and the mixture was stirred at room temperature for 5 hrs. The organic layer was separated and the aqueous layer was extracted with diethyl ether. The combined organic layer was washed with brine and dried over anhydrous sodium sulfate. The solvent was evaporated to give (2S)-2-(4-fluorophenyl)oxirane (8.28 g) as a colorless oil.

(3) Synthesis of (1S)-1-(4-fluorophenyl)-2-(benzylamino)ethanol

A mixture of (2S)-2-(4-fluorophenyl)oxirane (8.28 g) and benzylamine (19.3 g, 180 mmol) was heated at 80° C. for 4 hrs. The reaction mixture was poured into water and extracted with ethyl acetate. The combined organic layer was washed with brine and dried over anhydrous sodium sulfate. After removal of the solvent, the precipitate was collected by filtration and washed with hexane to give (1S)-1-(4-fluorophenyl)-2-(benzylamino)ethanol (8.3 g) as white crystals (yield 57% for 3 steps).

The analysis of the optical purity of this compound was performed using an optically active column (CHIRAL PAK AS-H, solvent: heptane/isopropanol (containing 0.1% diethylamine)). The above-mentioned analysis conditions were determined based on the analysis conditions of racemic 1-(4-fluorophenyl)-2-(benzylamino)ethanol.

Racemic 1-(4-fluorophenyl)-2-(benzylamino)ethanol was synthesized by a method similar to that described in J. Chem. Soc. Perkin Trans. 1, 16, 1916 (2001), as mentioned below.

Synthetic Method of 1-(4-fluorophenyl)-2-(benzylamino)ethanol

To a solution of benzylamine (1.29 g, 12.1 mmol) in methylene chloride was added triethylamine (7.6 g, 75.0 mmol), and then 2-bromo-1-(4-fluorophenyl)ethanone (3.27 g, 15.1 mmol) was added thereto. Aqueous ammonium chloride solution was added to the reaction mixture, and the mixture was partitioned. The organic layer was dried over sodium sulfate and concentrated to give crude 2-(benzylamino)-1-(4-fluorophenyl)ethanone (1.85 g) as an oil. The oil (1.50 g) was dissolved in a mixed solvent of methanol (9 mL) and water (1 mL), and sodium borohydrogen (0.8 g) was added at room temperature. The reaction mixture was concentrated and extracted with tert-butyl methyl ether, and the organic layer was concentrated. Isopropyl acetate (4 mL) and heptane (4 mL) were added to the residue, and the mixture was refluxed. The precipitated crystals were collected by filtration and dried to give racemic 1-(4-fluorophenyl)-2-(benzylamino) ethanol (0.21 g). 1-(4-fluorophenyl)-2-(benzylamino)ethanol: $^1$H-NMR (CDCl$_3$) δ: 2.70-2.73 (1H, m), 2.91-2.94 (1H, m), 3.80-3.88 (2H, m), 4.68-4.71 (1H, m), 7.00-7.52 (9H, m)

Example 2

(1) Synthesis of (6S)-6-(4-fluorophenyl)-4-(benzyl) morpholin-3-one

A solution of chloroacetyl chloride (4.3 g, 3.4 ml, 38 mmol) in dichloromethane (20 ml) was added dropwise over 30 min to the ice-cooled mixture of a solution of (1S)-1-(4-fluorophenyl)-2-(benzylamino)ethanol (8.3 g, 34 mmol) in dichloromethane (100 ml) and 1N aqueous sodium hydroxide solution (40 ml, 40 mmol), and the mixture was stirred for 1 hr at same temperature. The resulting solution was washed successively with 0.5 M hydrochloric acid, saturated aqueous sodium hydrogencarbonate solution and brine, and dried over anhydrous magnesium sulfate. The solvent was evaporated under reduced pressure to give (1S)-1-(4-fluorophenyl)-2-(N-benzyl-N-chloroacetylamino)ethanol. Potassium hydroxide (2.2 g, 39 mmol) was added to a solution of the obtained compound in isopropyl alcohol (60 ml), and the mixture was stirred for 4 hrs. The solvent was evaporated in vacuo and the residue was partitioned between water and ethyl acetate. The organic layer was washed with brine and dried over anhydrous magnesium sulfate. The solvent was evaporated under reduced pressure to give (6S)-6-(4-fluorophenyl)-4-(benzyl) morpholin-3-one (9.7 g) as a yellow oil.

(2) Synthesis of (2S)-2-(4-fluorophenyl)-4-(benzyl) morpholine

A solution of (6S)-6-(4-fluorophenyl)-4-(benzyl)morpholin-3-one (9.7 g) in tetrahydrofuran (30 ml) was added dropwise over 30 min to lithium aluminum hydride (2.6 g 70 mmol) in tetrahydrofuran (200 ml) at room temperature, and the reaction mixture was refluxed for 3 hrs. The reaction was quenched by addition of water (10.6 ml) and 15% aqueous sodium hydroxide solution (2.6 ml) at 0° C. The reaction mixture was filtered and the filtrate was concentrated to give (2S)-2-(4-fluorophenyl)-4-(benzyl)morpholine (9.05 g, yield 98% for 2 steps) as a colorless oil.
$^1$H-NMR (CDCl$_3$) δ: 2.07 (1H, dd, J=10.8, 10.8 Hz), 2.27 (1H, ddd, J=11.4, 11.4, 3.3 Hz), 2.75 (1H, m), 2.87 (1H, m), 3.54 (3H, s), 3.82 (1H, ddd, J=11.4, 11.4, 2.4 Hz), 3.82 (1H, dd, J=11.4, 2.1 Hz), 4.54 (1H, dd, J=11.4, 2.1 Hz), 6.96-7.03 (2H, m), 7.23-7.33 (7H, m).

(3) Synthesis of (2S)-2-(4-fluorophenyl)morpholine Hydrochloride

1-Chloroethyl chloroformate was added to a solution of (2S)-2-(4-fluorophenyl)-4-(benzyl)morpholine (9.05 g) in dichloroethane (160 ml) at 70° C. After the reaction mixture was refluxed for 2 hrs, the solvent was evaporated under reduced pressure. Methanol (10 ml) was added to the residue, and then the mixture was refluxed for 30 min. The solvent was evaporated and the precipitate was collected by filtration to give (2S)-2-(4-fluorophenyl)morpholine hydrochloride (5.3 g, 73%) as white crystals.
$^1$H-NMR (d-DMSO) δ: 2.99 (1H, dd, J=12.0, 12.0 Hz), 3.10 (1H, ddd, J=12.0, 12.0, 3.6 Hz), 3.22-3.26 (1H, m), 3.32 (3H, s), 3.37-3.42 (1H, m), 3.89-3.97 (1H, m), 4.11 (1H, dd, J=12.3, 3.3 Hz), 4.77 (1H, m), 7.20-7.26 (2H, m), 7.42-7.47 (2H, m).

Example 3

(1) Synthesis of (6S)-6-(4-fluorophenyl)-4-(benzyl) morpholin-3-one

To a suspension of (1S)-1-(4-fluorophenyl)-2-(benzylamino)ethanol (22.0 g, 89.69 mmol) in toluene (100 mL) was added dropwise over 1 hr a solution of chloroacetyl chloride (9.3 mL, 116.6 mmol) in toluene (30 mL) at 5-15° C. After stirring for 2 hrs, a solution of triethylamine (17.4 mL, 123.7 mmol) in toluene (20 mL) was added dropwise over 15 min to the mixture at 10-15° C. The mixture was stirred for 17 hrs at room temperature. After HPLC analysis to confirm a disappearance of the aminoethanol, the mixture was cooled to 2° C., and sodium methoxide (52 g, 269.07 mmol, 28% methanol solution) was added dropwise over 15 min. The mixture was stirred at 2-5° C. for 9 hrs, and water (60 mL) was added. The organic layer was separated and washed successively with 0.5N hydrochloric acid and saturated aqueous sodium hydrogencarbonate solution. The solvent was evaporated under reduced pressure to give (6S)-6-(4-fluorophenyl)-4-(benzyl)morpholin-3-one (27.78 g) as a yellow oil.

(2) Synthesis of (2S)-2-(4-fluorophenyl)-4-(benzyl) morpholine

To a solution of (6S)-6-(4-fluorophenyl)-4-(benzyl)morpholin-3-one (1.16 g) in tetrahydrofuran (10 mL) was added dropwise over 15 min a solution of sodium bis(2-methoxyethoxy)aluminum hydride (70% in toluene, 3.2 mL, 11.4 mmol) in tetrahydrofuran (5 ml) at 65° C., and the reaction mixture was refluxed over 1.5 hrs. After HPLC analysis to confirm a disappearance of the morpholin-3-one, the reaction was quenched by addition of water (0.6 mL), 15% aqueous sodium hydroxide solution (0.6 mL) and water (1.8 mL) at 0° C. The reaction mixture was filtered and the filtrate was concentrated. To the residue was added ethyl acetate and wash successively with 15% aqueous sodium hydroxide solution and water. The solvent was evaporated to give (2S)-2-(4-fluorophenyl)-4-(benzyl)morpholine (1.02 g, 92% yield) as a colorless oil.

(3) Synthesis of (2S)-2-(4-fluorophenyl)morpholine

To a solution of (2S)-2-(4-fluorophenyl)-4-(benzyl)morpholine (1.00 g, 3.67 mmol) in toluene (10 mL) was added a solution of ethyl chloroformate (0.39 mL, 4.04 mmol) in toluene (5 mL) at 89° C. The mixture was stirred for 3 hrs and the solvent was evaporated to give ethyl (S)-2-(4-fluorophenyl)morpholine-4-carboxylate (1.17 g) as a black oil.
$^1$H-NMR (CDCl$_3$) δ: 1.28 (t, 3H, J=7 Hz), 2.7 (1H, br), 3.1 (1H, br), 3.65-3.69 (1H, m), 4.0-4.1 (2H, br), 4.19 (q, 2H, J=7 Hz), 4.4 (1H, br), 4.5 (1H, br), 7.0-7.4 (4H, m).

From the above residue, 100 mg compound was collected and treated with aqueous potassium hydroxide solution (0.5 mL) and ethanol (2 mL) at 80° C. After HPLC analysis to confirm a disappearance of the starting morpholine, 5N hydrochloric acid (2 mL) was added and the mixture was washed with ethyl acetate. The aqueous layer was treated with aqueous potassium hydroxide solution and extracted with ethyl acetate. The solvent was evaporated to give (2S)-2-(4-fluorophenyl)morpholine (35 mg, yield 65% from (2S)-2-(4-fluorophenyl)-4-(benzyl)morpholine) as a colorless solid.

$^1$H-NMR (CDCl$_3$) δ: 2.75 (1H, dd, J=12.0, 12.0 Hz), 2.90 (1H, m), 2.95-3.05 (2H, m), 3.73-3.77 (1H, m), 4.01-4.04 (1H, m), 4.44-4.47 (1H, m), 7.00-7.04 (2H, m), 7.31-7.34 (2H, m).

Example 4

(1) Synthesis of (2S)-2-bromo-1-(4-bromophenyl)ethanol (S)—CBS ((S)-2-methyl-CBS-oxazaborolidine, 50 ml, manufactured by Aldrich, 1.0 M solution in toluene) was cooled to −30° C., and borane-tetrahydrofuran complex (270 ml, 270 mmol, 1.0 M solution in tetrahydrofuran) was added dropwise over 15 min. After stirring the mixture for 15 min., a solution of 4-bromophenacyl bromide (75.0 g, 270 mmol, manufactured by Tokyo Kasei Kogyo Co., Ltd.) in methylene chloride (350 ml) was added dropwise over 1 hr and 10 min keeping the temperature at −32° C. to −28° C. After stirring the mixture at the same temperature for 1 hr, the temperature was raised to 0° C. and methanol (10 ml) was added by small portions. Then, 0.5 M hydrochloric acid (300 ml) was added dropwise over 10 min and the mixture was stirred at room temperature for 40 min. The precipitate was filtered off and the filtrate was partitioned. The organic layer was separated and the aqueous layer was extracted with methylene chloride. The organic layers were combined, washed once with 0.5 M hydrochloric acid, twice with 0.1 M aqueous sodium hydroxide solution and once with saturated brine, and dried over anhydrous magnesium sulfate. The solvent was evaporated under reduced pressure to give the title compound (77.0 g, stoichiometric amount 75.6 g) as a pale-brown oil.

(2) Synthesis of (2S)-2-(4-bromophenyl)oxirane

The compound (77.0 g) obtained in the above-mentioned (1) was dissolved in diethyl ether (400 ml), the solution was stirred with 1M aqueous sodium hydroxide solution (400 ml) in a two-layer system at room temperature for 5 hr. After the completion of the reaction, the mixture was partitioned, the organic layer was separated, and the aqueous layer was extracted with diethyl ether. The organic layers were combined, washed once with saturated brine and dried over anhydrous magnesium sulfate. The solvent was evaporated under reduced pressure to give the title compound (55.0 g, stoichiometric amount 53.7 μg) as a pale-brown oil.

(3) Synthesis of (1S)-1-(4-bromophenyl)-2-((1R)-1-phenylethylamino)ethanol

The compound (55.0 g) obtained in the above-mentioned (2) and (R)-1-phenylethylamine (98.2 g, 810 mmol, manufactured by Tokyo Kasei Kogyo Co., Ltd.) were stirred in an oil bath with heating at 80° C. for 6 hrs. Excess amine was evaporated under reduced pressure to give a solid residue. Isopropyl ether (200 ml) was added and the solid was pulverized and collected by filtration to give the title compound (57.0 g) as white crystals. Furthermore, the filtrate was concentrated under reduced pressure, and the residue was stood overnight in a refrigerator to allow partial crystallization. Isopropyl ether (30 ml) was added and the crystals were collected by filtration to give the title compound (5.60 g). The crystals were combined to give 62.6 g (yield 72.4% for 3 steps).

(4) Synthesis of (6S)-6-(4-bromophenyl)-4-((1R)-1-phenylethyl)morpholin-3-one

To a solution of compound (62.6 g, 195 mmol) obtained in the above-mentioned (3) and triethylamine (21.8 g, 215 mmol) in methylene chloride (600 ml) was added dropwise over 30 min a solution of chloroacetyl chloride (24.3 g, 215 mmol, manufactured by Tokyo Kasei Kogyo Co., Ltd.) in methylene chloride (100 ml) under ice-cooling. After allowing to react under ice-cooling for 1 hr, the reaction mixture was washed twice with 0.5 M hydrochloric acid, once with saturated aqueous sodium hydrogencarbonate solution and once with saturated brine, and dried over anhydrous magnesium sulfate. The solvent was evaporated under reduced pressure and the obtained pale-brown oil was dissolved in isopropyl alcohol (600 ml) and aqueous potassium hydroxide solution (85%, 16.1 g, 244 mmol) was added. The mixture was stirred at room temperature for 16 hrs. The solvent was evaporated under reduced pressure and ethyl acetate was added. The mixture was washed once with water, twice with 0.5 M hydrochloric acid, once with saturated aqueous sodium hydrogencarbonate solution and once with saturated brine, and dried over anhydrous magnesium sulfate. The solvent was evaporated under reduced pressure to give the title compound (70.2 g, stoichiometric amount 70.2 g) as a brown oil.

(5) Synthesis of (2R)-2-(4-bromophenyl)-4-((1R)-1-phenylethyl)morpholine

To a solution of compound (70.2 g) obtained in the above-mentioned (4) in tetrahydrofuran (500 ml) was added dropwise over 45 min. borane-tetrahydrofuran complex (1.0 M solution in tetrahydrofuran, 510 ml, 510 mmol) under ice-cooling. After allowing to react under ice-cooling for 1 hr and at room temperature for 30 min, the mixture was ice-cooled again and methanol (60 ml) was added by small portions carefully to avoid foaming. The solvent was evaporated under reduced pressure, and methanol (750 ml) and 1 M aqueous sodium hydroxide solution (280 ml) were added to the residue. The mixture was stirred in an oil bath with heating at 80° C. for 1 hr, during which period 1 M aqueous sodium hydroxide solution (70 ml) was added 3 times every 15 min. After the completion of the reaction, methanol was evaporated under reduced pressure and water (500 ml) was added. The mixture was extracted twice with ethyl acetate. The organic layers were combined, washed once with water and twice with saturated brine, and dried over anhydrous magnesium sulfate. The solvent was evaporated under reduced pressure to give the title compound (65.0 g, yield 96.3% for 2 steps) as white crystals.

IR (ATR): 1487, 1449, 1117, 1098, 809, 758, 699, 550 cm$^{-1}$ $^1$H-NMR (CDCl$_3$) δ: 1.35 (3H, d), 2.10 (2H, m), 2.60 (1H, m), 3.05 (1H, m), 3.35 (1H, q), 3.75 (1H, m), 3.89 (1H, m), 4.55 (1H, m), 7.25 (7H, m), 7.46 (2H, d)

HPLC: 98.6% area ratio 99.2% diastereomer ratio
column; Inertsil ODS-3V 4.6×150 mm
developing solvent; CH$_3$CN/H$_2$O=28/72 (0.1% TFA)
flow rate; 1.0 ml/min

Example 5

Synthesis of (2S)-2-(4-fluorophenyl)morpholine

A suspension of (2S)-2-(4-fluorophenyl)-4-(benzyl)morpholine (250 mg) and 5% Pd—C (0.106 g) in ethanol (5 mL) was treated with hydrogen for 1 hr at 33-35° C. The suspension was filtered through celite and washed with ethanol. The solvent was evaporated to give (2S)-2-(4-fluorophenyl)morpholine (160 mg, 94%) as a white solid.

$^1$H-NMR (CDCl$_3$) δ: 2.75 (1H, dd, J=12.0, 12.0 Hz), 2.90 (1H, m), 2.95-3.05 (2H, m), 3.73-3.77 (1H, m), 4.01-4.04 (1H, m), 4.44-4.47 (1H, m), 7.00-7.04 (2H, m), 7.31-7.34 (2H, m).

Reference Example 1

(1) Synthesis of 2-mercapto-1-methyl-1H-[4,4']bipyrimidinyl-6-one

A solution of ethyl 3-oxo-3-pyrimidin-4-yl-propionate (36.10 g, 0.186 mol), N-methylthiourea (25.40 g, 0.282 mol) and 1,8-diazabicyclo[5.4.0]undec-7-ene (29.11 g, 0.191 mol) in ethanol (150 ml) was refluxed for 21 hrs. After removal of a half amount of ethanol under reduced pressure, hydrochloric acid was added to the solution. The resulting precipitate was collected by filtration, washed with water and then dried. The precipitate was stirred in hot ethyl acetate (1 L), and the precipitate was collected by filtration and dried to give 2-mercapto-1-methyl-1H-[4,4']bipyrimidinyl-6-one (33.91 g, 83%).

$^1$H-NMR (CDCl$_3$) δ: 3.59 (3H, s), 6.91 (1H, s), 8.27 (1H, d, J=2.4 Hz), 9.08 (1H, d, J=2.1 Hz), 9.41 (1H, s), 11.99 (1H, s)

(2) Synthesis of 2-chloro-1-methyl-1H-[4,4']bipyrimidinyl-6-one

A suspension of 2-mercapto-1-methyl-1H-[4,4']bipyrimidinyl-6-one (8.8 g, 40 mmol) in a mixed solvent of dimethylformamide (30 ml) and 1,2-dichloroethane (30 ml) was added to phosphorus oxychloride (11.2 ml, 120 mmol), and the mixture was stirred at 65° C. for 50 min. After the solution was poured into ice-cooled dichloromethane (300 ml), water was added and the mixture was stirred vigorously for 5 min. Aqueous sodium carbonate solution (25.4 g, 240 mmol, in water (100 ml)) was added and the pH was adjusted to 8 with saturated aqueous sodium hydrogencarbonate solution. Aqueous sodium hypochlorite solution (5% in water, 120 ml) was added. After filtration through celite, the organic layer was separated and the aqueous layer was extracted with dichloromethane twice. The organic layers were combined and washed with saturated aqueous sodium hydrogencarbonate solution and dried over sodium sulfate. The solvent was evaporated under reduced pressure, the residue was purified by silica gel column chromatography (eluent; ethyl acetate/hexane=1/1) and wash with diethyl ether to give 2-chloro-1-methyl-1H-[4,4']bipyrimidinyl-6-one (2.2 g, 62%, 98.7% purity) as a pale-yellow solid.

$^1$H-NMR (CDCl$_3$) δ: 3.74 (3H, s), 7.58 (1H, s), 8.19 (1H, d, J=5.7 Hz), 8.92 (1H, d, J=5.2 Hz), 9.31 (1H, d, J=1.1 Hz)

(3) Synthesis of 2-[(2S)-2-(2-(4-fluorophenyl)morpholin-4-yl)]-1-methyl-1H-[4,4']bipyrimidinyl-6-one A solution of (2S)-2-(4-fluorophenyl)morpholine hydrochloride (108.6 mg, 0.60 mmol), 2-chloro-1-methyl-1H-[4, 4']bipyrimidinyl-6-one (88.4 mg, 0.40 mmol) and triethylamine (0.27 ml, 2.0 mmol) in tetrahydrofuran (2 ml) was stirred at room temperature for several hours. The precipitate was filtered off after cooling, and the solvent was evaporated in vacuo. The residue was washed with ethyl acetate to give the title compound (100 mg, 74%)

$^1$H-NMR (CDCl$_3$) δ: 3.09 (dd, J=12.9, 10.8 Hz, 1H), 3.29 (m, 1H), 3.52-3.64 (m, 2H), 3.59 (s, 3H), 4.00 (m, 1H), 4.21 (m, 1H), 4.72 (dd, J=10.5, 2.1 Hz, 1H), 7.07-7.13 (m, 2H), 7.38-7.43 (m, 3H), 8.13 (dd, J=5.4, 1.2 Hz, 1H) 8.88 (d, J=5.1 Hz, 1H), 9.28 (s, 1H).

MS [M+H]$^+$: 367.

Example 6

(1) Synthesis of ethyl orotate

Orotic acid monohydrate (53.19 g, 0.306 mmol) was added to a solution of 1,8-diazabicyclo[5.4.0]undec-7-ene (46.51 g, 0.306 mmol) in dimethylformamide (85 ml). After stirring for 5 min., ethyl iodide (57.14 g, 0.366 mmol) was added to the solution and the mixture was heated at 60° C. for 5 hrs. Water (1 L) was added, and the resulting precipitate was collected by filtration, washed with water, and dried to give ethyl orotate (49.25 g, 88%).

$^1$H NMR (DMSO-d$_6$) δ: 1.29 (3H, dt, J=1.5, 6.9 Hz), 4.31 (2H, dq, J=1.2, 7.2 Hz), 6.04 (1H, d, J=1.2 Hz), 11.11 (1H, s), 11.37 (1H, s)

(2) Synthesis of ethyl 2,6-dichloropyrimidine-4-carboxylate

N,N-Diethylaniline (60 ml, 0.377 mmol) was added to a mixture of ethyl orotate (97.70 g, 0.531 mmol) and phosphorus oxychloride (120 ml, 1.31 mol) and the mixture was refluxed for 70 min. The solution was poured into ice water, and the resulting solid was collected by filtration and washed with water. This solid was dissolved in ethyl acetate, and the solution was filtered through silica gel, dried over sodium sulfate, and concentrated under reduced pressure. The obtained residue was purified by short silica gel column chromatography (eluent; hexane/ethyl acetate=2/1) to give ethyl 2,6-dichloropyrimidine-4-carboxylate (99.94 g, 85%).

$^1$H NMR (CDCl$_3$) δ: 1.45 (3H, t, J=7.3 Hz), 4.51 (3H, q, J=7.1 Hz), 7.97 (1H, s)

(3) Synthesis of ethyl pyrimidine-4-carboxylate

Triethylamine (48.03 g, 0.475 mmol) was added to a solution of ethyl 2,6-dichloropyrimidine-4-carboxylate (38.60 g, 0.175 mmol) in tetrahydrofuran (700 ml). 5% Palladium-carbon was added and the mixture was stirred under a hydrogen atmosphere for 6 hrs. The solid in the reaction system was removed by filtration, and the filtrate was concentrated under reduced pressure. The obtained residue was purified by silica gel column chromatography to give ethyl pyrimidine-4-carboxylate (23.06 g, 87%).

$^1$H NMR (CDCl$_3$) δ: 1.46 (3H, t, J=7.1 Hz), 4.52 (2H, q, J=7.1 Hz), 8.03 (1H, dd, J=1.7, 5.0 Hz), 9.00 (1H, d, J=5.0 Hz), 9.42 (1H, d, J=1.4 Hz)

(4) Synthesis of ethyl 3-oxo-3-(pyrimidin-4-yl)propionate

A solution of ethanol (16.18 g, 0.351 mol) in diethyl ether (15 ml) was added to a solution of sodium hydride (13.71 g, 0.343 mol, 60% in paraffin, paraffin was removed by washing with hexane) in diethyl ether (100 ml). After stirring the mixture for 30 min, the solvent was evaporated under reduced pressure, and toluene (100 ml) was added. A solution of ethyl pyrimidine-4-carboxylate (30.86 g, 0.203 mol) and ethyl acetate (30.48 g, 0.346 mol) in toluene (100 ml) was added, and the mixture was heated at 80° C. for 3 hrs. Hydrochloric acid was added, then sodium bicarbonate was added to adjust to pH 4. The solution was partitioned between water and ethyl acetate. The organic layer was washed with brine and dried over sodium sulfate. The solvent was evaporated under reduced pressure to give ethyl 3-oxo-3-(pyrimidin-4-yl)propionate (36.10 g, 92%).

$^1$H NMR (CDCl$_3$) δ: 1.35 (3H, t, J=6.9 Hz), 4.31 (2H, q, J=7.2 Hz), 6.47 (1H, s), 7.84 (1H, dd, J=1.5, 5.4 Hz), 8.89 (1H, d, J=5.1 Hz), 9.24 (1H, d, J=1.2 Hz), 12.22 (1H, s)

(5) Synthesis of ethyl 3-oxo-3-(pyrimidin-4-yl)propionate

To a 25% solution (5.31 g, 10.52 mmol) of potassium tert-amylate in toluene was added dropwise a solution of ethyl pyrimidine-4-carboxylate (1.00 g, 6.57 mmol) and ethyl acetate (1.09 mL, 11.1 mmol) in toluene (2.4 ml) at room temperature. Disappearance of the ethyl ester was confirmed by HPLC analysis, water (5 mL), ethyl acetate (5 mL) and concentrated hydrochloric acid (0.45 mL) were added, and the mixture was extracted with ethyl acetate (4 mL). The organic layer was dried over sodium sulfate, and the solvent was evaporated under reduced pressure to give ethyl 3-oxo-3-(pyrimidin-4-yl)propionate (0.97 g, 76%).

Reference Example 2

(1) Synthesis of 2-mercapto-1-methyl-1H-[4,4']bipyrimidinyl-6-one

A solution of ethyl 3-oxo-3-(pyrimidin-4-yl)propionate (36.10 g, 0.186 mol), N-methylthiourea (25.40 g, 0.282 mol) and 1,8-diazabicyclo[5.4.0]undec-7-ene (29.11 g, 0.191 mol) in ethanol (150 ml) was refluxed for 21 hrs. A half amount of ethanol was evaporated under reduced pressure and hydrochloric acid was added. The resulting precipitate was collected by filtration, washed with water and dried. The precipitate was stirred in hot ethyl acetate (1 L), and the precipitate was collected by filtration and dried to give 2-mercapto-1-methyl-1H-[4,4']bipyrimidinyl-6-one (33.91 g, 83%).

$^1$H NMR (CDCl$_3$) δ: 3.59 (3H, s), 6.91 (1H, s), 8.27 (1H, d, J=2.4 Hz), 9.08 (1H, d, J=2.1 Hz), 9.41 (1H, s), 11.99 (1H, s)

(2) Synthesis of 2-chloro-1-methyl-1H-[4,4']bipyrimidinyl-6-one

A suspension of 2-mercapto-1-methyl-1H-[4,4']bipyrimidinyl-6-one (8.8 g, 40 mmol) in a mixed solvent of dimethylformamide (30 ml) and 1,2-dichloroethane (30 ml) was added to phosphorus oxychloride (11.2 ml, 120 mmol), and the mixture was stirred at 65° C. for 50 min. The solution was poured into ice-cooled dichloromethane (300 ml), water was added and the mixture was vigorously stirred for 5 min. Aqueous sodium carbonate solution (25.4 g, 240 mmol, in water (100 ml)) was added and the pH was adjusted to 8 with saturated aqueous sodium hydrogencarbonate solution. Aqueous sodium hypochlorite solution (5% in water, 120 ml) was added. After filtration through celite, the organic layer was extracted twice with dichloromethane, and washed with saturated aqueous sodium bicarbonate solution and dried over sodium sulfate. The solvent was evaporated under reduced pressure, and the obtained residue was purified by silica gel column chromatography (eluent; ethyl acetate/hexane=1/1) and washed with diethyl ether to give 2-chloro-1-methyl-1H-[4,4']bipyrimidinyl-6-one as a pale-yellow solid (2.2 g, 62%, purity 98.7%).

$^1$H NMR (CDCl$_3$) δ: 3.74 (3H, s), 7.58 (1H, s), 8.19 (1H, d, J=5.7 Hz), 8.92 (1H, d, J=5.2 Hz), 9.31 (1H, d, J=1.1 Hz)

(3) Synthesis of 2-[(2S)-2-(2-(4-fluorophenyl)morpholin-4-yl)]-1-methyl-1H-[4,4']bipyrimidinyl-6-one A solution of (2S)-2-(4-fluorophenyl)morpholine hydrochloride (108.6 mg, 0.60 mmol), 2-chloro-1-methyl-1H-[4,4']bipyrimidinyl-6-one (88.4 mg, 0.40 mmol) and triethylamine (0.27 ml, 2.0 mmol) in tetrahydrofuran (2 ml) was stirred at room temperature for several hours. After cooling, the resulting precipitate was removed by filtration, and the solvent was evaporated in vacuo. The obtained residue was washed with ethyl acetate to give 2-[(2S)-2-(2-(4-fluorophenyl)morpholin-4-yl)]-1-methyl-1H-[4,4']bipyrimidinyl-6-one (100 mg, 74%).

$^1$H-NMR (CDCl$_3$) δ: 3.09 (dd, J=12.9, 10.8 Hz, 1H), 3.29 (m, 1H), 3.52-3.64 (m, 2H), 3.59 (s, 3H), 4.00 (m, 1H), 4.21 (m, 1H), 4.72 (dd, J=10.5, 2.1 Hz, 1H), 7.07-7.13 (m, 2H), 7.38-7.43 (m, 3H), 8.13 (dd, J=5.4, 1.2 Hz, 1H), 8.88 (d, J=5.1 Hz, 1H), 9.28 (s, 1H).

MS [M$^+$H]$^+$: 367

Industrial Applicability

According to the production method of the present invention, an optically active 2-aryl-substituted morpholine compound and 3-oxo-3-(pyrimidin-4-yl)propionate, which are important as starting materials for synthesizing compounds such as 2-(2-arylmorpholin-4-yl)-1-methyl-1H-[4,4']bipyrimidinyl-6-one and the like having a tau protein kinase 1 inhibitory activity and useful as a therapeutic drug for Alzheimer's disease and the like, can be produced in a high yield by an industrially advantageous method.

This application is based on patent application Nos. 2005/213311, 2005/267485 and 2006/015436 filed in Japan, the contents of which are hereby incorporated by reference.

The invention claimed is:
1. A production method of an optically active morpholine compound represented by the formula 10, which comprises the following steps:

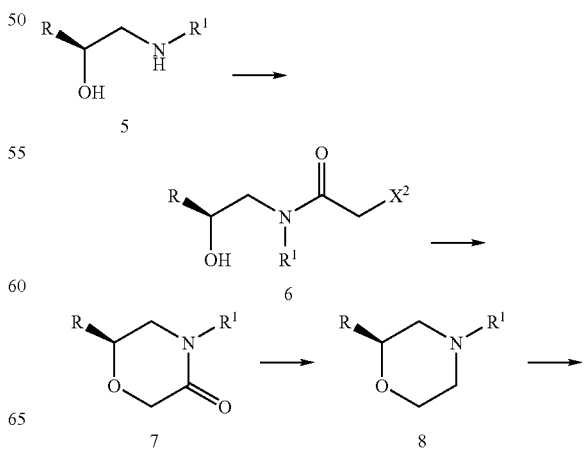

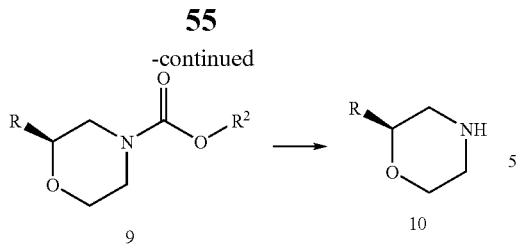

wherein R is an aryl optionally having substituent(s) or a heteroaryl optionally having substituent(s), $R^1$ is a $C_1$-$C_6$ alkyl, an aralkyl optionally having substituent(s) or a $C_2$-$C_6$ alkenyl, $R^2$ is a $C_1$-$C_6$ alkyl, a $C_1$-$C_6$ haloalkyl, an aryl optionally having substituent(s) or a benzyl optionally having substituent(s), and $X^2$ is a halogen,

- step 1) reacting a compound of the formula 5 with an activated chloroacetic acid or bromoacetic acid in a solvent to give a compound of the formula 6,
- step 2) reacting the compound of the formula 6 with a base to give a compound of the formula 7,
- step 3) reacting the compound of the formula 7 with a reducing agent in a solvent to give a compound of the formula 8,
- step 4) reacting the compound of the formula 8 with a chloroformate to give a compound of the formula 9, and
- step 5) subjecting the compound of the formula 9 to hydrolysis to give the compound of the formula 10.

2. A production method of an optically active morpholine compound represented by the formula 30, which comprises the following steps:

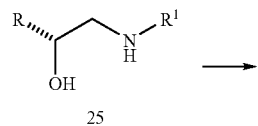

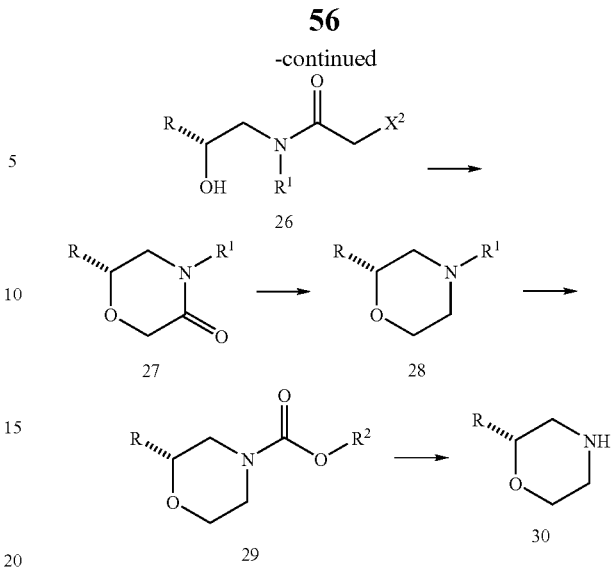

wherein R is an aryl optionally having substituent(s) or a heteroaryl optionally having substituent(s), $R^1$ is a $C_1$-$C_6$ alkyl, an aralkyl optionally having substituent(s) or a $C_2$-$C_6$ alkenyl, $R^2$ is a $C_1$-$C_6$ alkyl, a $C_1$-$C_6$ haloalkyl, an aryl optionally having substituent(s) or a benzyl optionally having substituent(s), and $X^2$ is a halogen,

- step 1) reacting a compound of the formula 25 with an activated chloroacetic acid or bromoacetic acid in a solvent to give a compound of the formula 26,
- step 2) reacting the compound of the formula 26 with a base to give a compound of the formula 27,
- step 3) reacting the compound of the formula 27 with a reducing agent in a solvent to give a compound of the formula 28,
- step 4) reacting the compound of the formula 28 with a chloroformate to give a compound of the formula 29, and
- step 5) subjecting the compound of the formula 29 to hydrolysis to give the compound of the formula 30.

* * * * *